(12) United States Patent
Skinlo et al.

(10) Patent No.: US 11,510,666 B2
(45) Date of Patent: Nov. 29, 2022

(54) METHOD AND APPARATUS FOR TREATING A HIP JOINT, INCLUDING THE PROVISION AND USE OF A NOVEL SUTURE PASSER

(71) Applicant: Stryker Corporation, Kalamazoo, MI (US)

(72) Inventors: David Skinlo, Logan, UT (US); Scott Heneveld, Whitmore, CA (US); Thomas Weisel, Ventura, CA (US); Roger Pisarnwongs, Valencia, CA (US)

(73) Assignee: Stryker Corporation, Kalamazoo, MI (US)

( * ) Notice: Subject to any disclaimer, the term of this patent is extended or adjusted under 35 U.S.C. 154(b) by 351 days.

(21) Appl. No.: 16/515,407

(22) Filed: Jul. 18, 2019

(65) Prior Publication Data
US 2020/0046341 A1 Feb. 13, 2020

Related U.S. Application Data

(63) Continuation of application No. 14/955,451, filed on Dec. 1, 2015, now Pat. No. 10,357,243, which is a
(Continued)

(51) Int. Cl.
| | | |
|---|---|---|
| *A61B 17/04* | (2006.01) | |
| *A61B 17/06* | (2006.01) | |
| *A61B 17/29* | (2006.01) | |

(52) U.S. Cl.
CPC ...... *A61B 17/0469* (2013.01); *A61B 17/0482* (2013.01); *A61B 17/0483* (2013.01);
(Continued)

(58) Field of Classification Search
CPC .......... A61B 2017/06009; A61B 2017/06014; A61B 2017/06042
See application file for complete search history.

(56) References Cited

U.S. PATENT DOCUMENTS

| | | |
|---|---|---|
| 1,037,864 A | 9/1912 | Carlson et al. |
| 1,449,087 A | 3/1923 | Bugbee |

(Continued)

FOREIGN PATENT DOCUMENTS

| | | |
|---|---|---|
| EP | 1703846 B1 | 4/2013 |
| WO | 95/25468 A1 | 9/1995 |

(Continued)

OTHER PUBLICATIONS

Decision to Grant dated Jun. 1, 2017, directed to EP Application No. 10 800 336.9; 2 pages.
(Continued)

*Primary Examiner* — Todd J Scherbel
(74) *Attorney, Agent, or Firm* — Morrison & Foerster LLP

(57) ABSTRACT

A suture passer comprising:
a shaft having an axis;
a first jaw mounted to the shaft in alignment with the axis, the first jaw being configured to releasably support a length of suture thereon;
a second jaw movably mounted to the shaft; and
a needle movably mounted to the shaft, the needle having a hook and being configured to reciprocate in alignment with the axis so that the hook can selectively pass by the second jaw and engage suture releasably supported on the first jaw;
wherein the first jaw comprises a spring for selectively binding the suture to the first jaw, and further wherein the spring comprises a recess for receiving the suture therein.

23 Claims, 75 Drawing Sheets

Related U.S. Application Data continuation of application No. 13/564,087, filed on Aug. 1, 2012, now Pat. No. 9,198,655, which is a continuation-in-part of application No. 12/831,937, filed on Jul. 7, 2010, now Pat. No. 8,469,974.

(60) Provisional application No. 61/513,869, filed on Aug. 1, 2011, provisional application No. 61/327,431, filed on Apr. 23, 2010, provisional application No. 61/270,985, filed on Jul. 15, 2009.

(52) U.S. Cl.
CPC ........ *A61B 17/06066* (2013.01); *A61B 17/04* (2013.01); *A61B 17/0485* (2013.01); *A61B 17/0491* (2013.01); *A61B 17/06004* (2013.01); *A61B 2017/061* (2013.01); *A61B 2017/06009* (2013.01); *A61B 2017/06014* (2013.01); *A61B 2017/06042* (2013.01); *A61B 2017/06052* (2013.01); *A61B 2017/2926* (2013.01)

(56) References Cited

U.S. PATENT DOCUMENTS

| | | | |
|---|---|---|---|
| 1,635,066 A | 7/1927 | Wells | |
| 1,815,725 A | 7/1931 | Pilling et al. | |
| 1,822,330 A | 9/1931 | Ainslie | |
| 1,856,721 A | 5/1932 | Nagelmann | |
| 2,457,379 A | 12/1948 | Kallenbach | |
| 2,579,192 A | 12/1951 | Kohl | |
| 2,738,790 A | 3/1956 | Todt, Sr. et al. | |
| 2,813,736 A | 11/1957 | Archer et al. | |
| 2,959,172 A | 11/1960 | Held | |
| 3,470,875 A | 10/1969 | Johnson | |
| 3,842,840 A | 10/1974 | Schweizer | |
| 3,901,244 A | 8/1975 | Schweizer | |
| 3,946,740 A | 3/1976 | Bassett | |
| 4,164,225 A | 8/1979 | Johnson et al. | |
| 4,224,947 A | 9/1980 | Fukuda | |
| 4,312,337 A | 1/1982 | Donohue | |
| 4,373,530 A | 2/1983 | Kilejian | |
| 4,596,249 A | 6/1986 | Freda et al. | |
| 4,602,635 A | 7/1986 | Mulhollan et al. | |
| 4,712,545 A | 12/1987 | Honkanen | |
| 4,759,364 A | 7/1988 | Boebel | |
| 4,836,205 A | 6/1989 | Barrett | |
| 4,890,615 A | 1/1990 | Caspari et al. | |
| 4,923,461 A | 5/1990 | Caspari et al. | |
| 5,059,201 A | 10/1991 | Asnis | |
| 5,281,237 A | 1/1994 | Gimpelson | |
| 5,312,422 A | 5/1994 | Trott | |
| 5,312,423 A | 5/1994 | Rosenbluth et al. | |
| 5,336,229 A | 8/1994 | Noda | |
| 5,364,410 A | 11/1994 | Failla et al. | |
| 5,376,096 A | 12/1994 | Foster | |
| 5,387,227 A | 2/1995 | Grice | |
| 5,389,103 A | 2/1995 | Melzer et al. | |
| 5,499,991 A | 3/1996 | Garman et al. | |
| 5,507,754 A | 4/1996 | Green et al. | |
| 5,569,269 A | 10/1996 | Hart et al. | |
| 5,618,290 A | 4/1997 | Toy et al. | |
| 5,643,292 A | 7/1997 | Hart | |
| 5,649,939 A | 7/1997 | Reddick | |
| 5,746,753 A | 5/1998 | Sullivan et al. | |
| 5,792,153 A | 8/1998 | Swain et al. | |
| 5,890,538 A | 4/1999 | Beirute et al. | |
| 5,904,692 A | 5/1999 | Steckel et al. | |
| 5,980,538 A | 11/1999 | Fuchs et al. | |
| 5,993,466 A | 11/1999 | Yoon | |
| 6,117,144 A | 9/2000 | Nobles et al. | |
| 6,443,963 B1 | 9/2002 | Baldwin et al. | |
| 6,517,552 B1 | 2/2003 | Nord et al. | |
| 6,551,330 B1* | 4/2003 | Bain ................. | A61B 17/0469 606/144 |
| 6,770,084 B1 | 8/2004 | Bain et al. | |
| 6,893,448 B2 | 5/2005 | O'Quinn et al. | |
| 6,936,054 B2 | 8/2005 | Chu | |
| 7,083,628 B2 | 8/2006 | Bachman | |
| 7,118,583 B2 | 10/2006 | O'Quinn et al. | |
| 7,211,093 B2 | 5/2007 | Sauer et al. | |
| 7,377,926 B2 | 5/2008 | Topper et al. | |
| 7,407,505 B2 | 8/2008 | Sauer et al. | |
| 7,544,199 B2 | 6/2009 | Bain et al. | |
| 7,608,084 B2* | 10/2009 | Oren ................. | A61B 17/0469 606/144 |
| 7,815,654 B2 | 10/2010 | Chu | |
| 7,879,048 B2 | 2/2011 | Bain et al. | |
| 8,172,857 B2 | 5/2012 | Fogel | |
| 8,361,089 B2 | 1/2013 | Chu | |
| 8,469,974 B2* | 6/2013 | Skinlo ................ | A61B 17/0482 606/144 |
| 8,764,771 B2 | 7/2014 | Chu | |
| 8,906,041 B2 | 12/2014 | Chu | |
| 9,198,655 B2 | 12/2015 | Skinlo et al. | |
| 9,271,719 B2* | 3/2016 | Skinlo ................ | A61B 17/0469 |
| 10,278,690 B2* | 5/2019 | Skinlo ................ | A61B 17/0469 |
| 2002/0116067 A1 | 8/2002 | Mears et al. | |
| 2005/0090827 A1 | 4/2005 | Gedebou | |
| 2005/0222589 A1 | 10/2005 | Chu | |
| 2005/0251153 A1 | 11/2005 | Sakamoto et al. | |
| 2006/0282094 A1 | 12/2006 | Stokes et al. | |
| 2007/0213833 A1 | 9/2007 | Mears et al. | |
| 2007/0270885 A1 | 11/2007 | Weinert et al. | |
| 2008/0077162 A1* | 3/2008 | Domingo ........... | A61B 17/0482 606/146 |
| 2009/0062819 A1 | 3/2009 | Burkhart et al. | |
| 2009/0069846 A1 | 3/2009 | Bull et al. | |
| 2009/0131956 A1 | 5/2009 | Dewey et al. | |
| 2010/0121348 A1 | 5/2010 | van der Burg et al. | |
| 2010/0121352 A1 | 5/2010 | Murray et al. | |
| 2010/0256657 A1 | 10/2010 | Domingo | |
| 2011/0060352 A1 | 3/2011 | Chu | |
| 2011/0144442 A1 | 6/2011 | Farrell et al. | |
| 2013/0041387 A1 | 2/2013 | Skinlo et al. | |
| 2013/0103056 A1 | 4/2013 | Chu | |
| 2013/0231669 A1 | 9/2013 | Sinnott et al. | |
| 2016/0338691 A1 | 11/2016 | Weber et al. | |

FOREIGN PATENT DOCUMENTS

| | | |
|---|---|---|
| WO | 02/24078 A1 | 3/2002 |
| WO | 2008/130656 A1 | 10/2008 |

OTHER PUBLICATIONS

Extended European Search Report dated Mar. 6, 2015, directed to EP Application No. 10 800 336.9; 5 pages.

Intention to Grant dated Jan. 13, 2017, directed to EP Application No. 10 800 336.9; 5 pages.

International Preliminary Report on Patentability dated Jan. 17, 2012, directed to International Application No. PCT/US2010/041230; 8 pages.

International Search Report and Written Opinion dated Sep. 7, 2010, directed to International Application No. PCT/US2010/041230; 10 pages.

Notice of Acceptance dated Sep. 22, 2015, directed to AU Application No. 2010273677; 2 pages.

Notice of Allowance dated Mar. 8, 2019, directed to CA Application No. 2,767,713; 1 page.

Office Action dated Apr. 18, 2016, directed to EP Application No. 10 800 336.9; 4 pages.

Office Action dated Aug. 22, 2016, directed to CA Application No. 2,767,713; 5 pages.

Office Action dated Jan. 26, 2018, directed to CA Application No. 2,767,713; 3 pages.

Office Action dated Jul. 4, 2017, directed to CA Application No. 2,767,713; 3 pages.

Office Action dated Oct. 30, 2018, directed to CA Application No. 2767713; 5 pages.

Patent Examination Report No. 1 dated Mar. 18, 2014, directed to AU Application No. 2010273677; 4 pages.

(56) References Cited

OTHER PUBLICATIONS

Patent Examination Report No. 2 dated Mar. 19, 2015, directed to AU Application No. 2010273677; 4 pages.
Skinlo et al., Office Action dated Feb. 23, 2018, directed to U.S. Appl. No. 14/955,451; 13 pages.
Skinlo et al., Office Action dated Jul. 26, 2018, directed to U.S. Appl. No. 14/955,451; 12 pages.
Skinlo et al., Office Action dated Oct. 14, 2014, directed to U.S. Appl. No. 13/564,087; 26 pages.
Skinlo et al., U.S. Corrected Notice of Allowability dated Jan. 28, 2019, directed to U.S. Appl. No. 15/048,000; 6 pages.
Skinlo et al., U.S. Notice of Allowance and Fee(s) Due dated Dec. 11, 2015, directed to U.S. Appl. No. 13/925,242; 17 pages.
Skinlo et al., U.S. Notice of Allowance and Fee(s) due dated Dec. 27, 2018, directed to U.S. Appl. No. 15/048,000; 11 pages.
Skinlo et al., U.S. Notice of Allowance and Fee(s) Due dated Jul. 17, 2015, directed to U.S. Appl. No. 13/564,087; 12 pages.
Skinlo et al., U.S. Notice of Allowance and Fee(s) due dated Mar. 25, 2019, directed to U.S. Appl. No. 14/955,451; 9 pages.
Skinlo et al., U.S. Notice of Allowance and Fee(s) due dated Mar. 4, 2013, directed to U.S. Appl. No. 12/831,937; 10 pages.
Skinlo et al., U.S. Office Action dated Apr. 29, 2015, directed to U.S. Appl. No. 13/925,242; 15 pages.
Skinlo et al., U.S. Office Action dated Jul. 31, 2014, directed to U.S. Appl. No. 13/925,242; 19 pages.
Skinlo et al., U.S. Office Action dated May 22, 2018, directed to U.S. Appl. No. 15/048,000; 13 pages.
Skinlo et al., U.S. Office Action dated Sep. 4, 2012, directed to U.S. Appl. No. 12/831,937; 22 pages.
Skinlo et al., U.S. Restriction Requirement dated May 19, 2014, directed to U.S. Appl. No. 13/564,087; 11 pages.
Skinlo et al., U.S. Restriction Requirement dated Jun. 1, 2012, directed to U.S. Appl. No. 12/831,937; 10 pages.
Skinlo et al., U.S. Restriction Requirement dated Nov. 22, 2017, directed to U.S. Appl. No. 14/955,451; 10 pages.

* cited by examiner

CAM-TYPE FEMOROACETABULAR IMPINGEMENT (FAI)
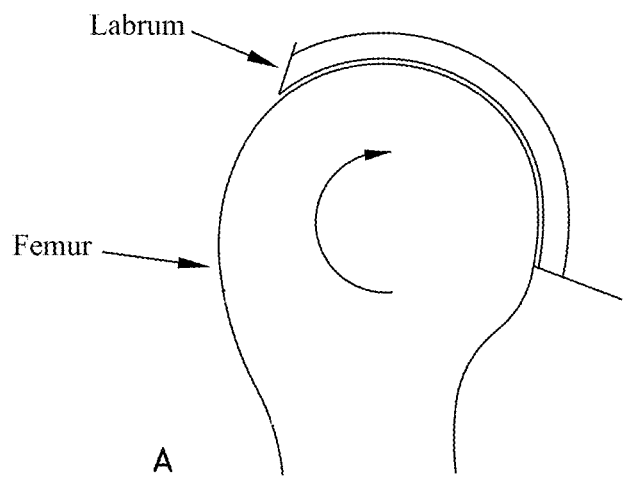
CAM INJURY TO THE LABRUM
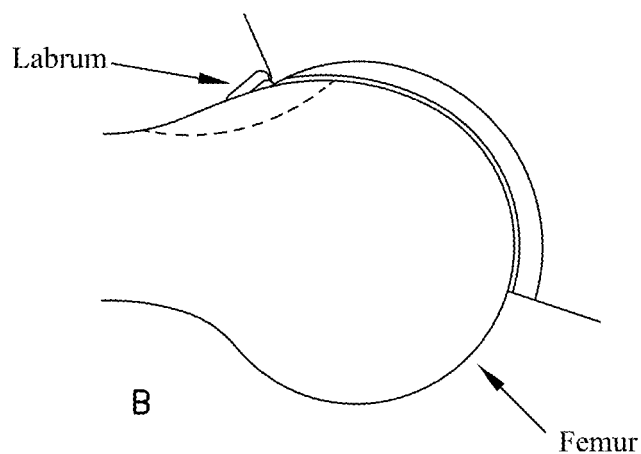
FIG. 13

PINCER-TYPE FEMOROACETABULAR IMPINGEMENT (FAI)
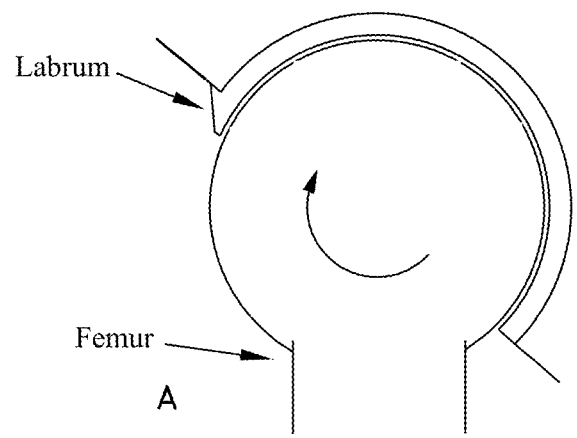
PINCER INJURY TO THE LABRUM
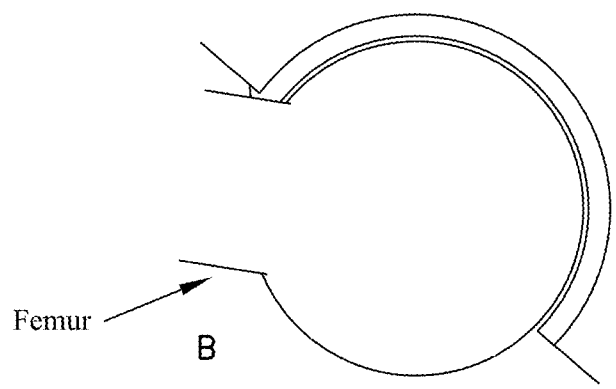
FIG. 14

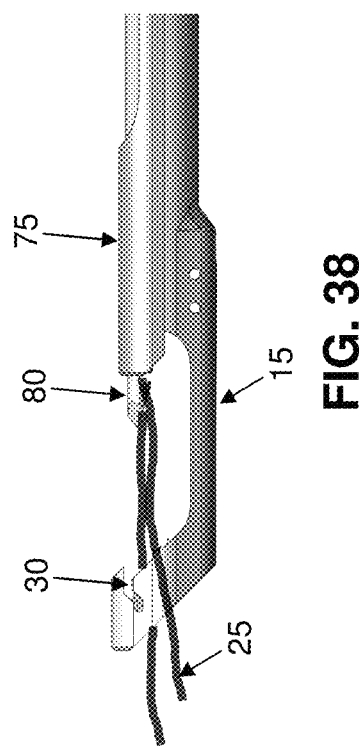

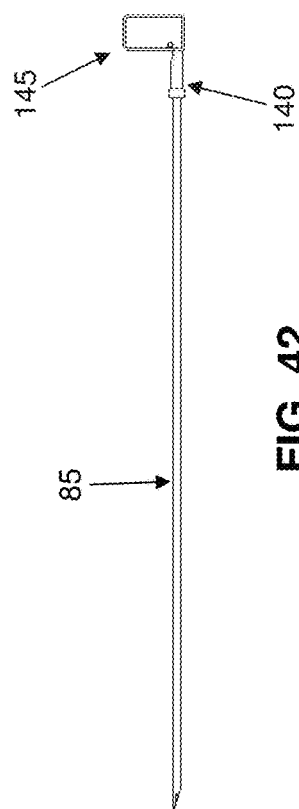
FIG. 41
FIG. 42
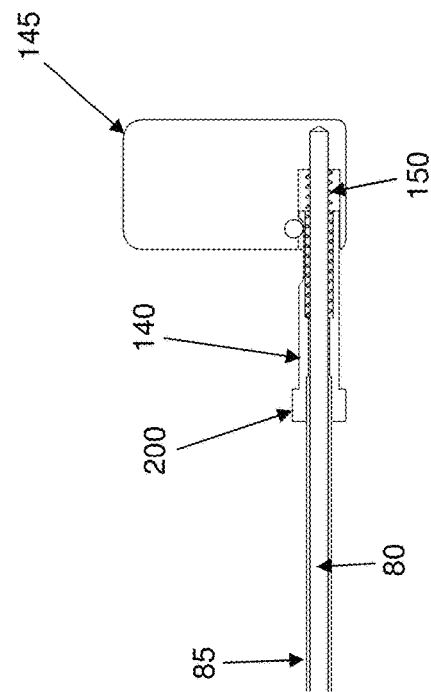
FIG. 43
FIG. 44
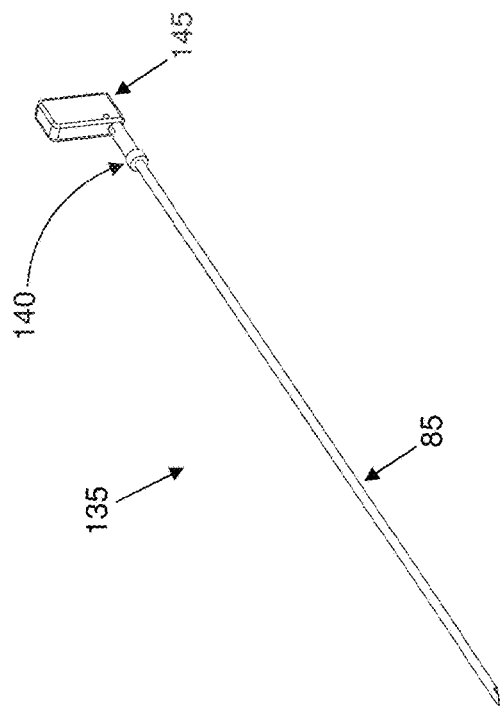

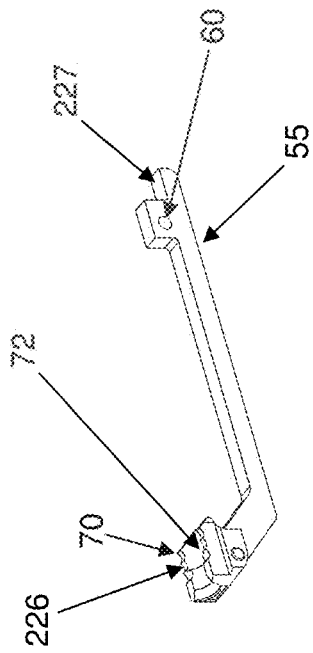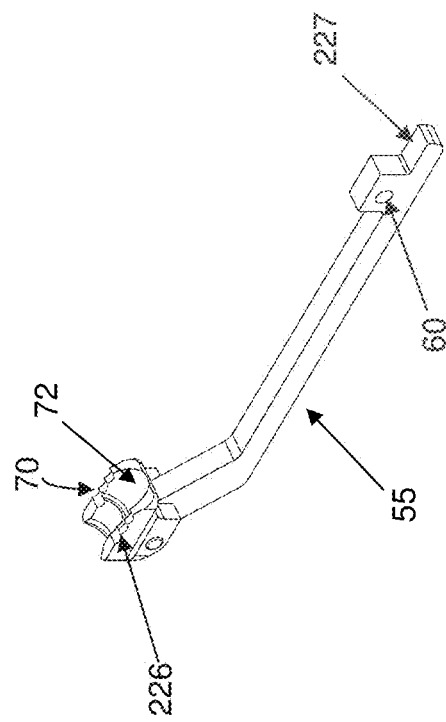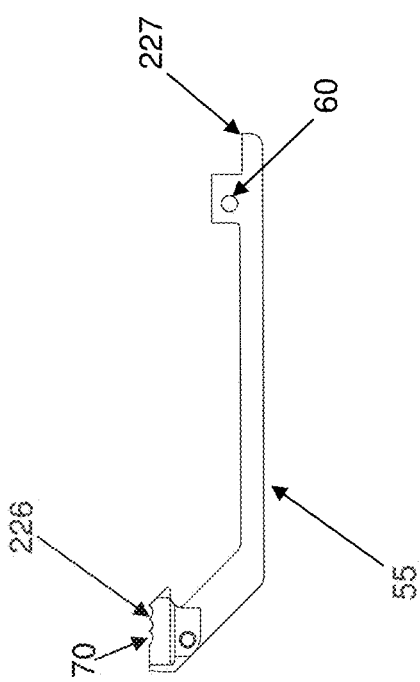
FIG. 50B
FIG. 50C
FIG. 50A

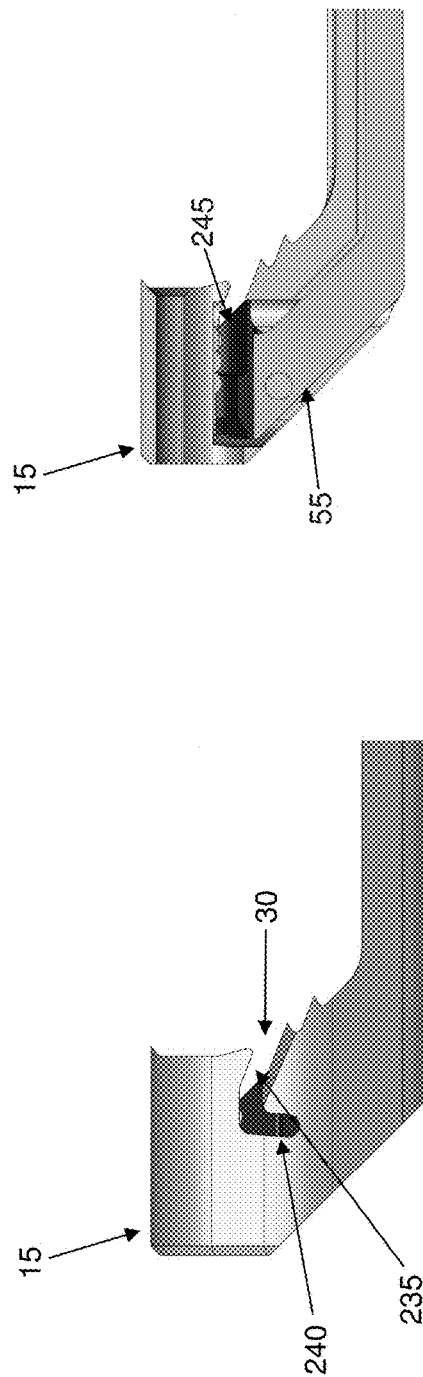
FIG. 55
FIG. 56
Pre Load
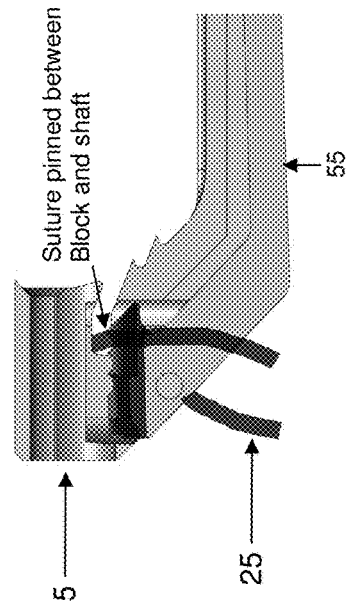
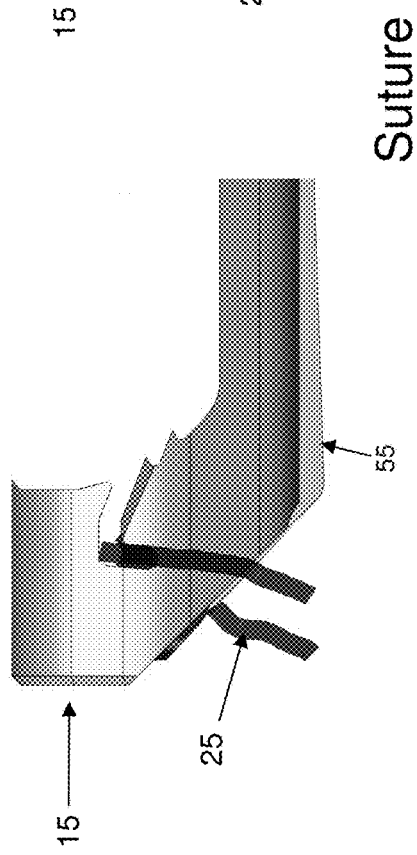
FIG. 57
FIG. 58
Suture Loaded Initial Tissue Puncture Needle rides over suture Pushing suture and spring/block down Continued Needle Passing Full Inner Needle Deployment Initial Suture Capture

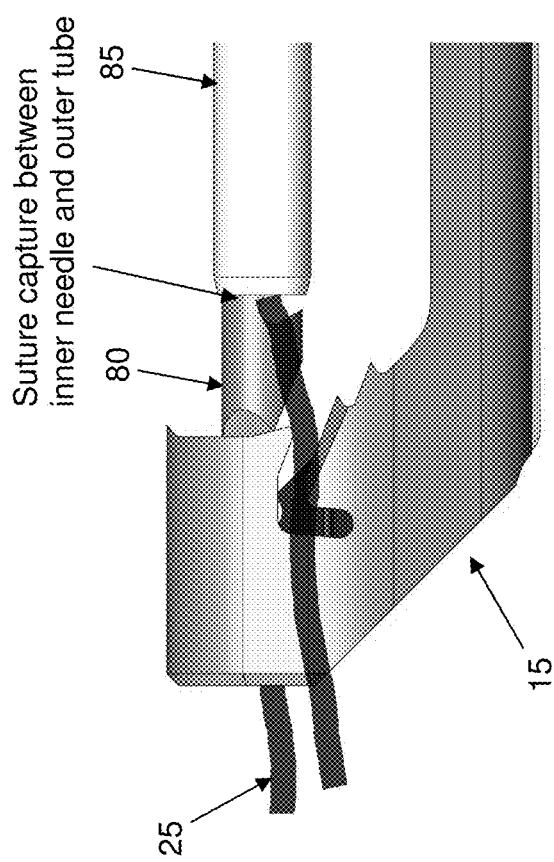
FIG. 67 Suture capture between inner needle and outer tube
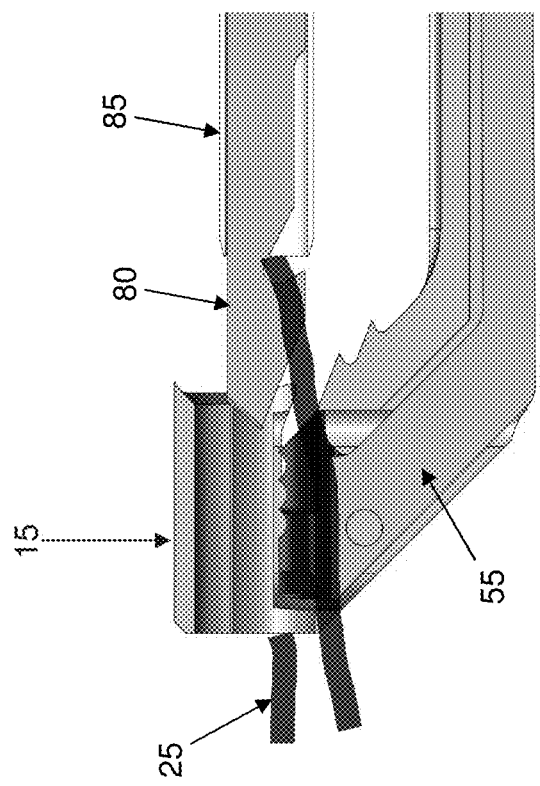
FIG. 68
Retract needle with captured suture

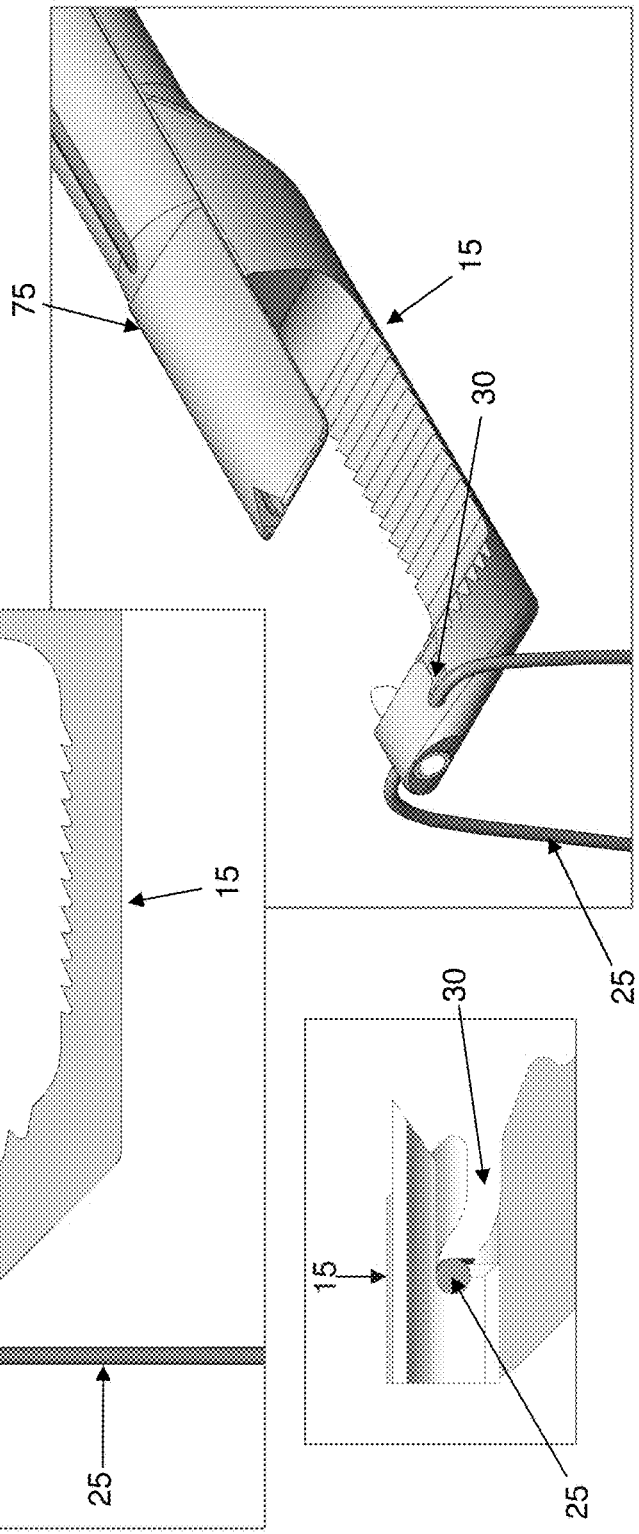
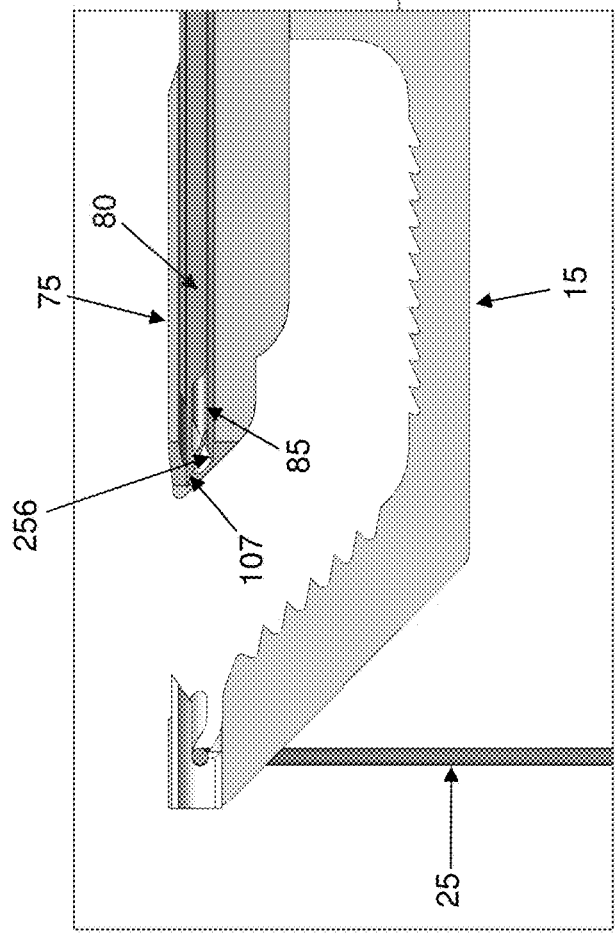

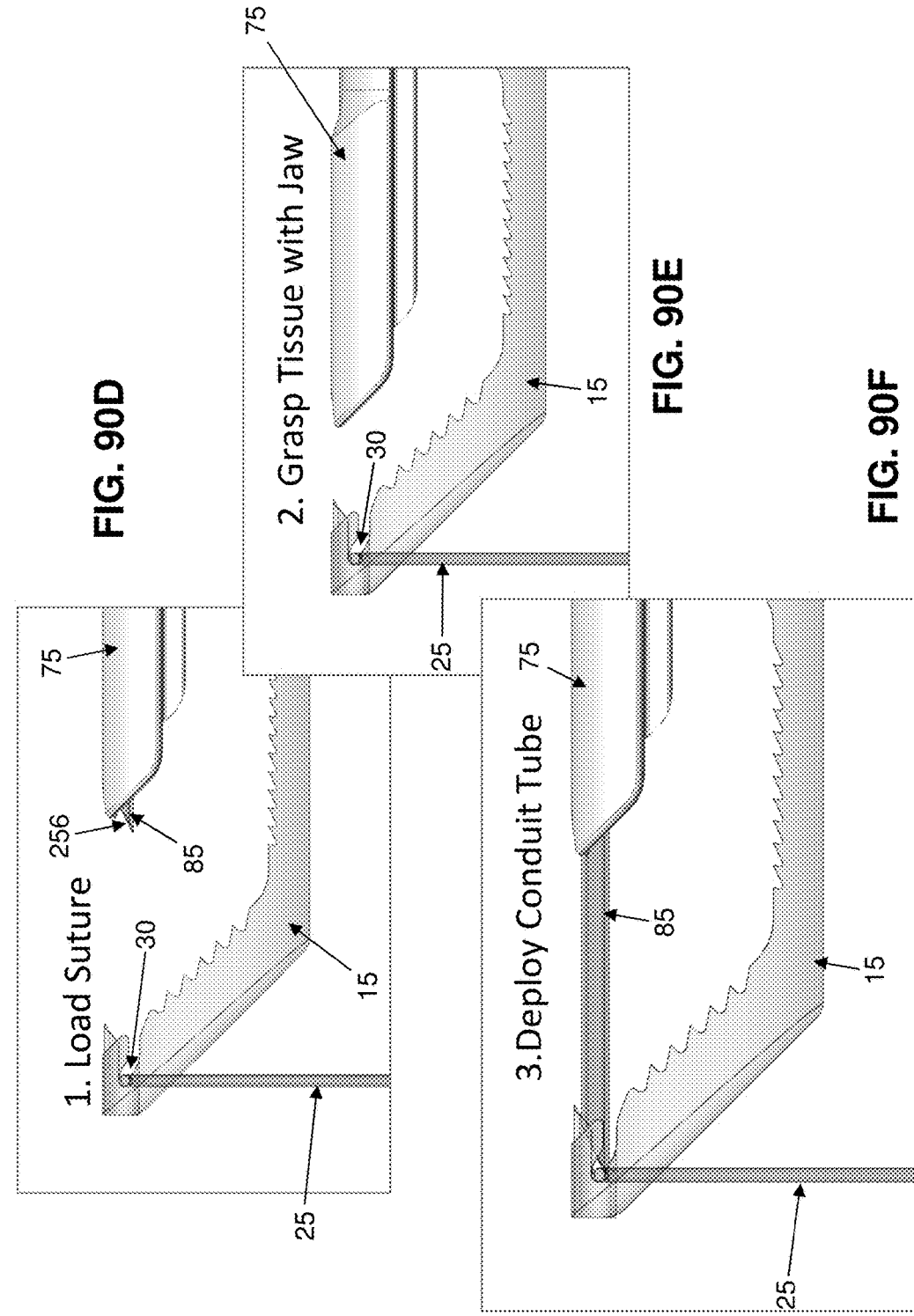

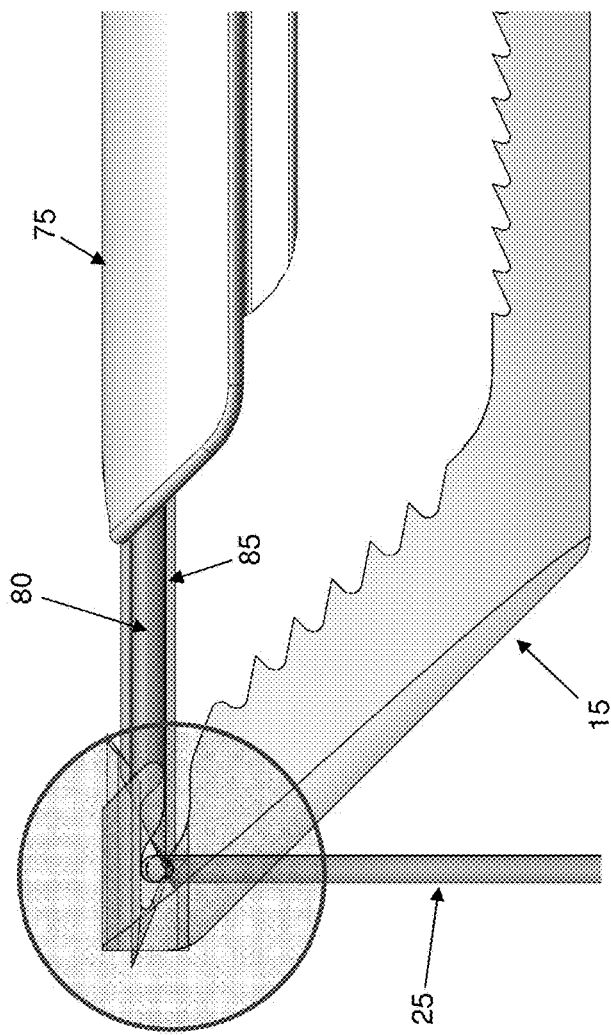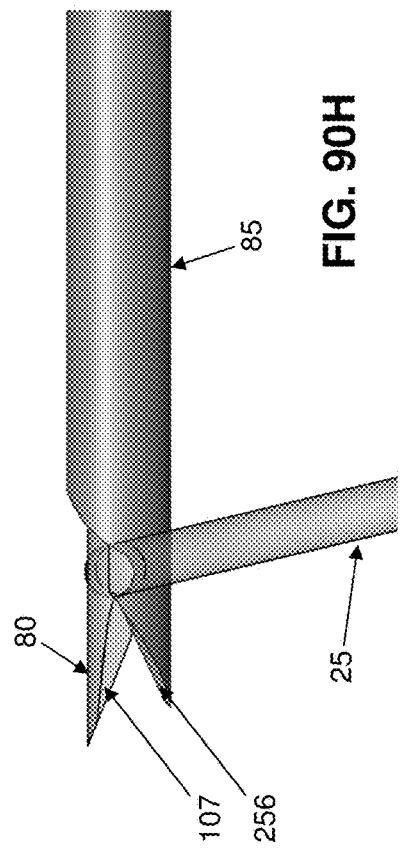

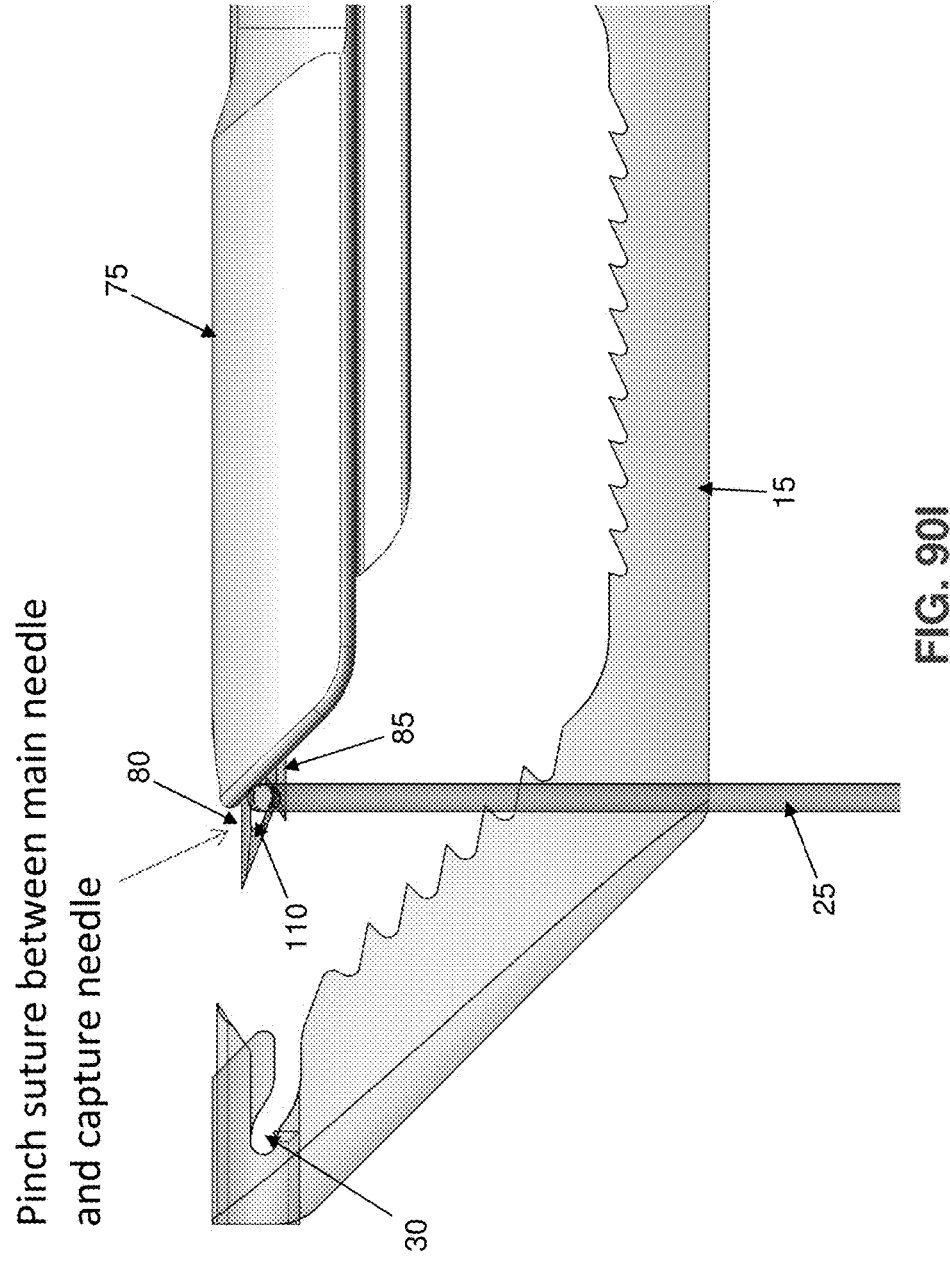

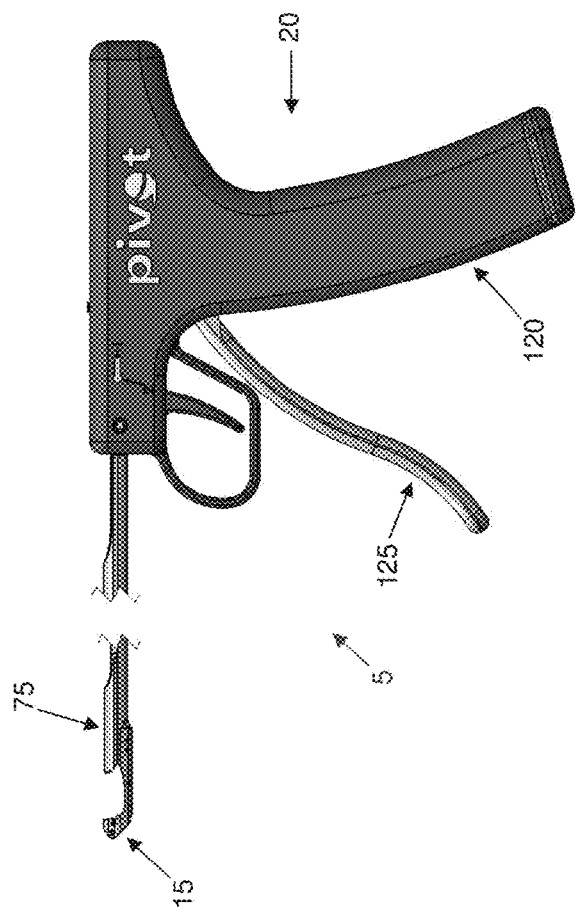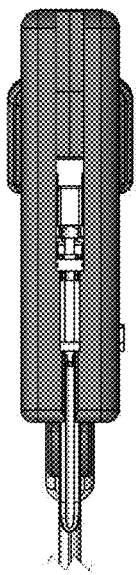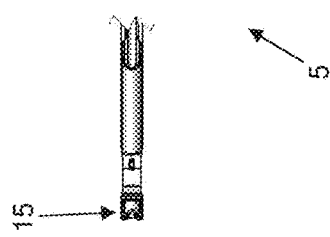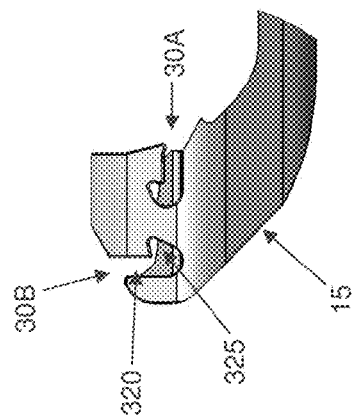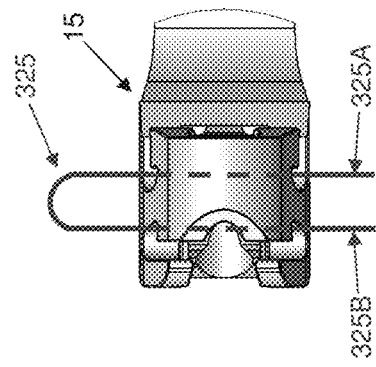
FIG. 98
FIG. 100
FIG. 99
FIG. 101

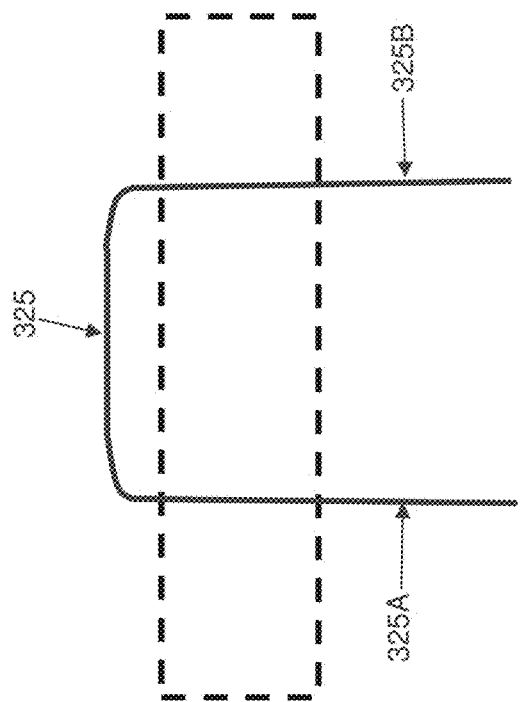

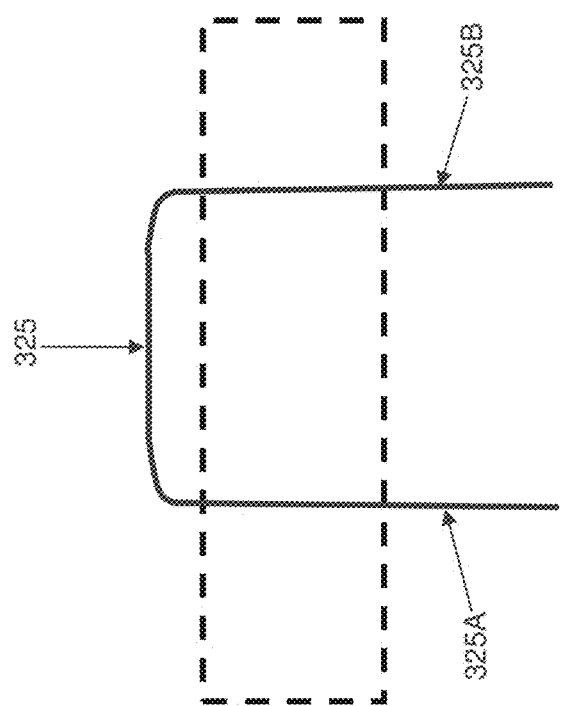

METHOD AND APPARATUS FOR TREATING A HIP JOINT, INCLUDING THE PROVISION AND USE OF A NOVEL SUTURE PASSER

REFERENCE TO PENDING PRIOR PATENT APPLICATIONS

This patent application is a continuation of pending prior U.S. patent application Ser. No. 14/955,451, filed Dec. 1, 2015 by Pivot Medical, Inc. for METHOD AND APPARATUS FOR TREATING A HIP JOINT, INCLUDING THE PROVISION AND USE OF A NOVEL SUTURE PASSER, which patent application is a continuation of prior U.S. patent application Ser. No. 13/564,087, filed Aug. 1, 2012 by David Skinlo et al. for METHOD AND APPARATUS FOR TREATING A HIP JOINT, INCLUDING THE PROVISION AND USE OF A NOVEL SUTURE PASSER, which patent application:

(i) is a continuation-in-part of prior U.S. patent application Ser. No. 12/831,937, filed Jul. 7, 2010 by David Skinlo et al. for METHOD AND APPARATUS FOR TREATING A HIP JOINT, INCLUDING THE PROVISION AND USE OF A NOVEL SUTURE PASSER, which patent application claims benefit of: (a) prior U.S. Provisional Patent Application Ser. No. 61/270,985, filed Jul. 15, 2009 by Scott Heneveld et al. for METHOD AND APPARATUS FOR ACCESSING THE INTERIOR OF A HIP JOINT, INCLUDING THE PROVISION AND USE OF A NOVEL DOUBLE SUTURE PASSER; and (b) prior U.S. Provisional Patent Application Ser. No. 61/327,431, filed Apr. 23, 2010 by David Skinlo et al. for METHOD AND APPARATUS FOR ACCESSING THE INTERIOR OF A HIP JOINT, INCLUDING THE PROVISION AND USE OF A NOVEL SUTURE PASSER; and (ii) claims benefit of prior U.S. Provisional Patent Application Ser. No. 61/513,869, filed Aug. 1, 2011 by David Skinlo et al. for METHOD AND APPARATUS FOR TREATING A HIP JOINT, INCLUDING THE PROVISION AND USE OF A NOVEL SUTURE PASSER.

The six (6) above-identified patent applications are hereby incorporated herein by reference.

FIELD OF THE INVENTION

This invention relates to surgical methods and apparatus in general, and more particularly to surgical methods and apparatus for treating a hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the torso. More particularly, and looking now at FIG. 2, the head of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require large incisions into the interior of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

The Fibrous Capsule

As noted above, a fibrous capsule extends between the neck of the femur and the rim of the acetabular cup, effectively sealing off the ball-and-socket elements of the hip joint from the remainder of the body.

While the fibrous capsule provides an important function in encapsulating the hip joint, it also presents a significant obstacle to arthroscopically treating pathologies of the hip joint. More particularly, the fibrous capsule presents a tough physical barrier which must be penetrated in order to arthroscopically access the interior of the hip joint. However, the penetration of this tough physical barrier must be effected very carefully, since the anatomical structures which are located immediately below the fibrous capsule are frequently delicate and sensitive to damage.

In addition to the foregoing, the fibrous capsule generally sits in close proximity to the underlying bone. As a result, the workspace located between the fibrous capsule and the underlying bone is typically quite limited, thereby presenting significant visualization and operational challenges to the surgeon.

By way of example but not limitation, arthroscopic treatment of cam-type femoroacetabular impingement (i.e., cam-type FAI) is significantly complicated by the limited workspace present within the fibrous capsule. More particularly, cam-type FAI is generally caused by irregular overgrowths in the geometry of the femur. Treatment of cam-type FAI generally calls for debridement of these femoral overgrowths using a burr or other debridement tool. However, the lack of workspace between the overlying fibrous capsule and the underlying femur can make such debridement procedures technically challenging for even the most experienced surgeons, because it can severely limit the field of vision within the workspace and inhibit proper positioning of the burr.

As a result, there is a pressing need for an improved method and apparatus for increasing the workspace around the femur during an arthroscopic hip procedure.

Capsule Release and Subsequent Re-Stitching

It has been recognized that the workspace around the top end of the femur can be significantly increased during an arthroscopic procedure if the fibrous capsule can be laid open at the start of the arthroscopic procedure and then, at the conclusion of the procedure, the fibrous capsule restored, e.g., by suturing.

More particularly, it has been recognized that an arthroscopic procedure can be performed on the hip joint by (i) creating one or more access portals from the surface of the skin down to the fibrous capsule; (ii) opening the fibrous capsule so as to expose the underlying joint; (iii) performing the desired therapeutic procedure on the underlying joint (e.g., debridement of a femoral overgrowth so as to treat a cam-type FAI); and (iv) restoring the fibrous capsule at the conclusion of the procedure by suturing closed the laid-open capsule.

However, heretofore, it has been technically challenging to arthroscopically suture closed the laid-open fibrous capsule at the conclusion of the therapeutic procedure. This is largely because (i) the workspace present at the remote surgical site is quite limited, and (ii) the fibrous capsule is made up of unusually tough tissue, which can make it extremely difficult to arthroscopically pass suture through the fibrous capsule in the suturing operation.

Thus there is a need for a new method and apparatus for passing suture through the fibrous capsule in a suturing operation, thereby making it more practical for a surgeon to arthroscopically operate on the hip joint by first laying open the fibrous capsule, performing the desired procedure on the hip joint, and then closing the fibrous capsule by suturing at the conclusion of the procedure.

SUMMARY OF THE INVENTION

The present invention provides a novel method and apparatus for passing suture through the fibrous capsule in a suturing operation, thereby making it more practical for a surgeon to arthroscopically operate on the hip joint by first laying open the fibrous capsule, performing the desired procedure on the hip joint, and then closing the fibrous capsule by suturing at the conclusion of the procedure.

In one form of the invention, there is provided a suture passer comprising:
 a shaft having an axis;
 a first jaw mounted to the shaft in alignment with the axis, the first jaw being configured to releasably support a length of suture thereon;
 a second jaw movably mounted to the shaft; and
 a needle movably mounted to the shaft, the needle having a hook and being configured to reciprocate in alignment with the axis so that the hook can selectively pass by the second jaw and engage suture releasably supported on the first jaw;
 wherein the first jaw comprises a spring for selectively binding the suture to the first jaw, and further wherein the spring comprises a recess for receiving the suture therein.

In another form of the invention, there is provided a suture passer comprising:
 a shaft having an axis;
 a first jaw mounted to the shaft in alignment with the axis, the first jaw being configured to releasably support a length of suture thereon;
 a second jaw movably mounted to the shaft; and
 a needle movably mounted to the shaft, the needle having a hook and being configured to reciprocate in alignment with the axis so that the hook can selectively pass by the second jaw and engage suture releasably supported on the first jaw;
 wherein at least one of the first jaw and the shaft comprises vacuum means for drawing tissue into the space between the first jaw and the second jaw.

In another form of the invention, there is provided a suture passer comprising:
 a shaft having an axis;
 a first jaw mounted to the shaft in alignment with the axis, the first jaw being configured to releasably support first and second lengths of suture thereon;
 a second jaw movably mounted to the shaft; and
 a needle movably mounted to the shaft, the needle having a hook and being configured to reciprocate in alignment with the axis so that the hook can selectively pass by the second jaw and engage a suture length releasably supported on the first jaw.

In another form of the invention, there is provided a needle assembly for use in a suture passer, the needle assembly comprising an inner needle having a hook thereon, and an outer needle concentrically disposed about the inner needle, the inner needle being spring mounted to the outer needle, wherein the needle assembly further comprises a tab mounted to the proximal end of the needle, the tab having crush ribs formed thereon.

In another form of the invention, there is provided a method for passing suture through tissue, the method comprising:
 releasably supporting a length of suture on a first jaw by binding the suture to the first jaw with a spring, wherein the spring comprises a recess for receiving the suture therein;

advancing a second jaw toward the first jaw so as to releasably clamp tissue therebetween;

advancing a needle through the tissue so that a hook on the needle engages the suture releasably supported on the first jaw; and retracting the needle back through the tissue, with the needle carrying the suture therewith.

In another form of the invention, there is provided a method for passing suture through tissue, the method comprising:

providing a suture passer, the suture passer comprising:
a shaft having an axis;
a first jaw mounted to the shaft in alignment with the axis, the first jaw being configured to releasably support a length of suture thereon;
a second jaw movably mounted to the shaft; and
a needle movably mounted to the shaft, the needle having a hook and being configured to reciprocate in alignment with the axis so that the hook can selectively pass by the second jaw and engage suture releasably supported on the first jaw;
wherein at least one of the first jaw and the shaft comprises vacuum means for drawing tissue into the space between the first jaw and the second jaw;
applying suction to the vacuum means, and moving the suture passer adjacent to the tissue which is to have the suture passed therethrough, such that the tissue to be sutured is disposed between the first jaw and the second jaw;
clamping the tissue between the first jaw and the second jaw; and
passing the suture through the tissue with the needle.

In another form of the invention, there is provided a method for passing suture through tissue, the method comprising:

providing a suture passer comprising:
a shaft having an axis;
a first jaw mounted to the shaft in alignment with the axis, the first jaw releasably supporting first and second lengths of suture thereon;
a second jaw movably mounted to the shaft; and
a needle movably mounted to the shaft, the needle having a hook and being configured to reciprocate in alignment with the axis so that the hook can selectively pass by the second jaw and engage a suture length releasably supported on the first jaw;
positioning the suture passer adjacent tissue;
using the needle to pass the first length of suture through tissue;
moving the suture passer relative to the tissue; and
using the needle to pass the second length of suture through the tissue.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (i.e., cam-type FAI);

FIG. 14 is a schematic view showing pincer-type femoroacetabular impingement (i.e., pincer-type FAI);

FIGS. 18-38 are schematic views showing various details of the construction and operation of the distal end of the novel suture passer of FIGS. 16 and 17;

FIGS. 41-46, 46A and 47-50 are schematic views showing various details of the construction and operation of the reusable tool assembly and a disposable needle assembly of FIGS. 39 and 40;

FIGS. 50A, 50B and 50C are schematic views showing an alternative form of the distal jaw spring of the novel suture passer of FIGS. 16 and 17;

FIGS. 55-68 are schematic views showing various details of the construction and operation of the distal end of an alternative form of the novel suture passer of the present invention;

FIGS. 90A, 90B and 90C are schematic views showing an alternative form of the novel suture passer of the present invention;

FIGS. 90D, 90E, 90F, 90G, 90H and 90I are schematic views showing the novel suture passer of FIGS. 90A, 90B and 90C being used to pass suture;

FIGS. 98-101 are schematic views showing another alternative construction for the novel suture passer of the present invention;

FIGS. 102-110 are schematic views showing a suture passing operation being effected using the novel suture passer of FIGS. 98-101; and FIGS. 111-119 are schematic views showing another suture passing operation being effected using the novel suture passer of FIGS. 98-101.

DETAILED DESCRIPTION OF THE INVENTION

Figure 1A:
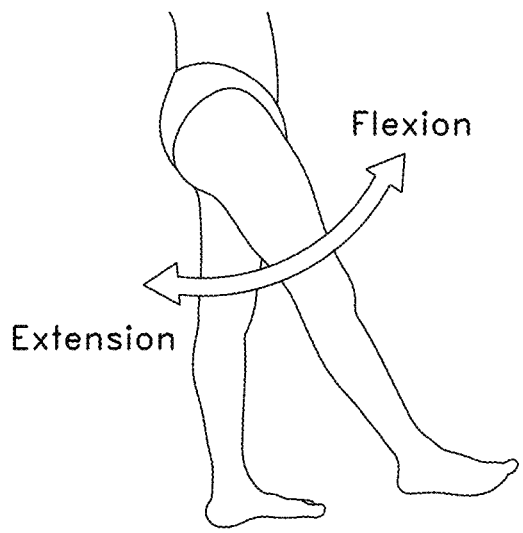
FIGS. 1A-1D are schematic views showing various aspects of hip motion.
Figure 1B:
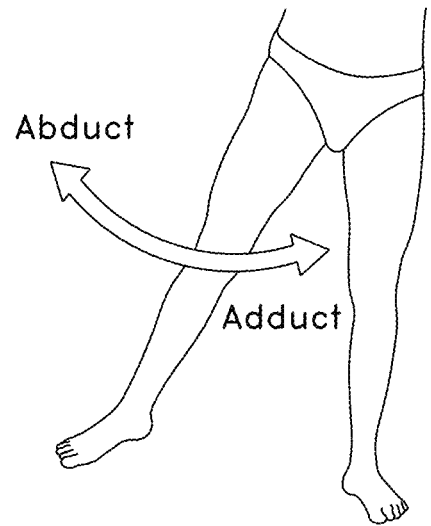
Figure 1C:
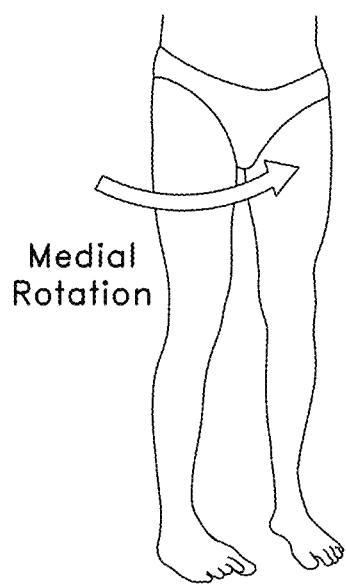
Figure 1D:
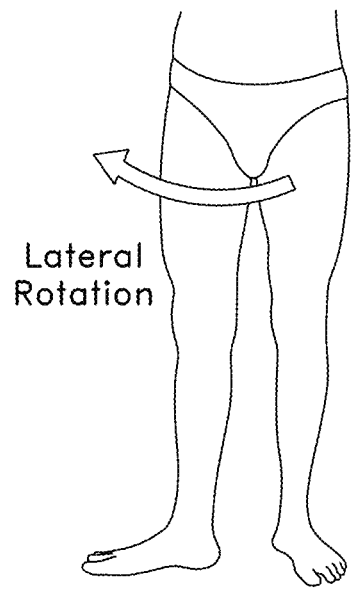
Figure 2:
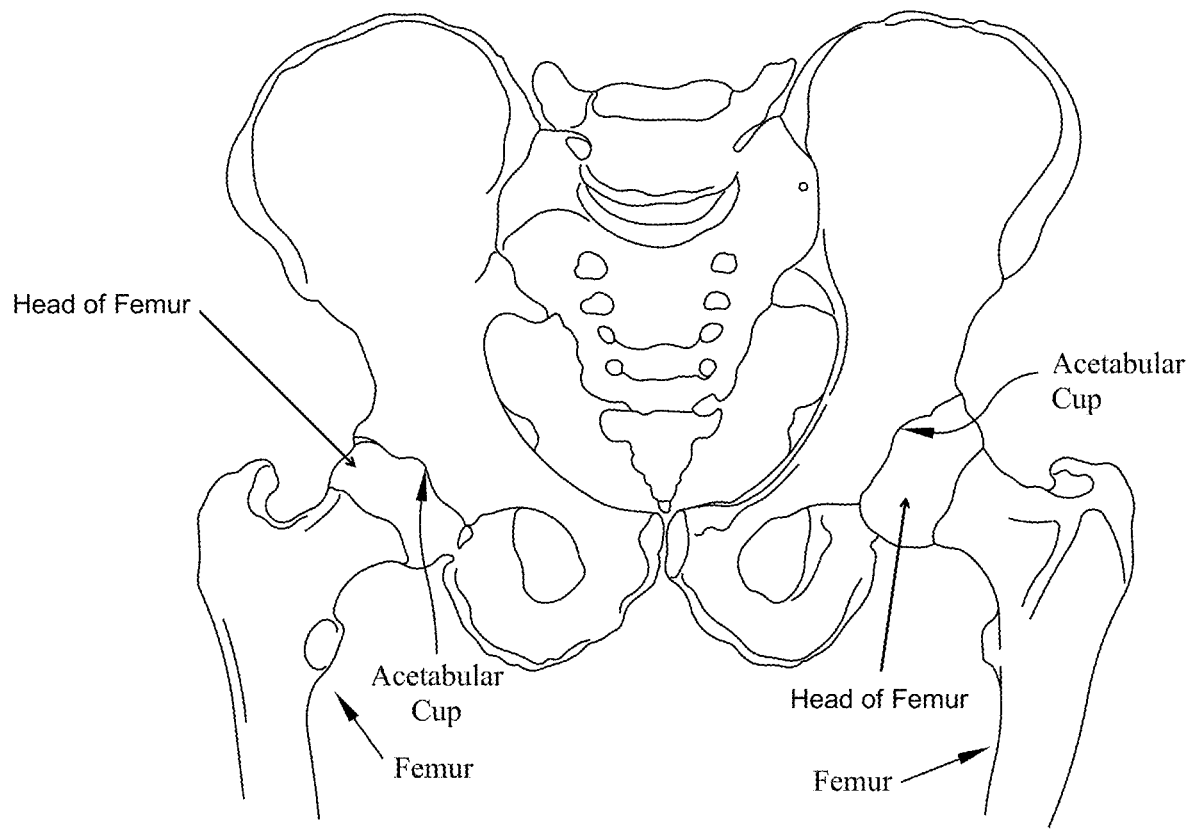
FIG. 2 is a schematic view showing bone structures in the region of the hip joint.
Figure 3:
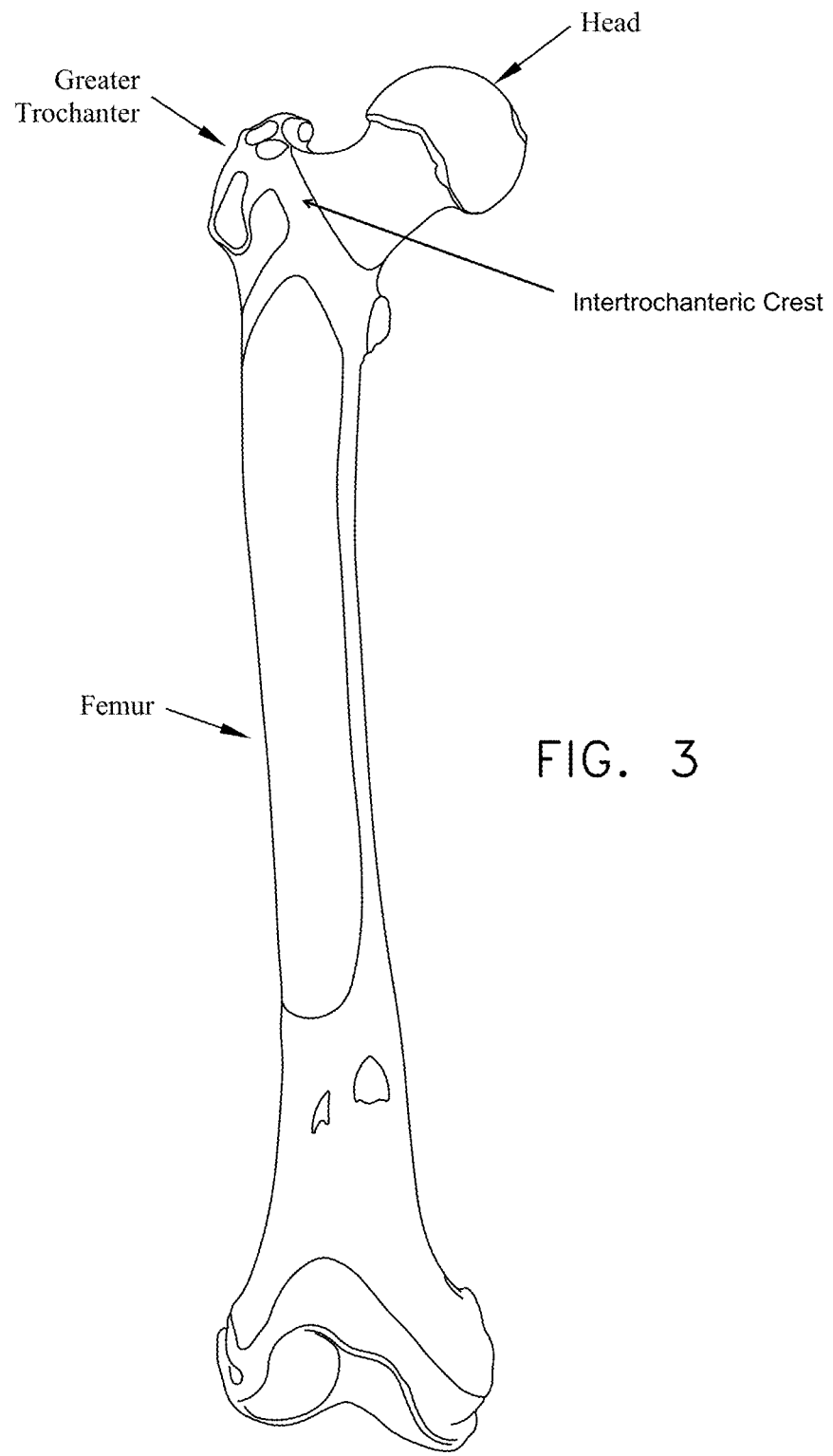
FIG. 3 is a schematic anterior view of the femur.
Figure 4:
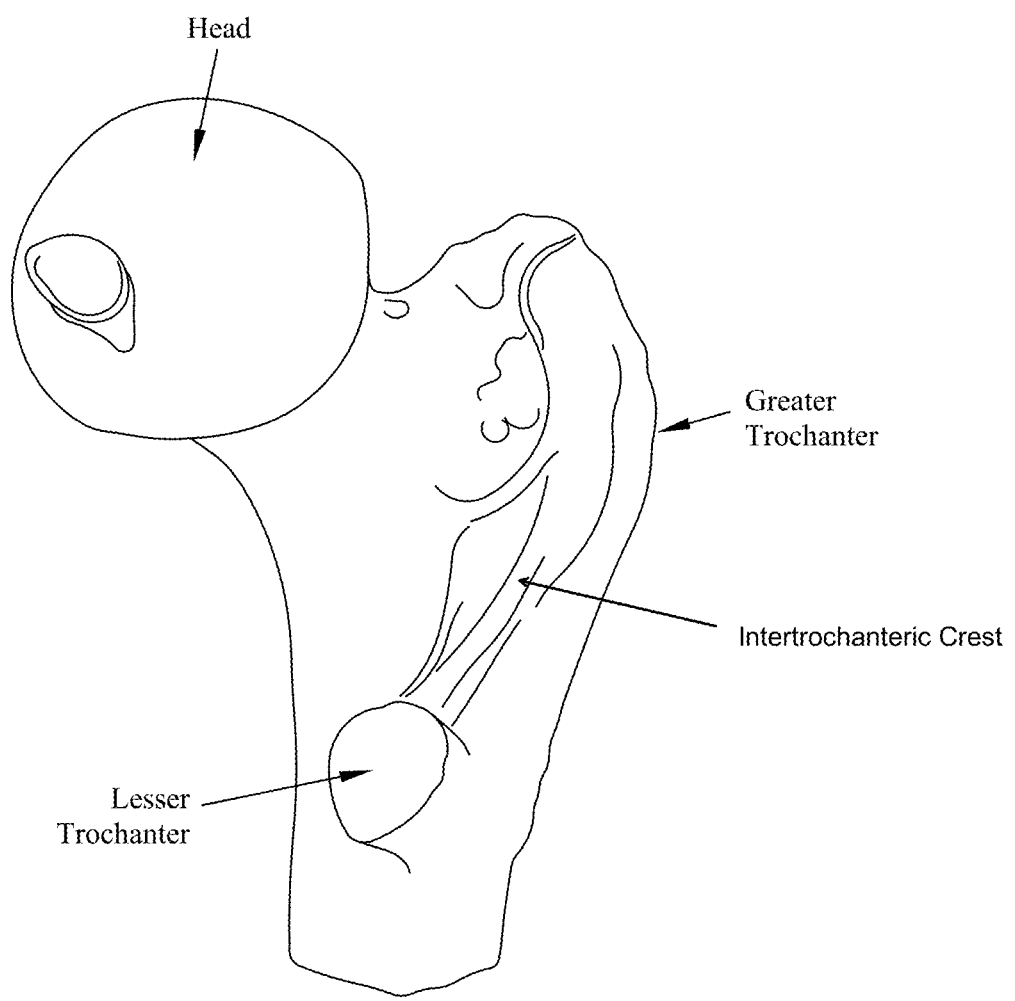
FIG. 4 is a schematic posterior view of the top end of the femur.
Figure 5:
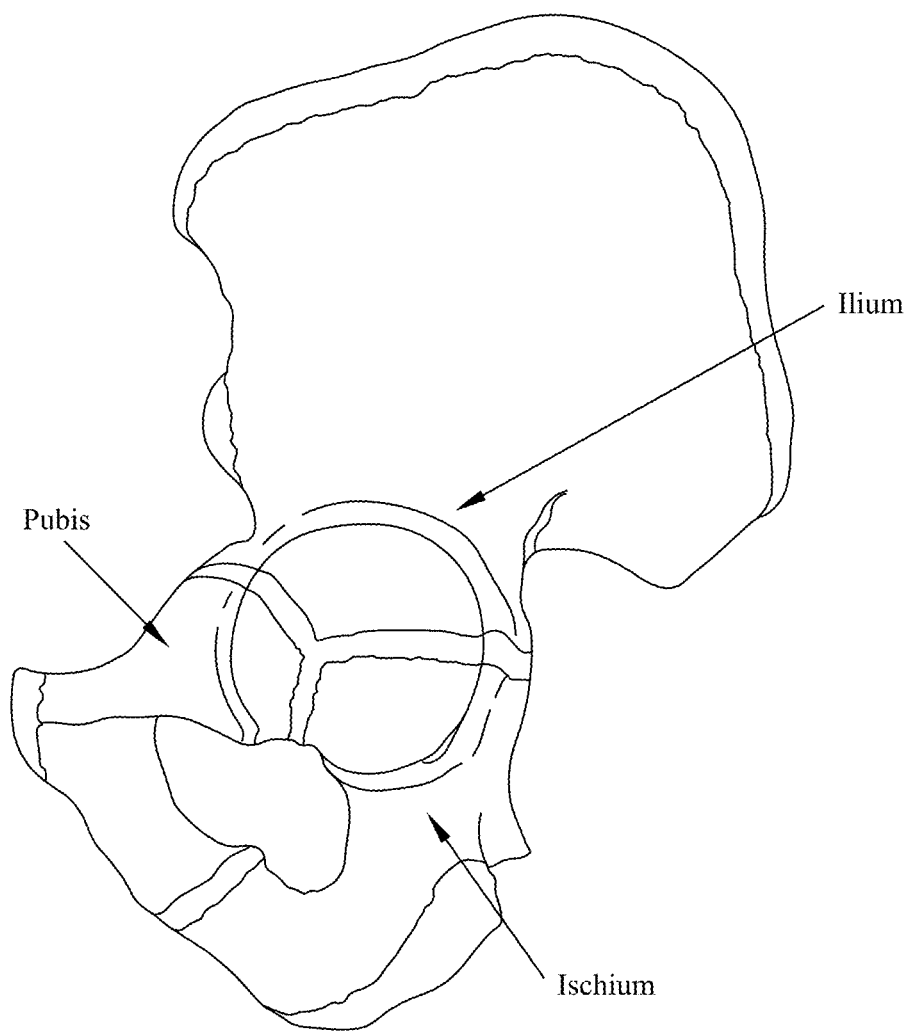
FIG. 5 is a schematic view of the pelvis.
Figure 6:
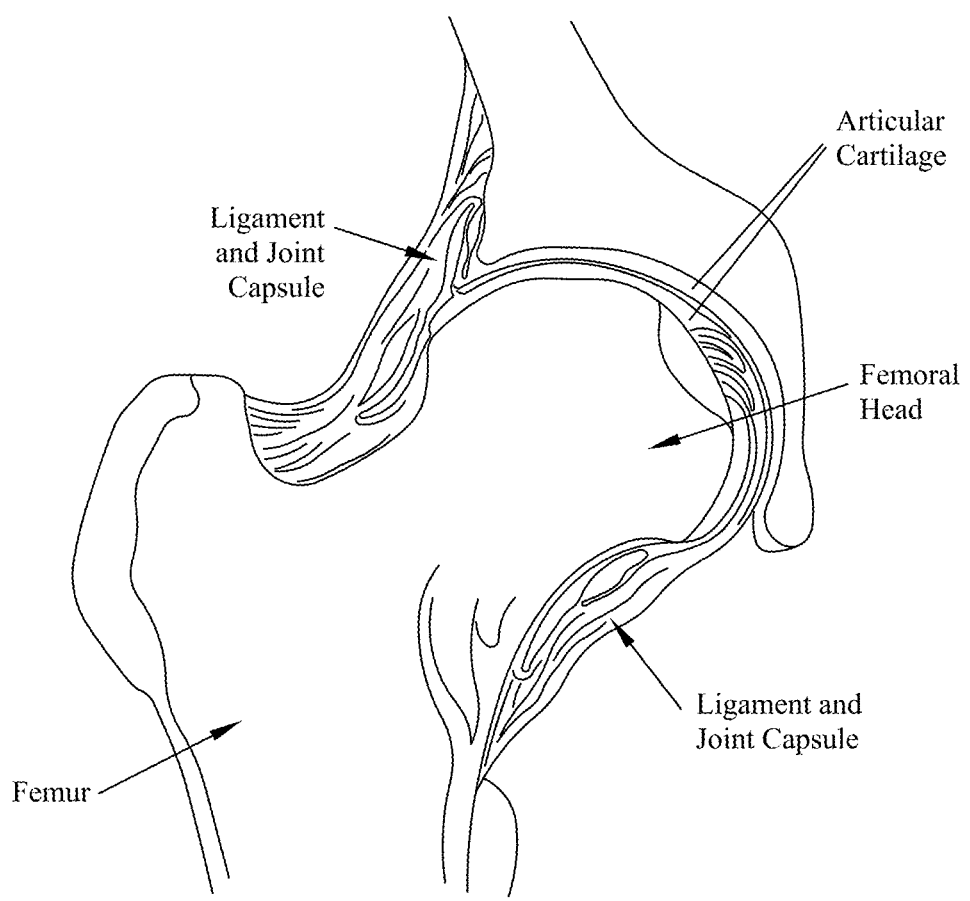
FIGS. 6-12 are schematic views showing bone and soft tissue structures in the region of the hip joint.
Figure 7:
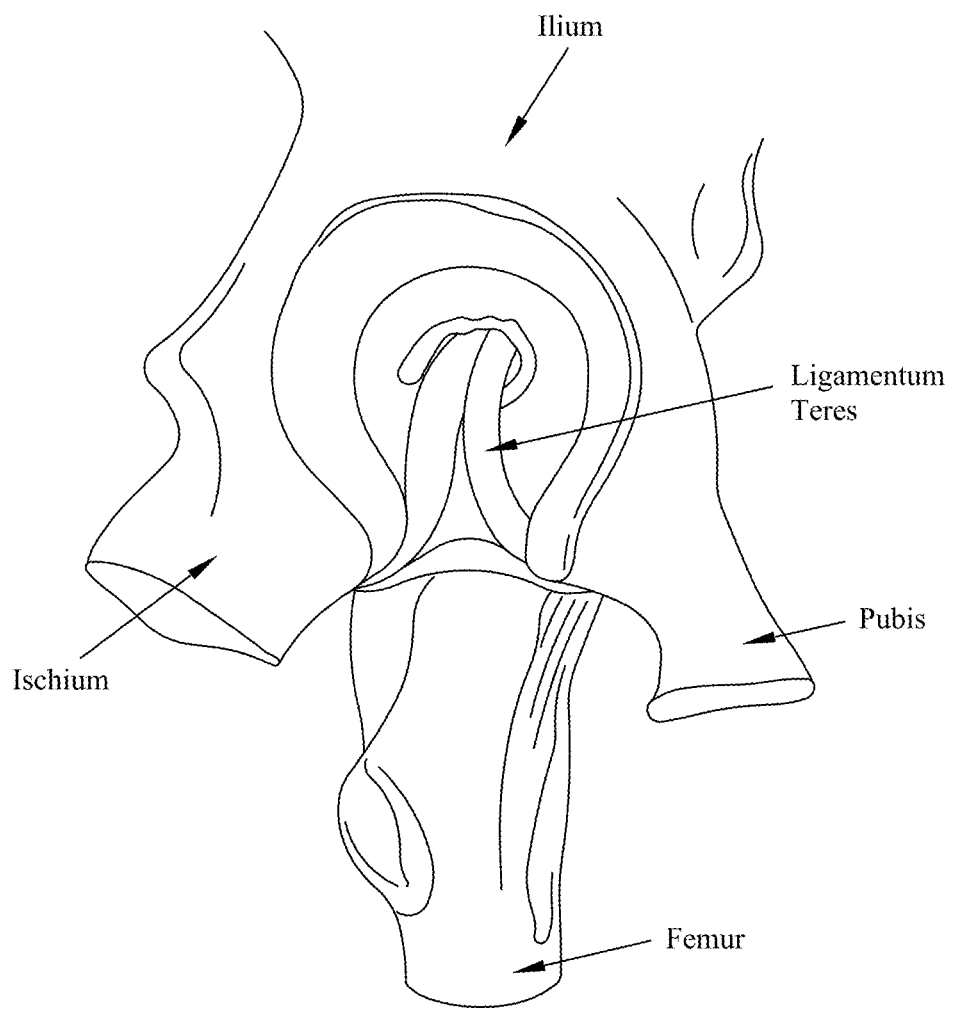
Figure 8:
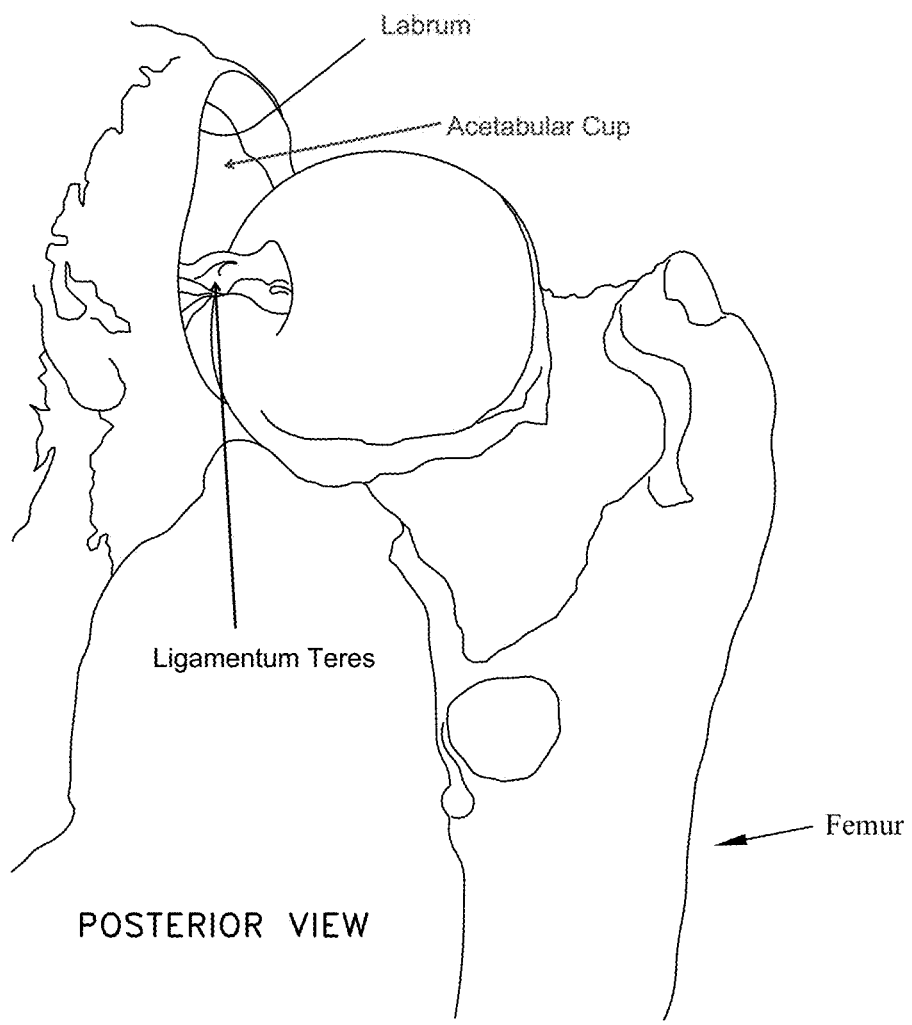
Figure 9:
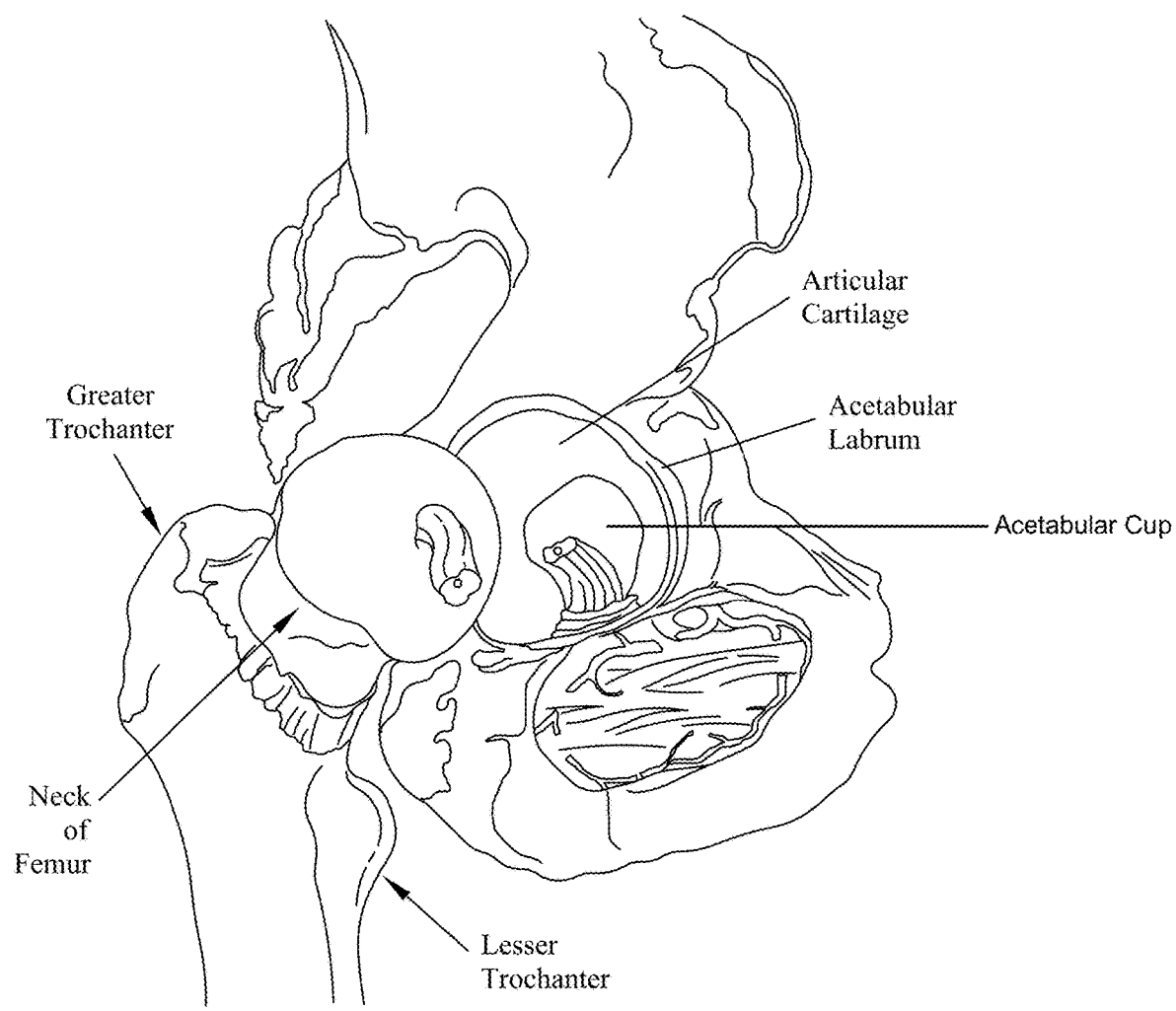
Figure 10:
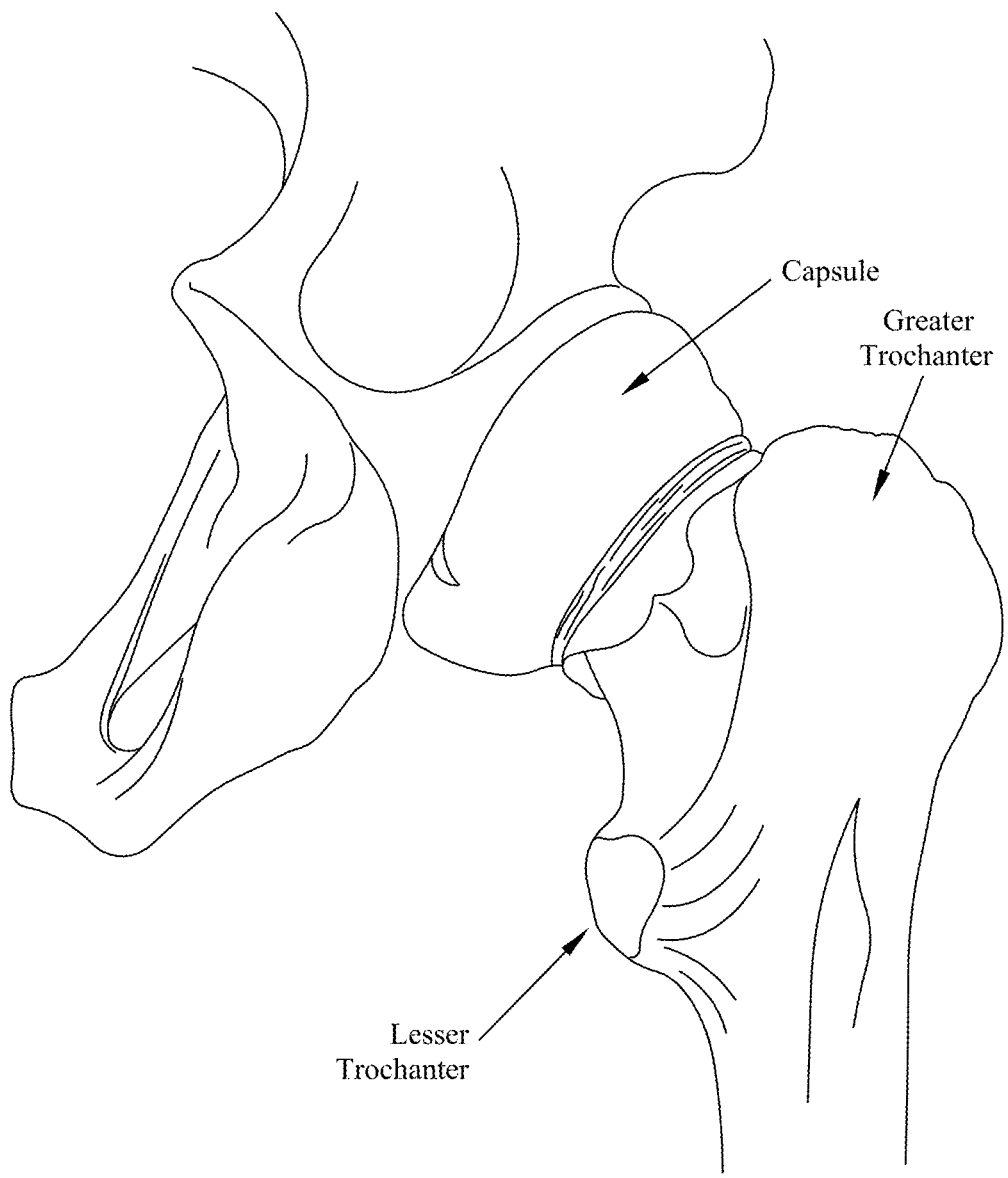
Figure 11:
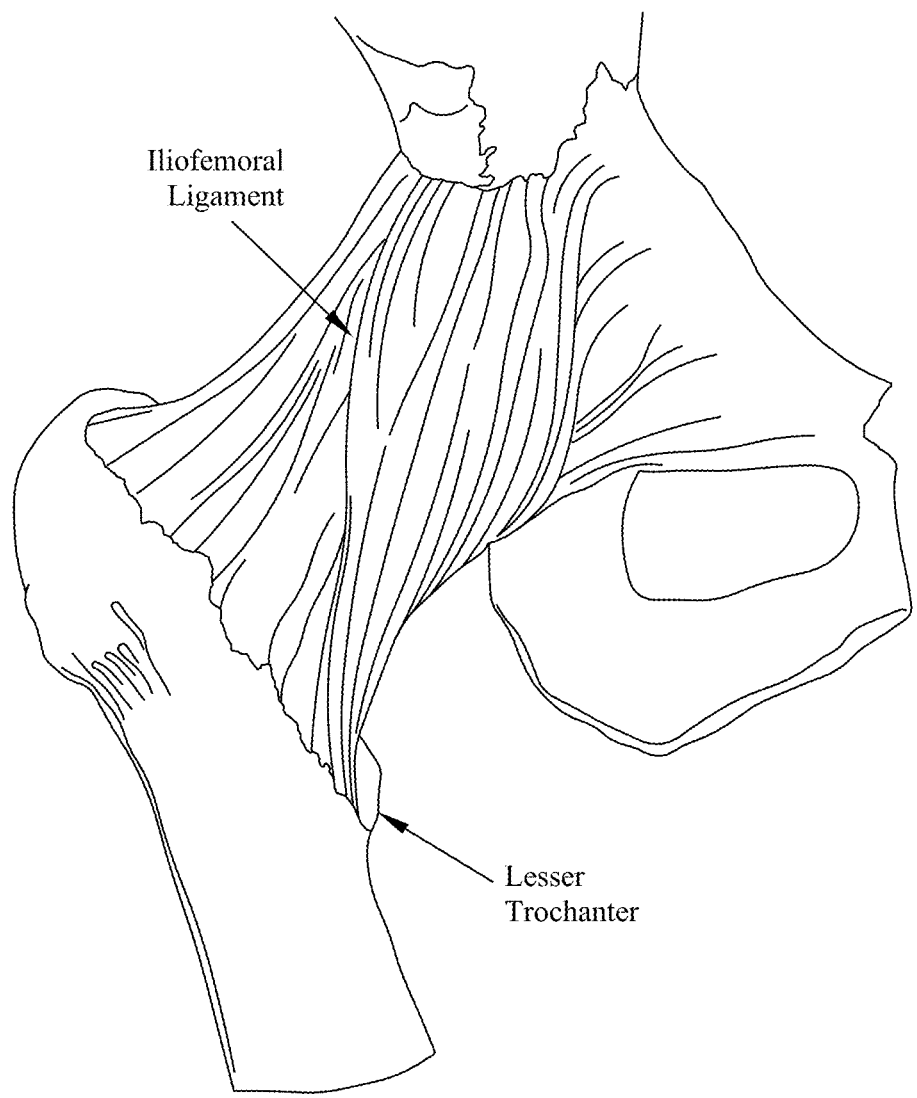
Figure 12:
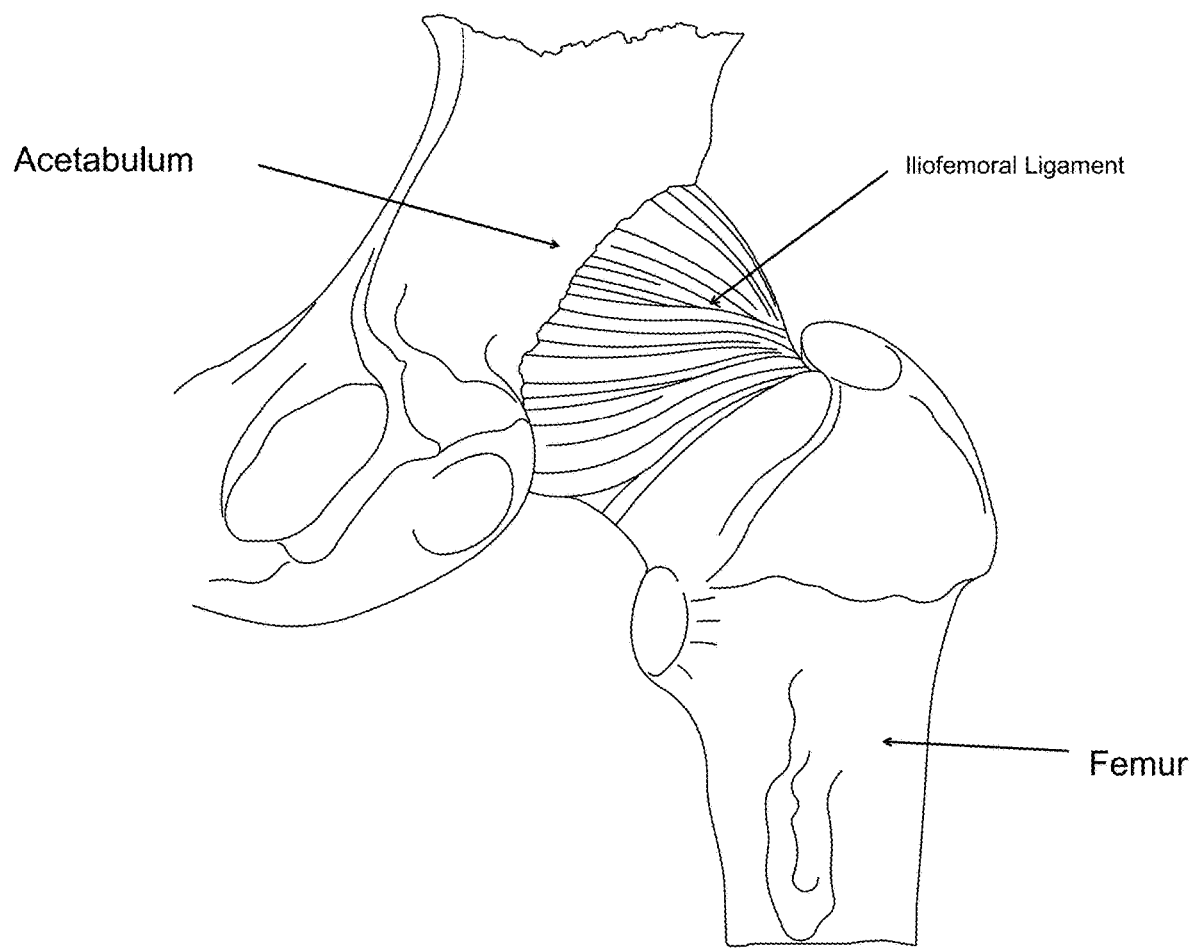
Figure 15:
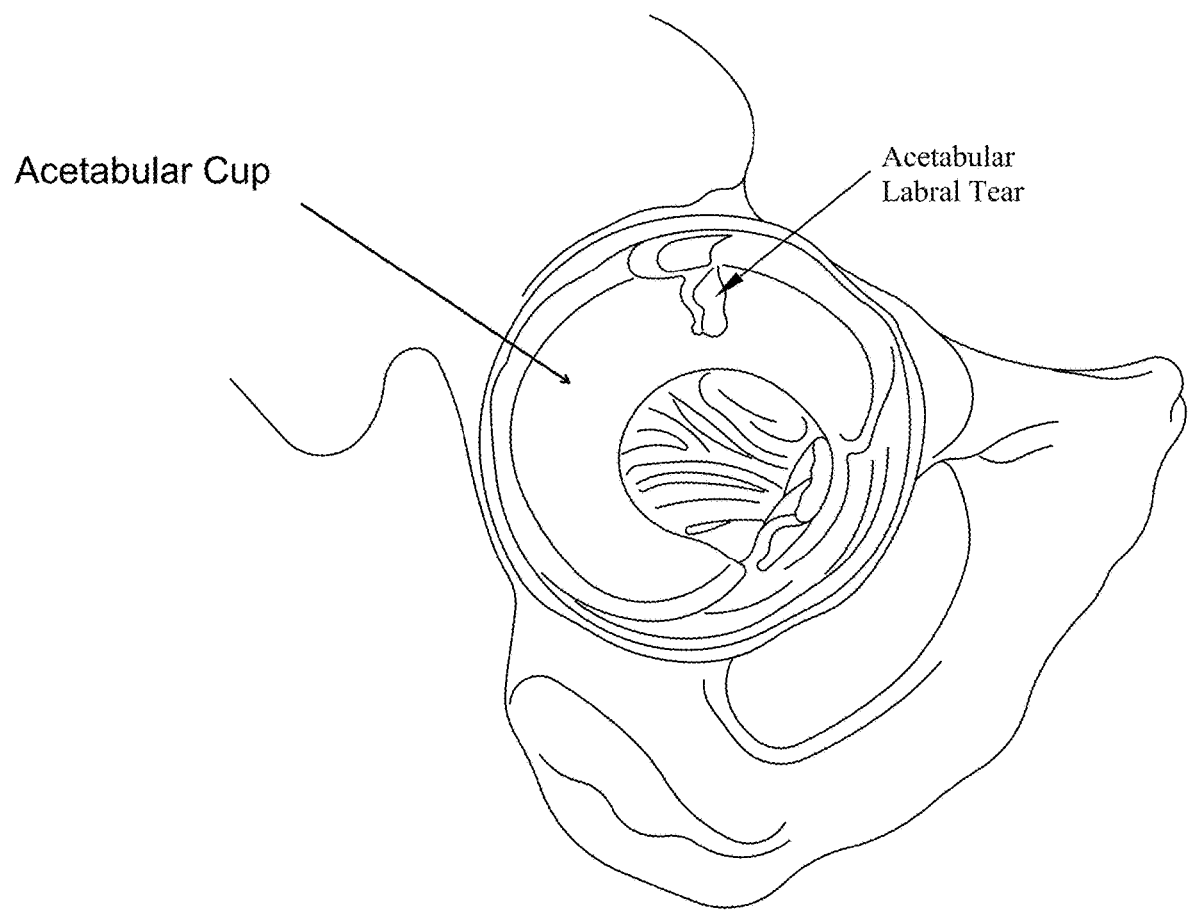
FIG. 15 is a schematic view showing a labral tear.
Figure 17:
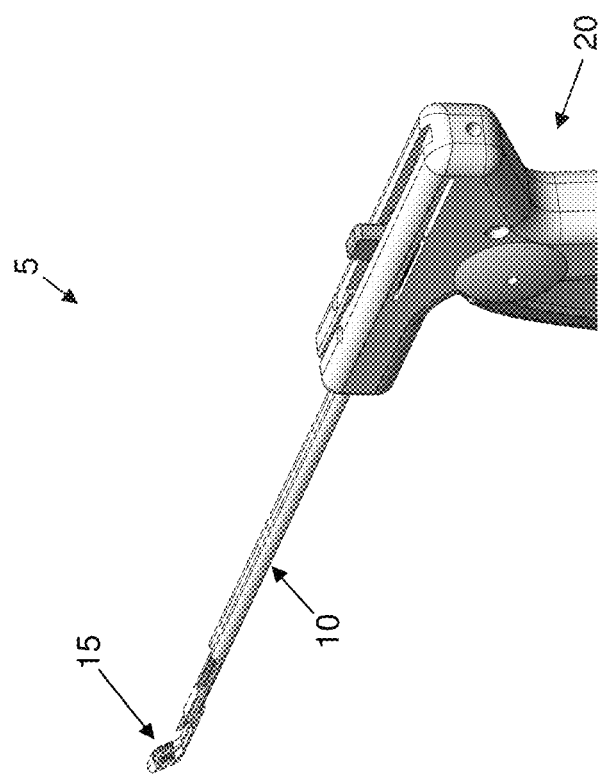
FIGS. 16 and 17 are schematic views showing a novel suture passer formed in accordance with the present invention.
Figure 16:
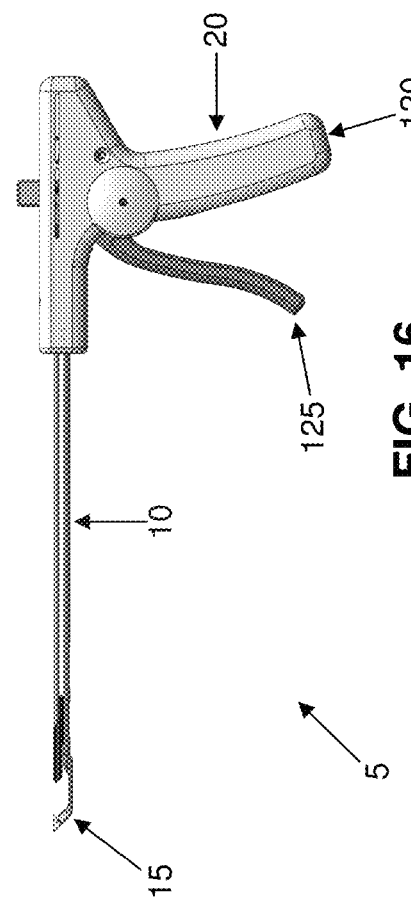

Looking first at FIGS. 16 and 17, there is shown a novel suture passer 5 formed in accordance with the present invention. Suture passer 5 generally comprises an elongated shaft 10 having a distal jaw 15 disposed at the distal end of elongated shaft 10 and a handle 20 disposed at the proximal end of elongated shaft 10.

Looking next at FIGS. 18-25, distal jaw 15 is intended to releasably carry a suture 25 thereon. To this end, and as will hereinafter be discussed in further detail, distal jaw 15 has a suture slot 30 (FIG. 18) formed therein. In one preferred form of the present invention, suture slot 30 is sized so that suture 25 can slide easily therein. And in one preferred form of the present invention, suture slot 30 comprises a proximal longitudinal section 35, an intermediate diagonal section 40, and a distal longitudinal section 45. Distal jaw 15 also includes a slot 50 (FIG. 20) at its distal end. A distal jaw spring 55 (FIG. 19) is movably mounted in slot 50. More particularly, distal jaw spring 55 is mounted to elongated shaft 10 at the proximal end of the distal jaw spring, e.g., via a pair of pins 60 extending through the proximal end of the distal jaw spring, such that the distal end of distal jaw spring 55 can flex downwardly relative to distal jaw 15, in a cantilever fashion. A suture seat 70 (FIG. 25) is disposed at the free end of distal jaw spring 55. Suture seat 70 preferably has an inclined surface 72 thereon to act as a ramp to aid the inner needle 80 (and/or the outer needle 85) (see below) in displacing the distal jaw spring 55 downward during the inner and outer needles' deployment stroke, as will hereinafter be discussed in further detail. Distal jaw spring 55 and suture seat 70 are sized and positioned relative to distal jaw 15 so that suture seat 70 normally protrudes across suture slot 30 under the influence of distal jaw spring 55. However, suture seat 70 can be forced out of suture slot 30 by overcoming the bias of distal jaw spring 55, e.g., by camming, as will hereinafter be discussed. As a result of this construction, a suture 25 disposed in suture slot 30 can be releasably held in the suture slot 30 (and hence releasably held to distal jaw 15) with a light friction fit by distal jaw spring 55 and suture seat 70.

Figure 19:
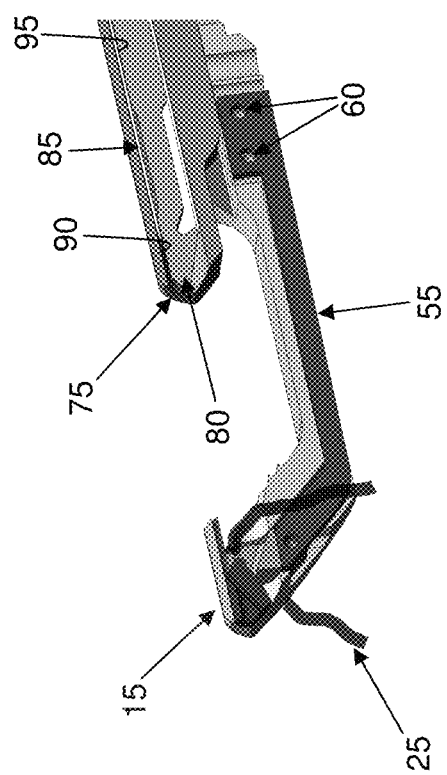
Figure 22:
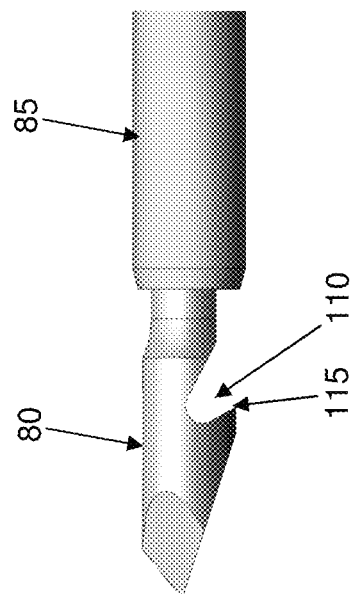
Figure 23:
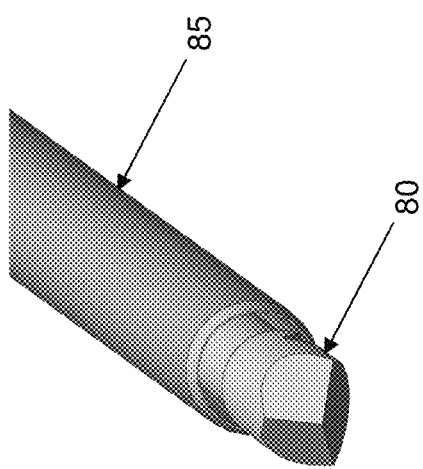
Figure 21:
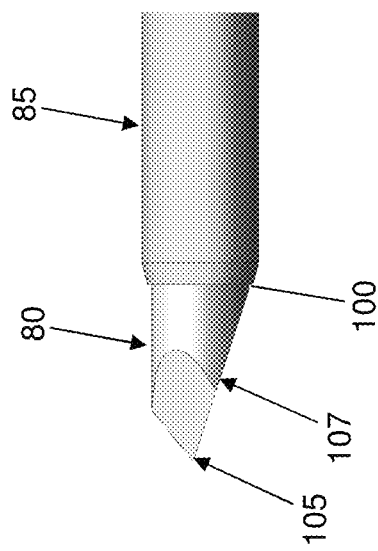

Still looking now at FIGS. 18-25, suture passer 5 also comprises three elements which are movable relative to elongated shaft 10 and distal jaw 15, i.e., a proximal jaw 75, an inner needle 80 and an outer needle 85, with outer needle 85 being disposed co-axial with, and intermediate, inner needle 80 and proximal jaw 75. More particularly, proximal jaw 75 includes a lumen 90 for slidably receiving outer needle 85 and inner needle 80 (FIG. 19). Outer needle 85 comprises a lumen 95 for slidably receiving inner needle 80, and includes a beveled tip 100 (FIG. 21) which closely surrounds inner needle 80 (FIGS. 21-23). Inner needle 80 preferably comprises a sharp distal tip 105, an inclined surface 107 and a suture slot 110. Inclined surface 107 is preferably oriented towards the distal jaw spring 55 to facilitate displacing the distal jaw spring 55 as the distal jaw spring is contacted by the inner needle 80 when the inner needle advances. In other words, inclined surface 107 of inner needle 80 is oriented so that when the advancing inner needle 80 engages distal jaw spring 55, inclined surface 107 cams distal jaw spring 55 downward, out of the way of the advancing inner needle 80. Suture slot 110 is preferably in the form of a "crochet hook", in the sense that it includes a return 115 extending alongside a portion of the suture slot, whereby to provide a "crochet hook" effect for the distal end of inner needle 80.

Returning now to FIGS. 16 and 17, handle 20 preferably includes a grip 120 for seating in the palm of the user's hand, and a trigger 125 for actuation by the user's fingers. Handle 20 is constructed so that, by pulling trigger 125 towards grip 120, and thereafter releasing trigger 125, proximal jaw 75, inner needle 80 and outer needle 85 can be moved in a sequenced manner relative to elongated shaft 10 and distal jaw 15, and in a sequenced manner relative to one another, whereby to pass suture through tissue, as will hereinafter be discussed in further detail. Significantly, due to the construction employed by suture passer 5, suture can be arthroscopically passed through even the tough fibrous capsule of the hip joint, whereby to permit arthroscopic suturing of the fibrous capsule. As a result, the present invention makes it more practical for a surgeon to arthroscopically operate on the hip joint by first laying open the fibrous capsule, performing the desired procedure on the hip joint, and then closing the fibrous capsule by suturing at the conclusion of the procedure.

Suture passer 5 is preferably used as follows.

Figure 18:
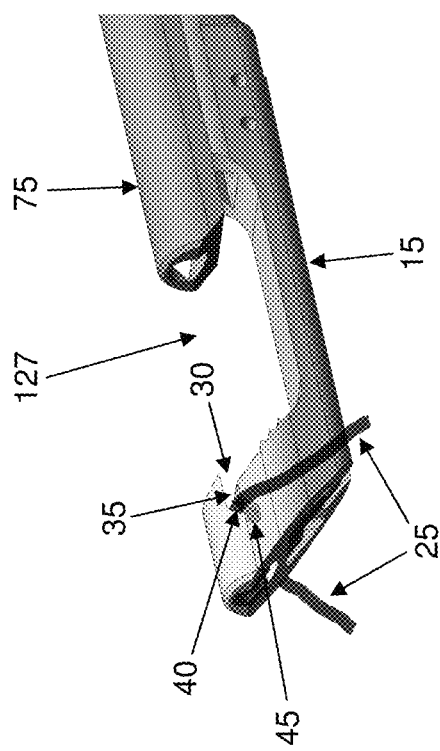
Figure 20:
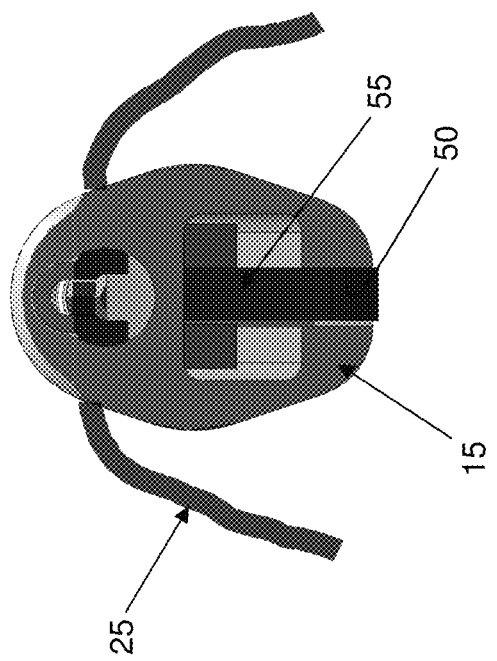

Looking now at FIGS. 18 and 19, proximal jaw 75 is initially retracted proximally relative to distal jaw 15 so as to provide a gap 127 therebetween, inner needle 80 is initially retracted so that its distal end resides within lumen 90 of proximal jaw 75, and outer needle 85 is initially retracted so that its distal end resides proximal to the distal end of inner needle 80. A suture 25 is slipped into suture slot 30 of distal jaw 15 and then pulled distally so that the suture sits at the convergence of proximal longitudinal section 35 and intermediate diagonal section 40 of suture slot 30—this action causes the suture to engage the inclined surface 72 of suture seat 70 (FIG. 25) and thereby drive (i.e., cam) suture seat 70 (and the free end of distal jaw spring 55) downwardly far enough for the suture to slip above suture seat 70, whereupon suture seat 70 (and distal jaw spring 55) press upwardly so as to releasably capture suture 25 in suture slot 30 via the spring-biased suture seat 70.

With suture passer 5 in this condition, the distal end of the suture passer is ready to be advanced to the remote site where tissue is to be sutured. By way of example but not limitation, the distal end of suture passer 5 may be arthroscopically advanced to a laid-open fibrous capsule in the hip joint, in order to suture closed the laid-open fibrous capsule at the conclusion of an arthroscopic procedure. Once the distal end of suture passer 5 is disposed at the remote site, the suture passer is maneuvered so that the tissue which is to be sutured is located in the gap 127 (FIG. 18) between distal jaw 15 and proximal jaw 75. Alternatively, and/or additionally, the tissue which is to be sutured may be maneuvered (e.g., with a supplemental tool) so that the tissue is located in the gap 127 between distal jaw 15 and proximal jaw 75.

Figure 26:
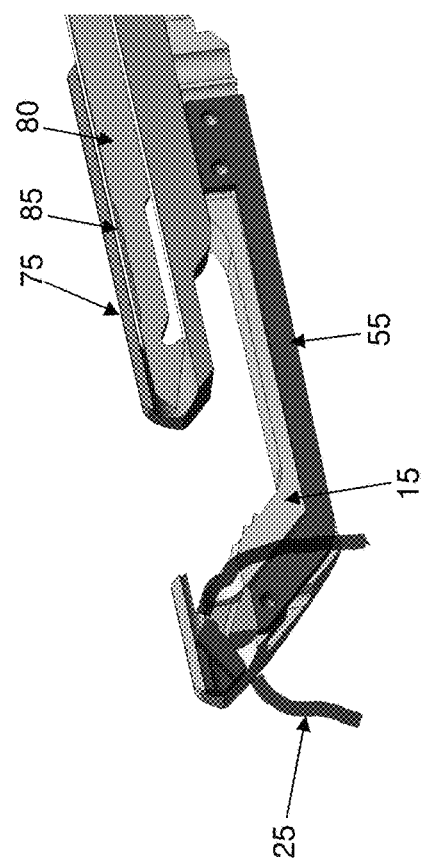
Figure 27:
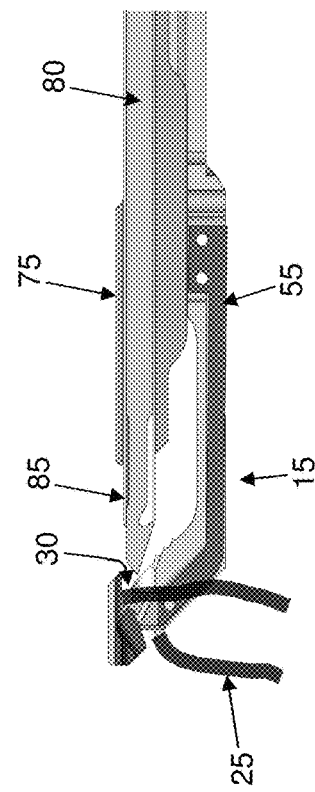

Looking next at FIGS. 26 and 27, proximal jaw 75 is then advanced longitudinally towards distal jaw 15 so as to securely clamp the tissue which is to be sutured between the two jaw members. Preferably inner needle 80 and outer needle 85 are advanced in conjunction with proximal jaw 75, in the manner shown in FIG. 27.

Figure 28:
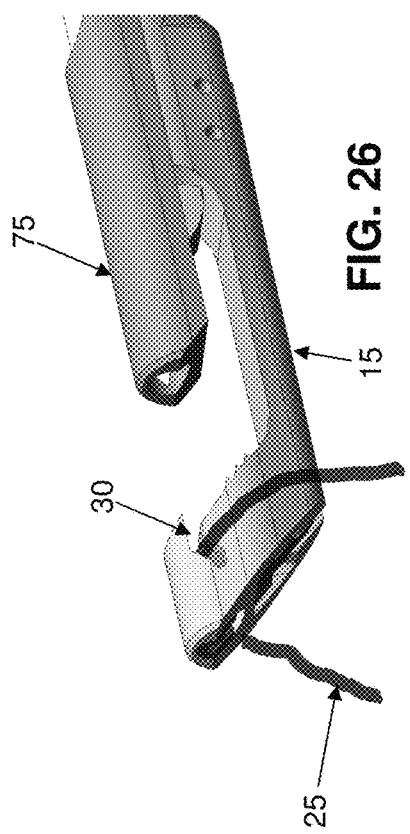
Figure 29:
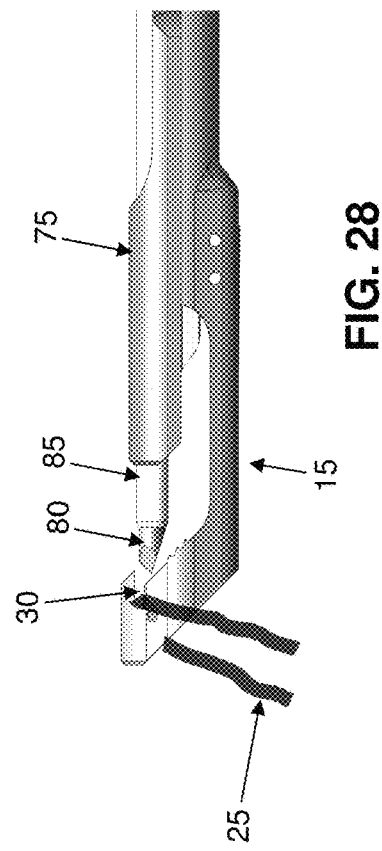
Figure 31:
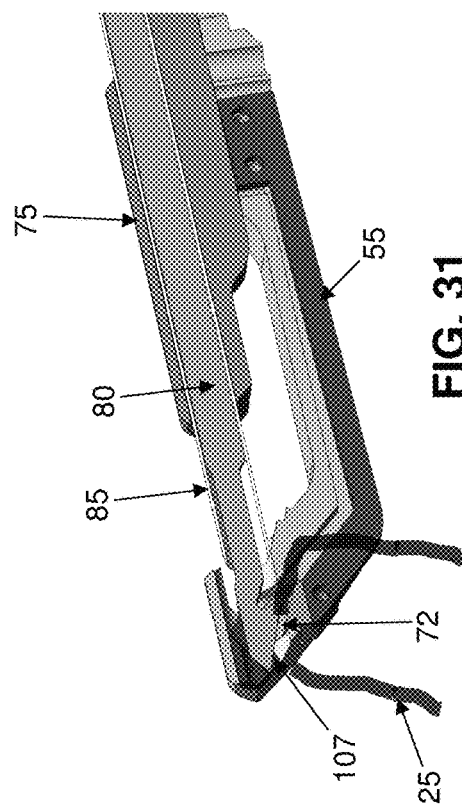
Figure 33:
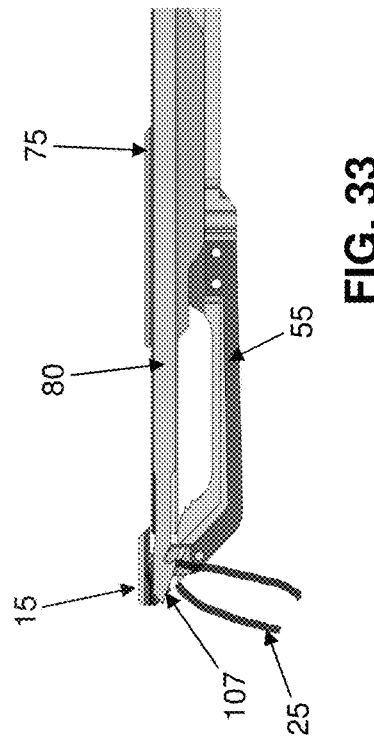
Figure 30:
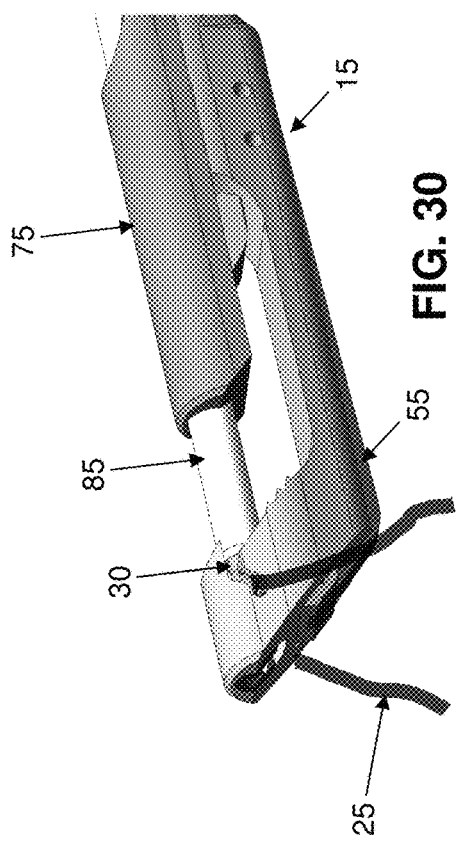
Figure 32:
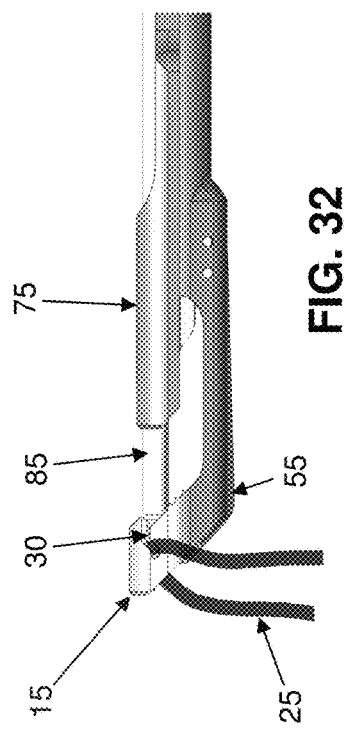

Once the tissue has been securely clamped between distal jaw 15 and proximal jaw 75, inner needle 80 and outer needle 85 are advanced together, as a unit, out of proximal jaw 75 and through the tissue. See FIGS. 28 and 29. As this occurs, outer needle 85 closely supports inner needle 80, and vice-versa, thereby providing increased column strength for the two needles and permitting the two relatively thin needles to pass through tough tissue, e.g., the tough fibrous capsule of the hip. In this respect it should be appreciated that this mutual needle support (for increased column strength) is a very important aspect of the present invention, since it enables the two relatively thin needles to pass through extremely tough tissue (e.g., the fibrous capsule of the hip), tissue which neither needle could easily pass through alone, or which a single needle might pass through alone but not accurately along the desired axis of travel (e.g., the single needle might diverge from a straight path and miss a target zone on the other side of the tissue).

In addition to the foregoing, it should also be appreciated that, significantly, proximal jaw 75 also supports inner needle 80 and outer needle 85 during their passage through tissue, since only short lengths of inner needle 80 and outer needle 85 extend beyond (i.e., out of) proximal jaw 75. Again, this needle-reinforcing construction helps enable the two relatively thin needles to pass through extremely tough tissue (e.g., the fibrous capsule of the hip) which they might not otherwise be able to penetrate on their own, or which they might not otherwise be able to penetrate accurately on their own.

Figure 35:
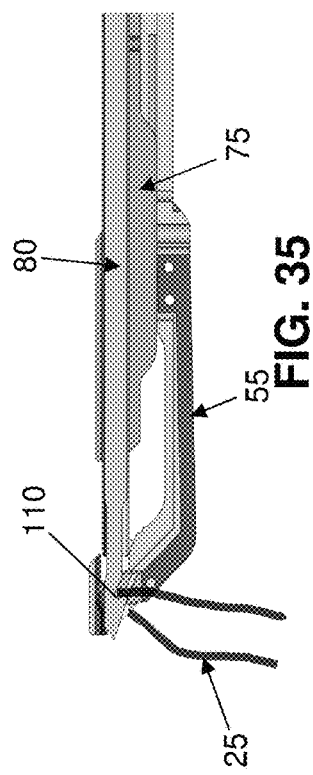
Figure 34:
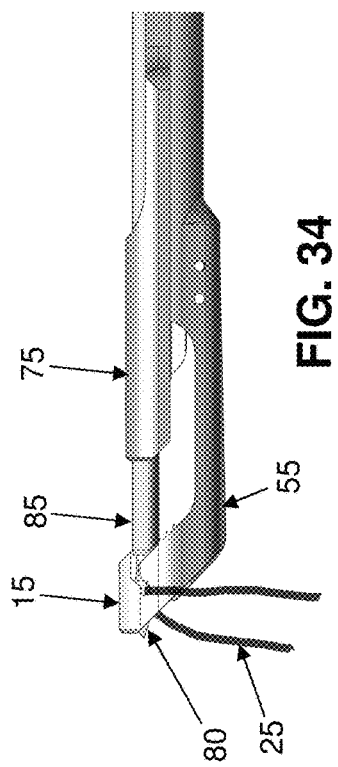
Figure 36:
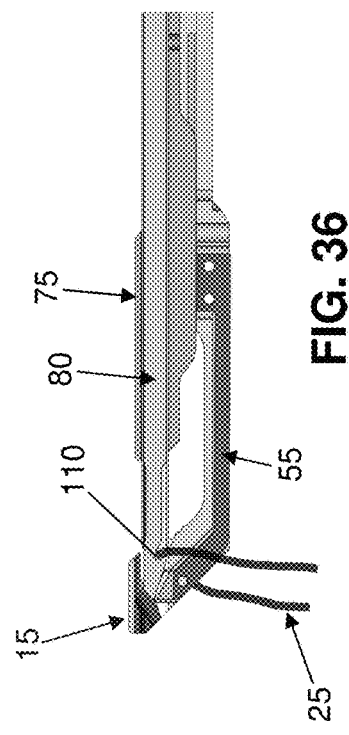

Inner needle 80 and outer needle 85 continue to move distally as a unit until the distal tips of inner needle 80 and outer needle 85 exit the far side of the tissue and the distal tip of inner needle 80 starts to enter distal jaw 15. At or near this point, forward advancement of outer needle 85 is stopped, and inner needle 80 advances alone. As inner needle 80 advances, its inclined surface 107 (FIG. 21) engages the inclined surface 72 of suture seat 70 and/or suture 25, thereby causing suture seat 70 and distal jaw spring 55 to be cammed downwardly, and thereby releasing suture 25 from the capture previously provided by suture seat 70 and distal jaw spring 55 (FIGS. 30-33). As this occurs, suture 25 is urged distally within suture slot 30, with intermediate diagonal section 40 of suture slot 30 and distal longitudinal section 45 of suture slot 30 accommodating suture 25. Inner needle 80 continues to move distally until suture slot 110 in inner needle 80 is positioned above suture 25 (FIGS. 34 and 35), whereupon distal jaw spring 55 and suture seat 70 deliver suture 25 up into suture slot 110 in inner needle 80 (FIGS. 34 and 35), i.e., under the resilient action of distal jaw spring 55. Inner needle 80 is then retracted proximally, carrying suture 25 with it, until suture 25 encounters the bevelled tip 100 of outer needle 85, whereupon suture 25 is locked between the two needles (FIG. 36). This locking acts to secure the suture 25 to the two needles 80, 85 with sufficient force that the suture is not dislodged from the inner needle 80 and outer needle 85 as the two needles are retracted proximally through the tissue and/or as the suture passer 5 is moved from the suturing site (e.g., as the suture passer 5 is removed from the patient).

Figure 37:
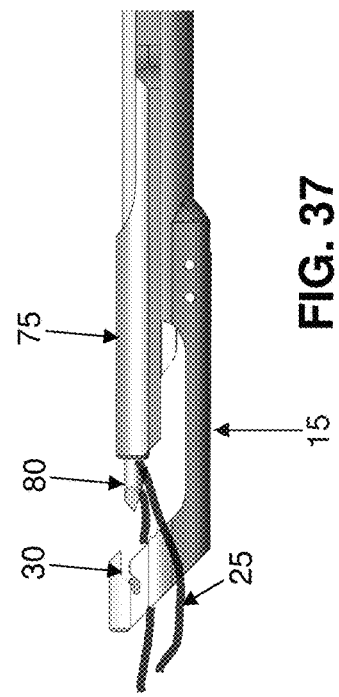

Then inner needle 80 and outer needle 85 are retracted proximally, as a unit, drawing suture 25 through the tissue which is clamped between distal jaw 15 and proximal jaw 75. See FIG. 37.

Once suture 25 has been passed through the tissue which is clamped between distal jaw 15 and proximal jaw 75, proximal jaw 75 is retracted, thereby releasing the tissue (which has suture 25 passing therethrough) from the suture passer. See FIG. 38.

This passed suture may then be used in ways well known in the art, e.g., so as to stitch closed a laid-open fibrous capsule.

Figure 40:
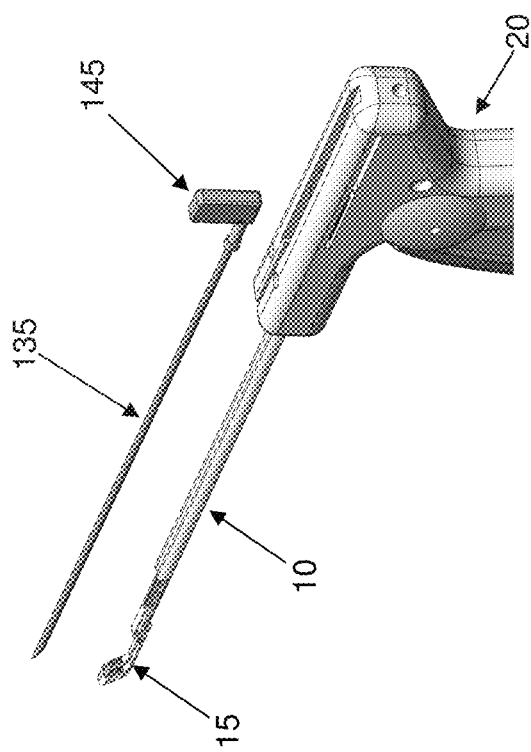
FIGS. 39 and 40 are schematic views showing how the novel suture passer of FIGS. 16 and 17 can comprise a reusable tool assembly and a disposable needle assembly.
Figure 39:
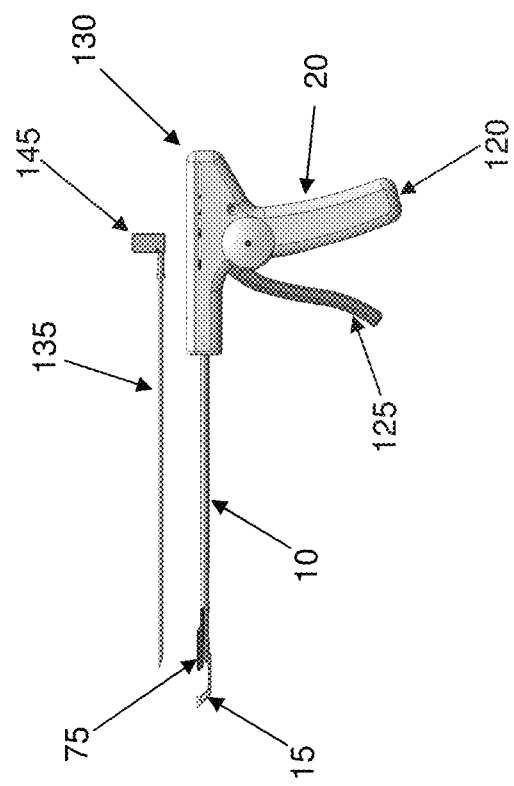
Figure 45:
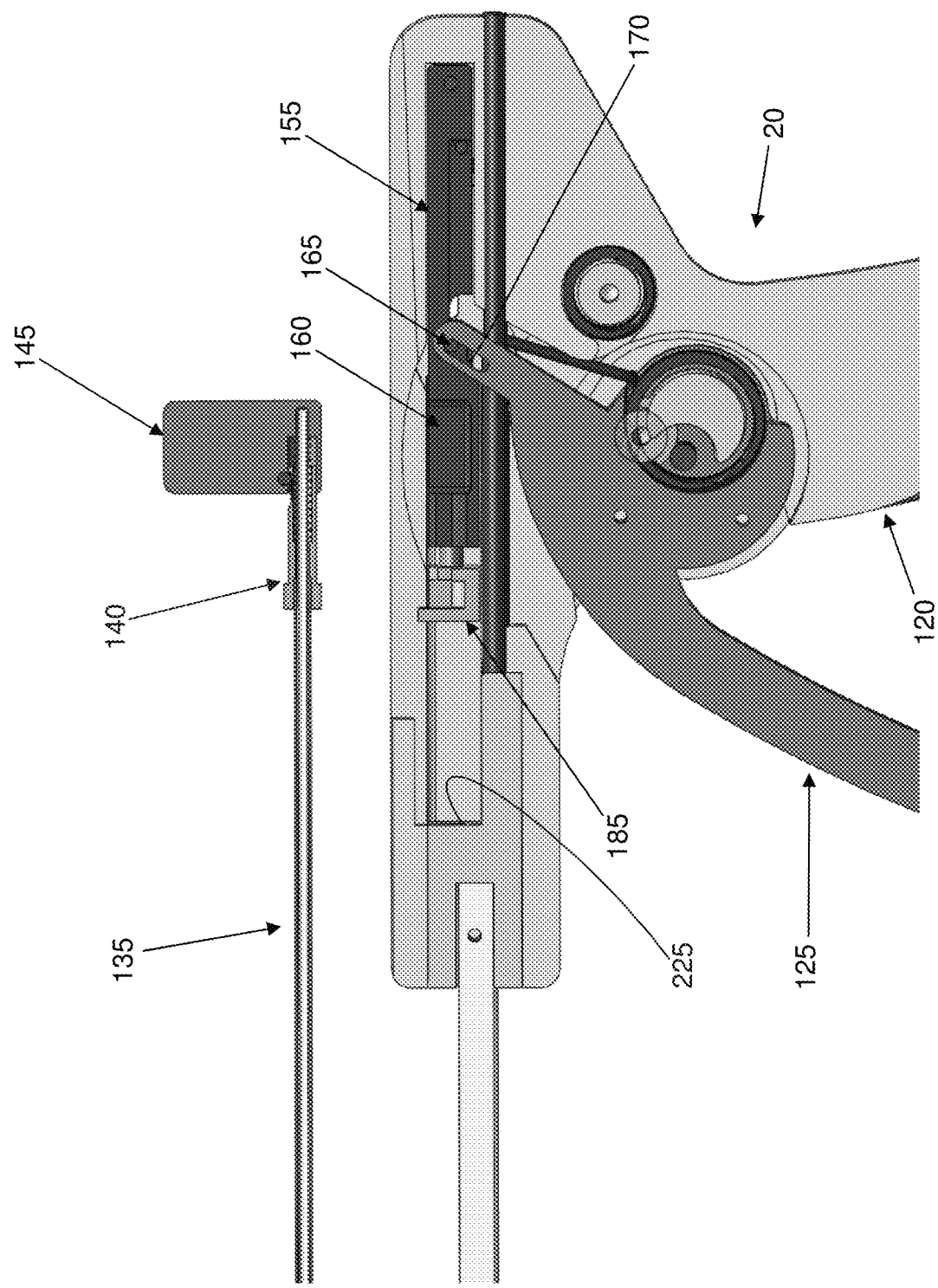

In one preferred form of the invention, and looking now at FIGS. 39 and 40, shaft 10, distal jaw 15, handle 20 and proximal jaw 75 are formed as one assembly (e.g., such as the tool assembly 130 shown in FIGS. 39 and 40), and inner needle 80 and outer needle 85 are formed as another assembly (e.g., such as the needle assembly 135 shown in FIGS. 39 and 40). Such a construction can be highly advantageous, since it permits tool assembly 130 to be reusable and needle assembly 135 to be disposable.

In one preferred form of the invention, and looking now at FIGS. 41-44, needle assembly 135 comprises (i) the aforementioned outer needle 85 and a hub 140 secured to the proximal end of outer needle 85, and (ii) the aforementioned inner needle 80 and a tab 145 secured to the proximal end of inner needle 80. A spring 150 is disposed between hub 140 and tab 145, so as to yieldably bias hub 140 and tab 145 away from one another. As a result, spring 150 yieldably biases inner needle 80 proximally relative to outer needle 85, as will hereinafter be discussed in further detail.

Looking next at FIGS. 45-48, handle 20 preferably has a needle carriage 155 movably mounted therein. Needle carriage 155 includes a tab slot 160 for receiving tab 145 of needle assembly 135, as will hereinafter be discussed. Trigger 125 is connected to needle carriage 155 so that moving trigger 125 towards grip 120 causes needle carriage 155 to move distally relative to handle 20. Preferably trigger 125 is connected to needle carriage 155 via a pin-and-slot mechanism, i.e., a pin 165 riding in a slot 170. A spring 175 (FIG. 47), engaging a pin 180 extending out of needle carriage 155, biases needle carriage 155 proximally relative to handle 20 (and hence biases trigger 125 away from grip 120). Spring 175 ensures that needle carriage 155 is returned to the full proximal position when trigger 125 is released.

Handle 20 also includes a flange seat 185 (FIG. 45) movably mounted therein. Flange seat 185 is spring-mounted to needle carriage 155 so that flange seat 185 is spring-biased distally from needle carriage 155. In one preferred form of the invention, flange seat 185 is spring-mounted to needle carriage 155 via a pair of posts 190 (FIG. 47) and a pair of springs 195. Flange seat 185 is adapted to receive a locating flange 200 (FIG. 44) on hub 140 as will hereinafter be discussed.

Handle 20 also includes a proximal jaw carriage 205 (FIG. 46) movably mounted therein. Proximal jaw carriage 205 is connected to the proximal end of proximal jaw 75 so that the two elements move as a unit. An extension 210 of a spring 215 is seated in an opening 220 formed in proximal jaw carriage 205 so that spring 215 biases proximal jaw carriage 205 proximally, and hence biases proximal jaw 75 proximally, as will hereinafter be discussed.

Figure 46:
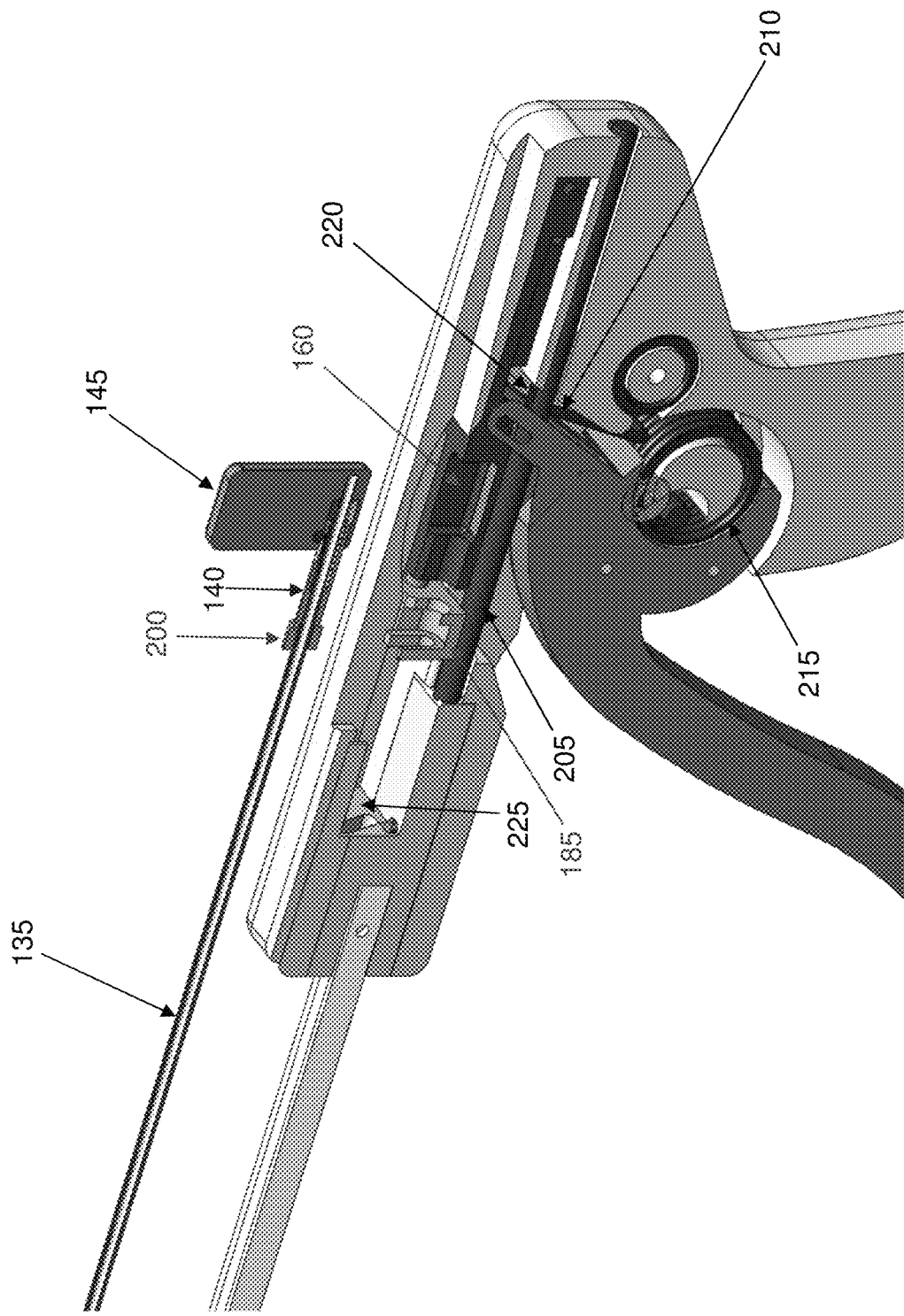
Figure 46A:
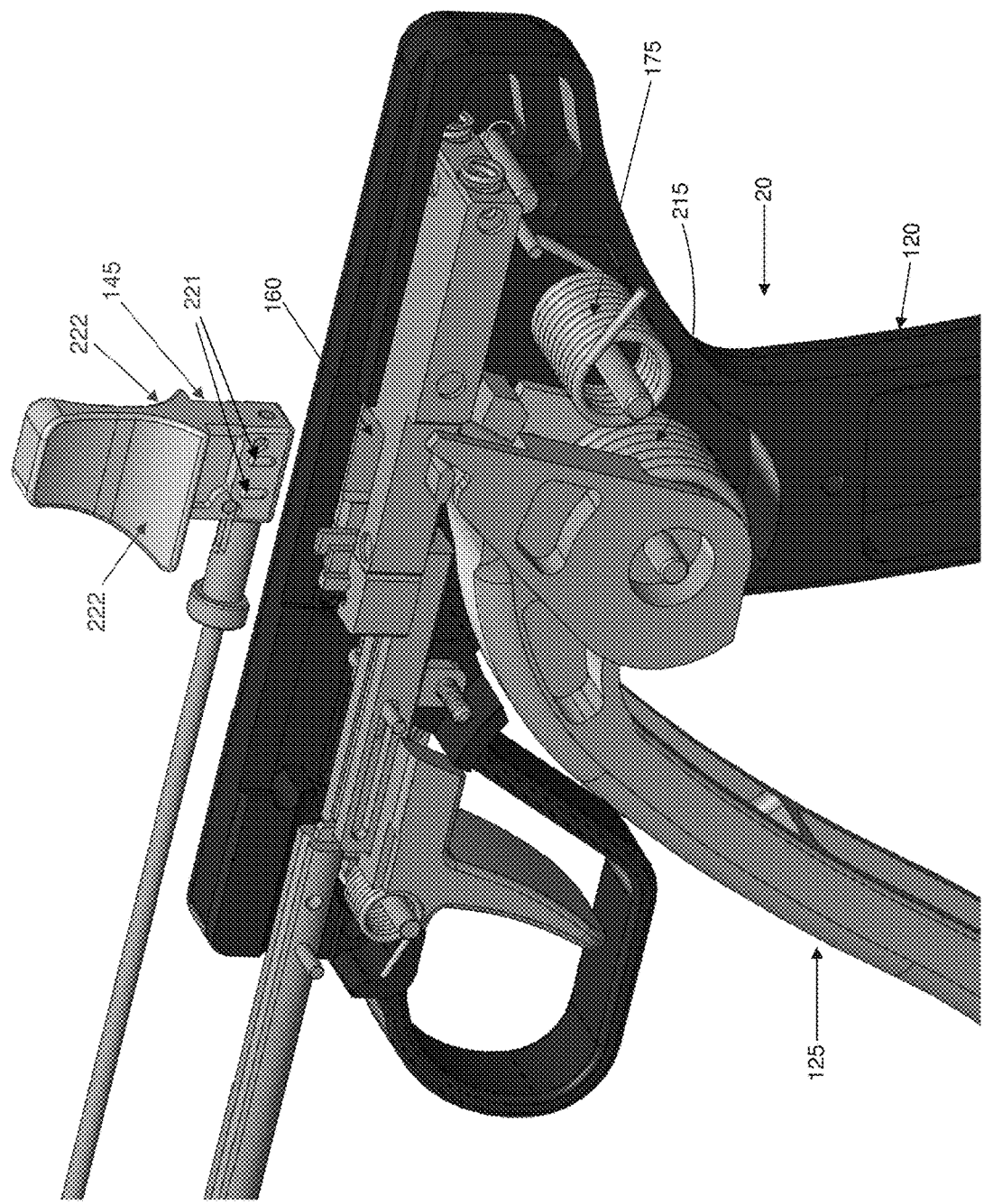
Figure 47:
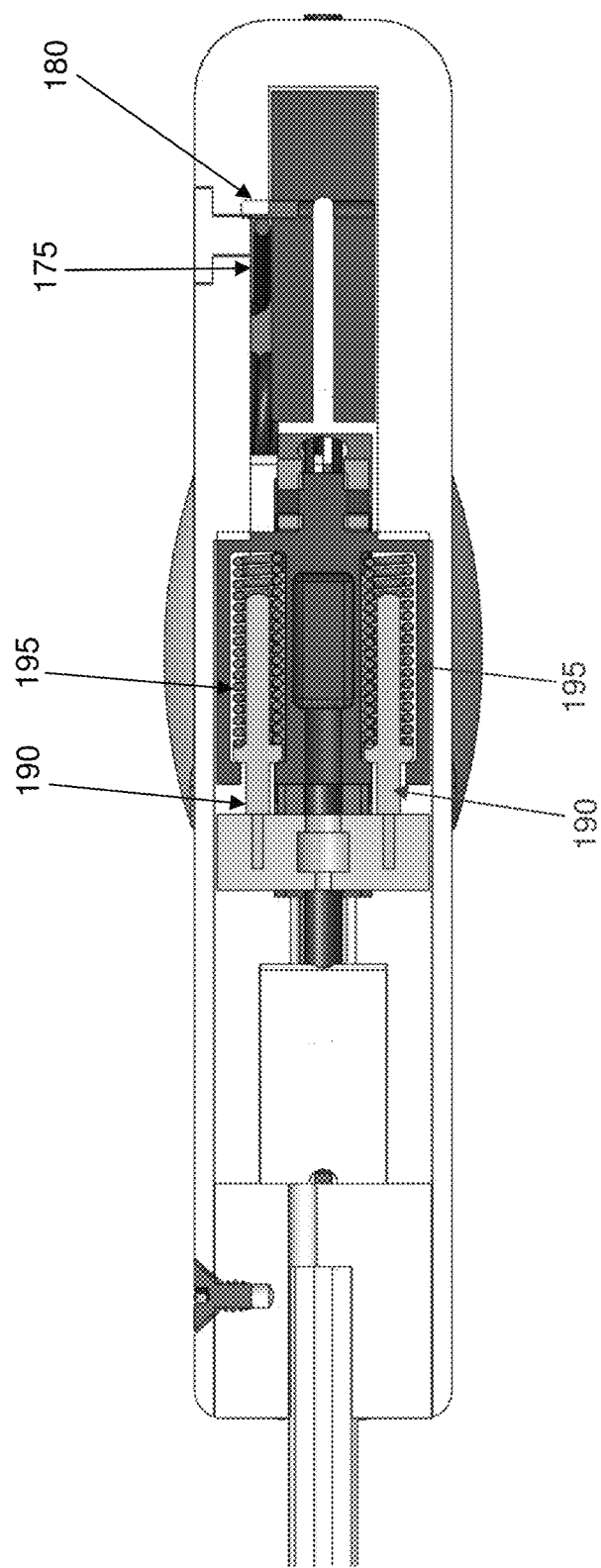
Figure 48:
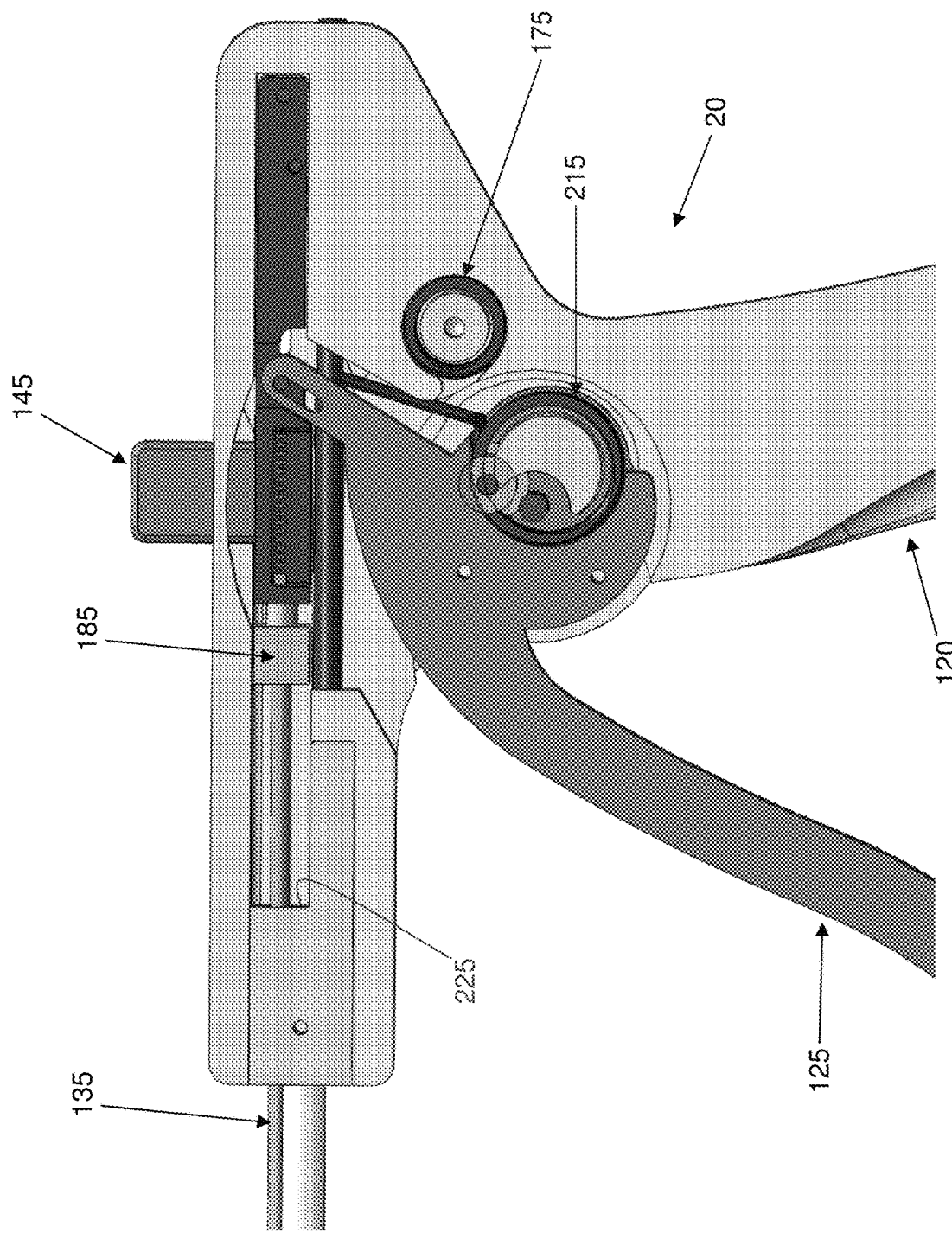

Needle assembly 135 is loaded into tool assembly 130 by fitting locating flange 200 (FIG. 44) of hub 140 into flange seat 185, and by fitting tab 145 into tab slot 160 of needle carriage 155. See FIG. 48. Tab 145 may preferably be made of a polymer. Tab 145 may have one or more "crush ribs" formed on its outer surfaces which help to create a secure interference fit between tab 145 and tab slot 160; this interference fit aids in preventing needle assembly 135 from inadvertently becoming dislodged from the tool assembly 130 during use (e.g., such as by gravity if the suture passer 5 is used upside down). See, for example, FIG. 46A, which shows a plurality of crush ribs 221 formed on tab 145. These crush ribs 221 form an interference fit with the surrounding walls of tab slot 160 so as to help hold tab 145 in tab slot 160. Note also that in the construction shown in FIG. 46A, tab 145 includes a pair of finger seats 222 to facilitate easy grasping of tab 145 by the user, e.g., when inserting tab 145 into tab slot 160 or when removing tab 145 from tab slot 160.

On account of the foregoing construction, when trigger 125 is moved towards grip 120, proximal jaw carriage 205 is moved distally by extension 210 of spring 215, thereby causing proximal jaw 75 to move distally so as to engage tissue disposed in the gap 127 between distal jaw 15 and proximal jaw 75. As this occurs, needle carriage 155 also moves distally, which in turn causes tab 145 (and hence inner needle 80) to also move distally. At the same time, due to the relative rigidity of springs 195 (FIG. 47), flange seat 185 also moves distally, causing hub 140 (and hence outer needle 85) to also move distally, thereby causing inner needle 80 and outer needle 85 to move distally as a unit.

This coordinated distal movement of proximal jaw 75, inner needle 80 and outer needle 85 continues until the force applied to the tissue by proximal jaw 75 equates to the maximum force that spring 215 (FIG. 46) can apply. Spring 215 then begins to wind up, whereupon proximal jaw carriage 205 stops moving distally (and hence proximal jaw 75 stops moving distally), while needle carriage 155 keeps moving distally, thereby causing inner needle 80 and outer needle 85 to continue moving distally, whereby to penetrate the tissue in unison.

Figure 49:
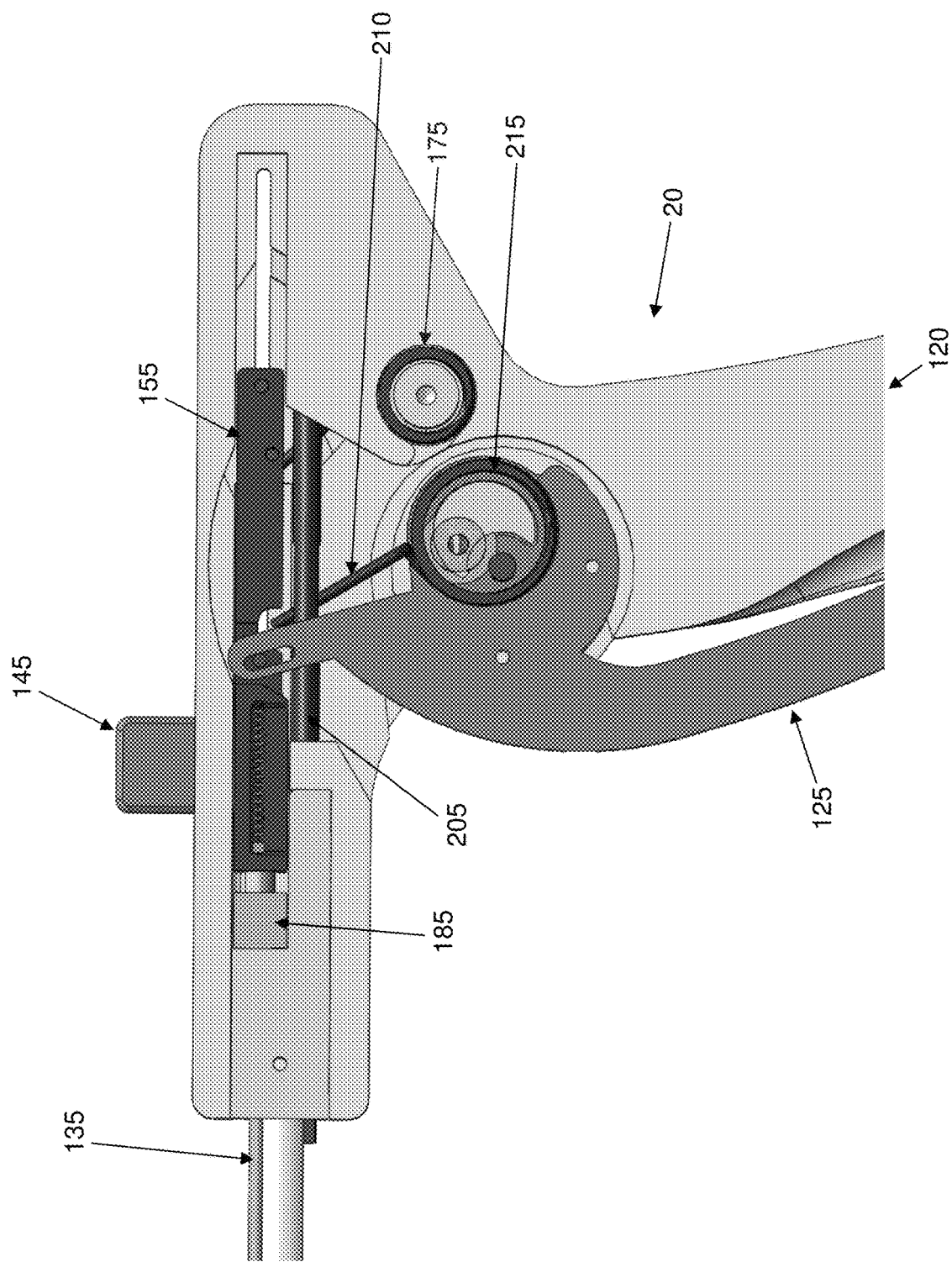
Figure 50:
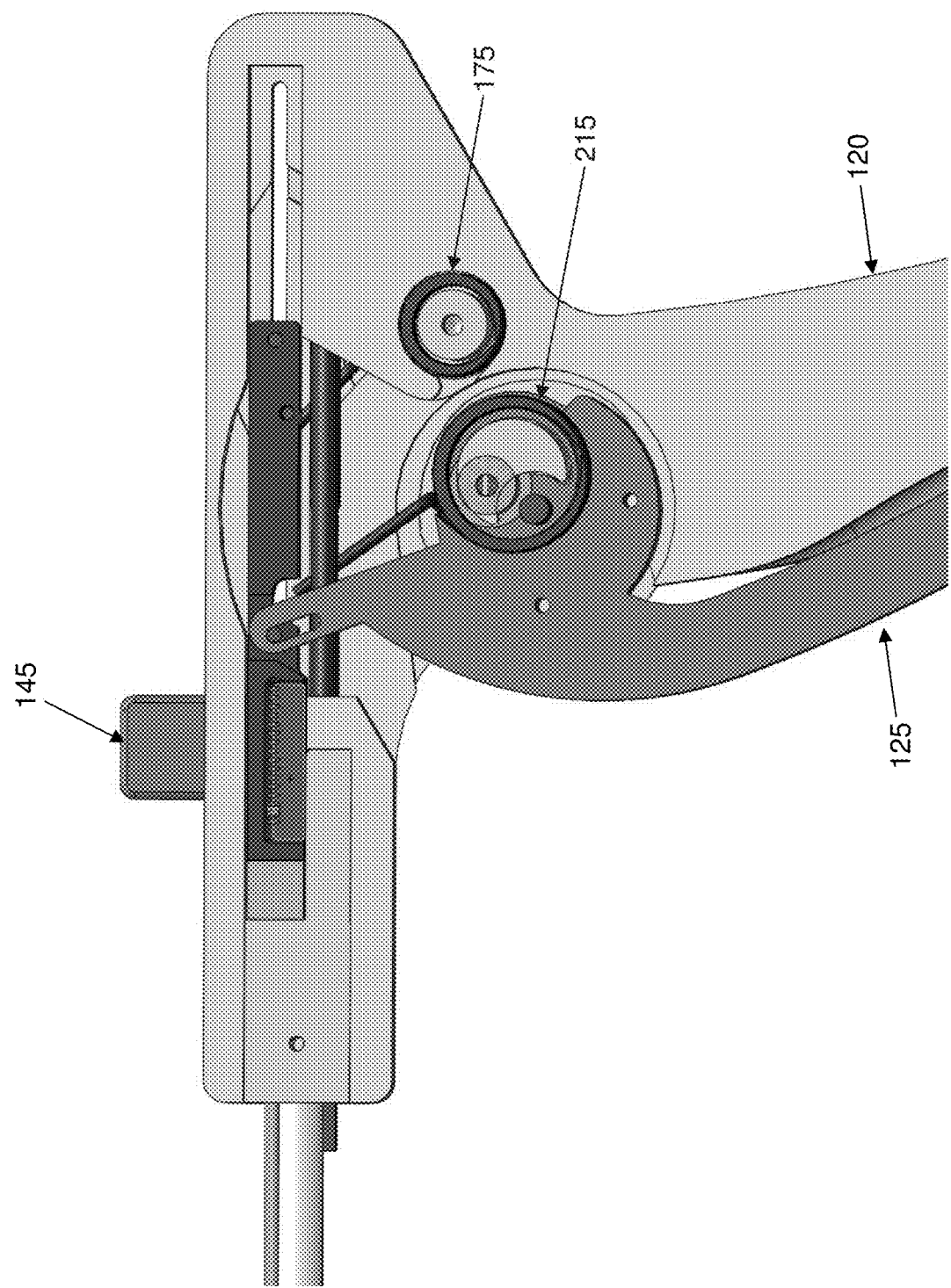

Continued movement of trigger 125 toward grip 120 causes the elements to move further distally until flange seat 185 engages a stop 225 formed in handle 20 (FIG. 49), thereby preventing further distal movement of flange seat 185, and hence preventing further distal movement of hub 140, and hence preventing further distal movement of outer needle 85. However, continued movement of trigger 125 toward grip 120 causes tab 145 to be moved distally (FIG. 50) so as to overcome the power of spring 150 (FIG. 44), so that inner needle 80 is advanced distally relative to outer needle 85, whereby to permit inner needle 80 to engage suture seat 70 of distal jaw spring 155, cam distal jaw spring 55 out of the way, and align suture slot 110 of inner needle 80 with suture 25.

The amount of relative movement between inner needle 80 and outer needle 85 can be set in a variety of ways, including having flange seat 185 stop forward distal progress of needle carriage 155. Alternatively, further movement of trigger 125 can be stopped by grip 120 at a set position so as to limit longitudinal movement of inner needle 80 relative to outer needle 85.

Releasing trigger 125 causes, sequentially, needle carriage 155 to withdraw proximally so as to permit inner needle 80 to be moved proximally by spring 150 while hub 140 (and hence outer needle 85) remains stationary, thereby picking up suture 25 in suture slot 110 and then capturing suture 25 between inner needle 80 and outer needle 85. Continued release of trigger 125 causes tab 145 and hub 140 (and hence inner needle 80 and outer needle 85) to move proximally as a unit, and hence causes inner needle 80 and outer needle 85 to withdraw back through the tissue as a unit, carrying the suture therewith. Continued release of trigger 125 causes spring extension 210 to move proximal jaw carriage 205 proximally, whereby to withdraw proximal jaw 75 from the tissue, thereby releasing the tissue from suture passer 5, with suture 25 extending through the tissue.

Figure 25:
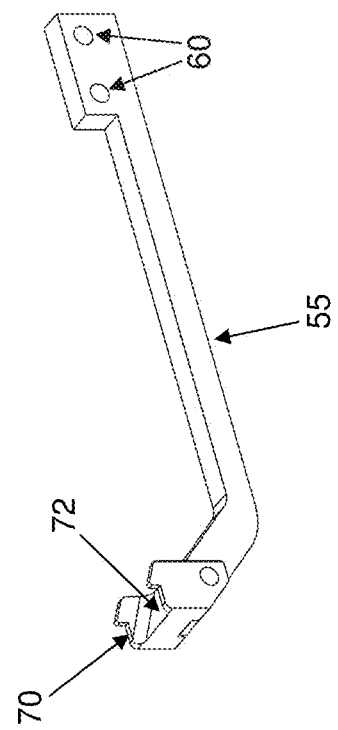
Figure 24:
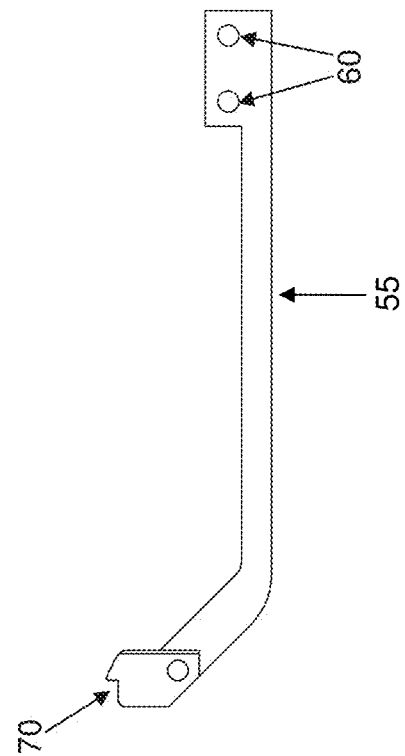

It should be appreciated that the portion of distal jaw spring 55 which aids in holding suture 25 to distal jaw 15 can take many forms other than that shown in FIGS. 24 and 25. By way of example but not limitation, the spring surface that comes into contact with the suture can have a single tooth, multiple teeth or a roughened finish so as to promote the spring's ability to hold the suture. This portion of the distal jaw spring can also have a perpendicular surface that acts to keep suture 25 from moving distally as inner needle 80 passes over the suture.

Thus, FIGS. 50A, 50B and 50C show one alternative form of distal jaw spring 55. In this form of the invention, suture seat 70 has its inclined surface 72 formed with an arcuate configuration to receive inner needle 80 during its forward stroke, and includes teeth 226 for positively engaging suture 25 and forcing suture 25 against the opposing side wall of the suture slot. In addition, the proximal end of distal jaw spring 55 is modified so that only one pin 60 (FIG. 19) is required—this pin 60 acts as a pivot pin, and clockwise motion of distal jaw spring 55 about this pivot pin is limited by a stop surface 227 which engages a corresponding stop surface on shaft 10.

Figure 50E:
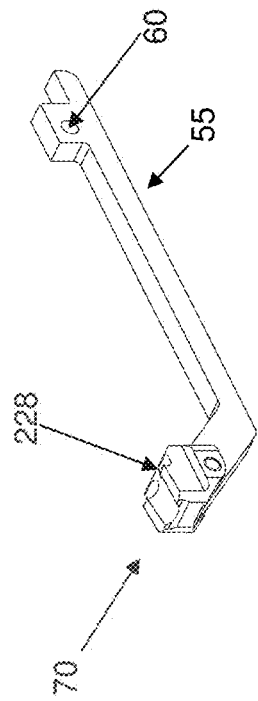
FIGS. 50D, 50E and 50F are schematic views showing another alternative form of the distal jaw spring of the novel suture passer of FIGS. 16 and 17.
Figure 50F:
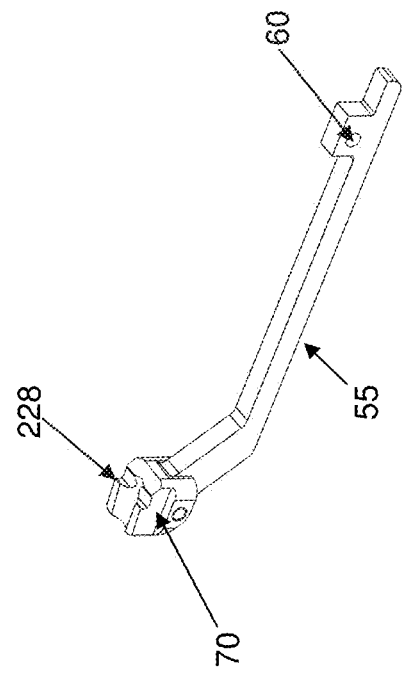
Figure 50D:
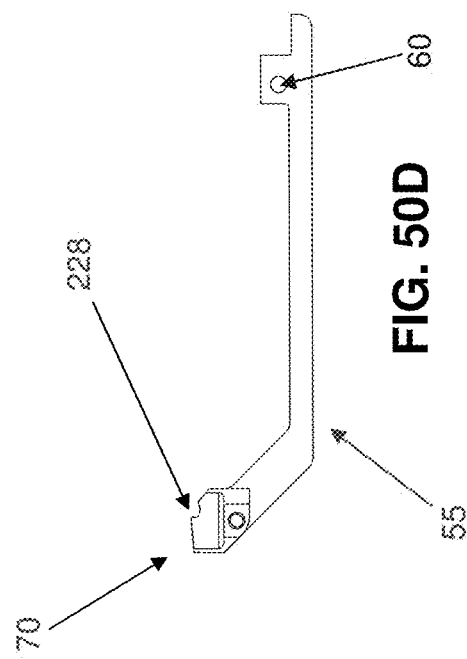

FIGS. 50D, 50E and 50F show another alternative form of distal jaw spring 55. In this form of the invention, suture seat 70 has a backstop feature 228 to limit distal migration of suture 25 when inner needle 80 is driving past the suture during the needle's forward stroke. In this embodiment, the beveled tip 100 (FIG. 21) of outer needle 85 may act to pinch the suture against the backstop feature 228 of distal jaw spring 55 so that the suture is securely held in place as the inner needle 80 passes over the suture during the needle's forward stroke.

Figure 50H:
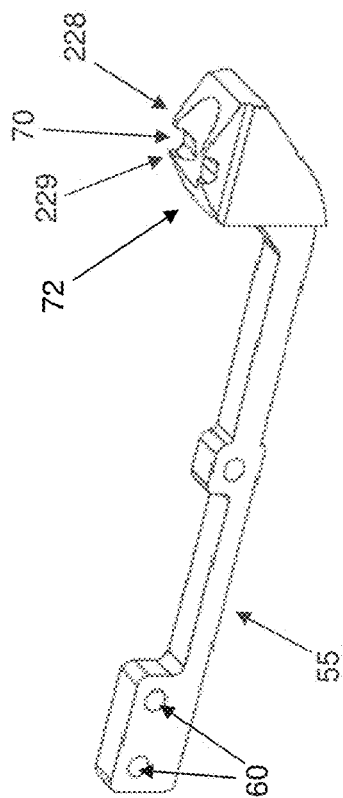
FIGS. 50G and 50H are schematic views showing another form of the novel suture passer of the present invention.
Figure 50G:
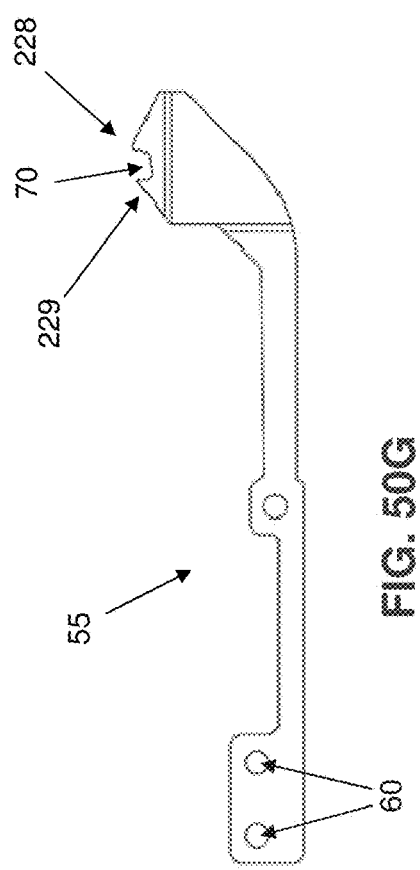

FIGS. 50G and 50H show another alternative form of distal jaw spring 55. In this form of the invention, a suture catch 229 is formed on the proximal side of the suture seat 70. The suture catch 229 limits proximal migration of suture 25 when, for example, device manipulation results in forces on the suture 25 which tend to dislodge the suture 25. In this embodiment of the invention, a backstop feature 228 is also located on the distal side of suture seat 70 so as to limit distal migration of suture 25 when inner needle 80 is driving past the suture during the needle's forward stroke. In essence, in this form of the invention, the suture seat 70 is essentially a trough or recess defined by distal backstop feature 228 and proximal suture catch 229, and suture 25 is disposed in this trough or recess, thereby preventing distal movement of the suture (e.g., due to needle advancement) via distal backstop feature 228 and preventing proximal movement of the suture (e.g., due to advancement of the needle passer through the septum of a cannula) via proximal suture catch 229, whereby to more securely hold suture 25 to suture passer 5. Preferably the depth of the trough or recess of suture seat 70 is at least 50% of the height of the suture which is to be seated in the trough or recess, so as to reliably retain suture 25 in the trough or recess of suture seat 70 while distal jaw spring 55 is in its spring-biased position (i.e., before distal jaw spring 55 is displaced by inner needle 80). In other words, when a suture 25 is seated in the trough or recess of suture seat 70, distal backstop feature 228 and proximal suture catch 229 will extend up to the midpoint on suture 25 or, preferably, even higher on suture 25, whereby to provide secure stabilization for the suture vis-à-vis distal jaw spring 55. In addition to the foregoing, it should be appreciated that distal jaw spring 55 can be made from one or more suitable materials including plastic, metal (e.g., stainless steel, titanium, etc.) and, more specifically, superelastic materials such as Nitinol. Furthermore, the cantilevered portion of distal jaw spring 55 may be one material (e.g., superelastic Nitinol) and the suture-capturing portion of distal jaw spring 55 may be another material (e.g., a molded plastic tip). In this respect it should also be appreciated that the cantilevered portion of distal jaw spring 55 may be thicker at its proximal end than at its distal end; for example, it may be tapered. Such tapering may allow the flexing characteristics of distal jaw spring 55 to vary along its length.

Figure 52:
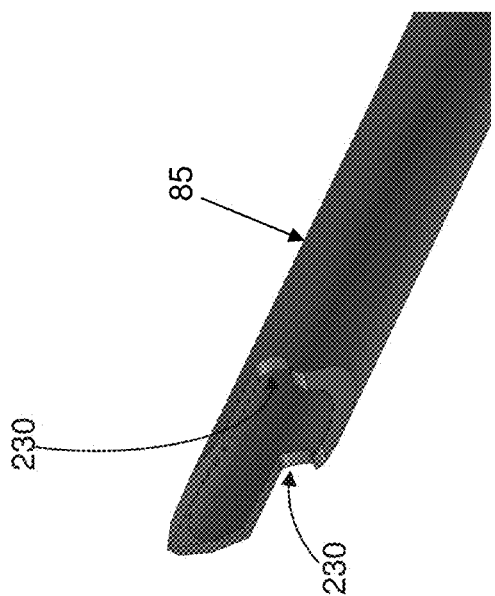
FIGS. 51 and 52 are schematic views showing an alternative form of the outer needle of the novel suture passer of the present invention.
Figure 51:
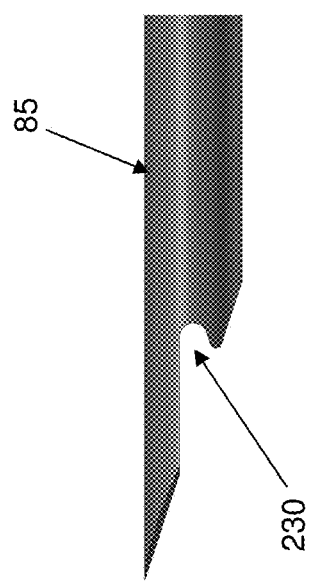

FIGS. 51 and 52 show an alternative form of outer needle 85. In this form of the invention, outer needle 85 includes a suture slot 230 at its distal end. Suture slot 230 in outer needle 85 is aligned with, and cooperates with, suture slot 110 in inner needle 80 so as to form a positive suture seat between the two needles when inner needle 80 is retracted toward outer needle 85, whereby to securely capture suture 25 to the two needles.

Figure 54:
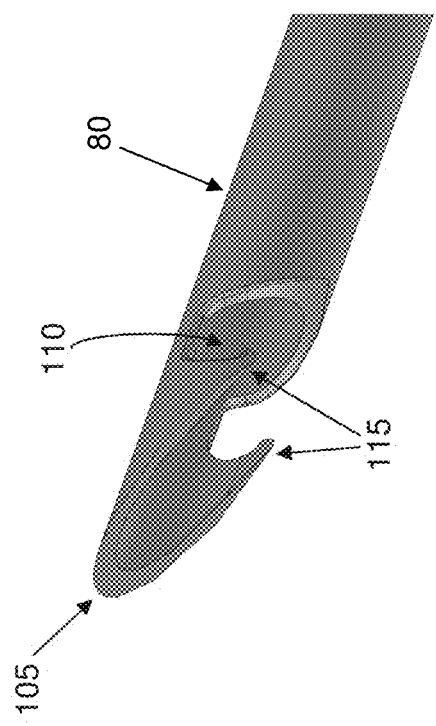
FIGS. 53 and 54 are schematic views showing an alternative form of the inner needle of the novel suture passer of the present invention.
Figure 53:
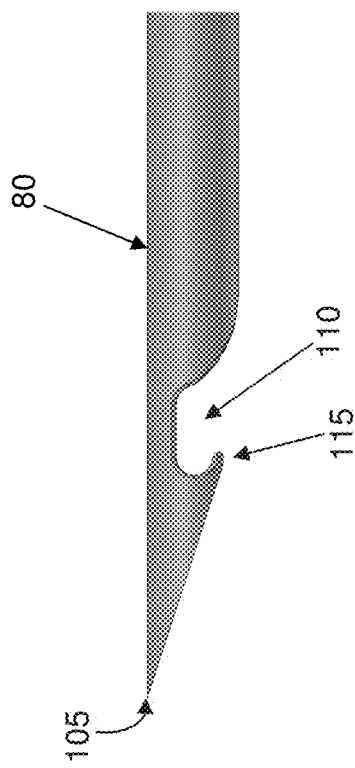
Figure 59:
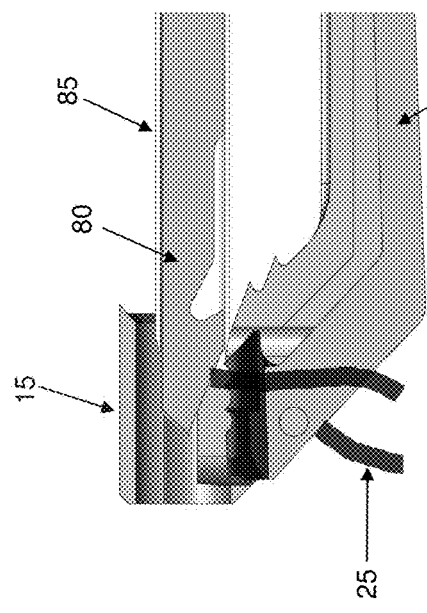
Figure 60:
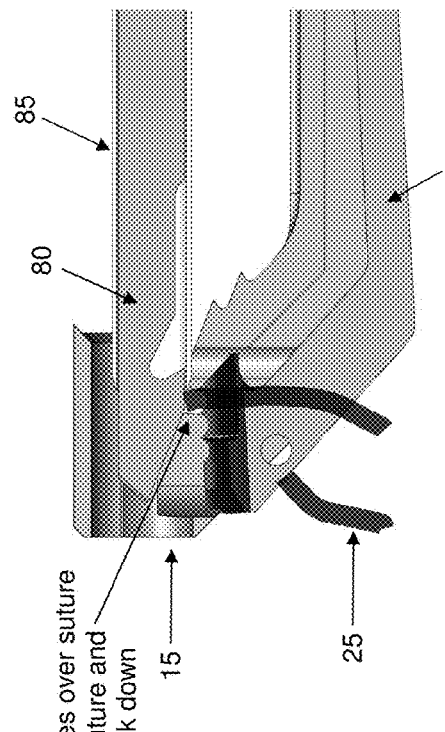
Figure 61:
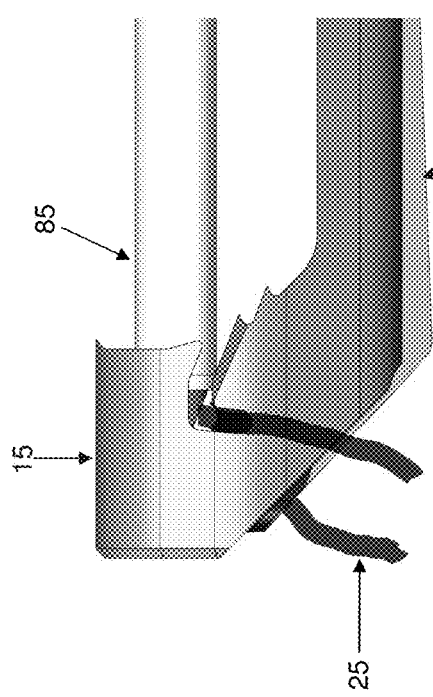
Figure 62:
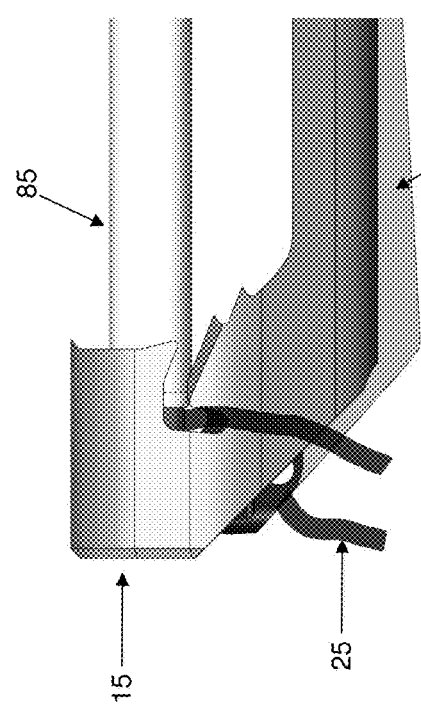
Figure 63:
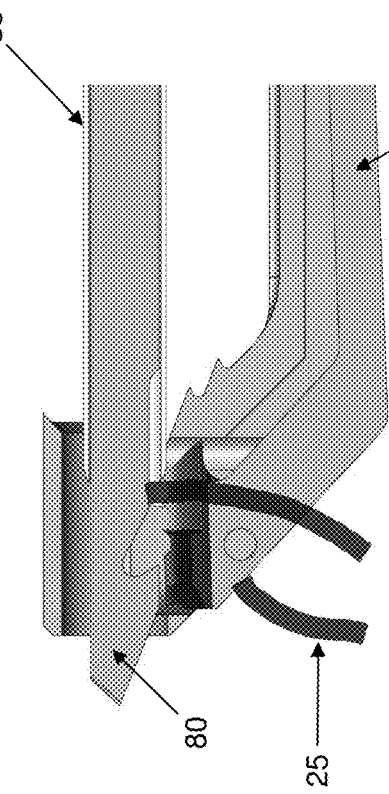
Figure 64:
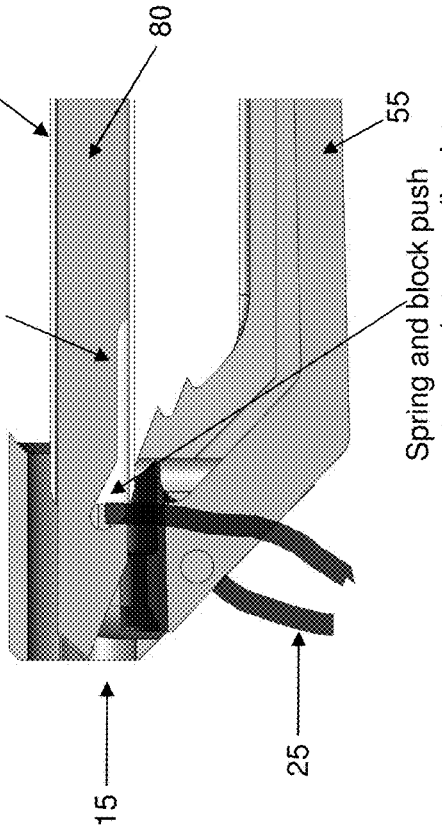
Figure 65:
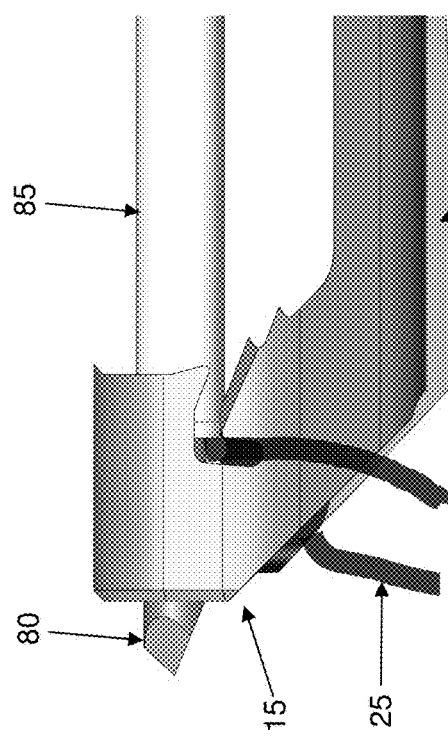
Figure 66:
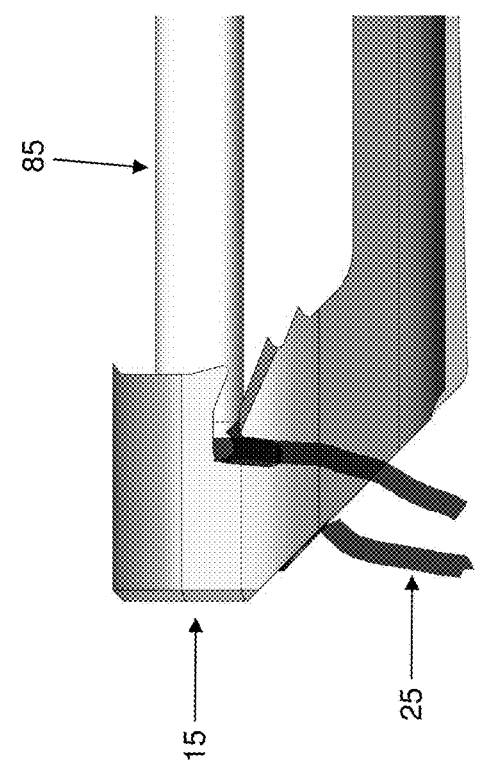

FIGS. 53 and 54 show an alternative form of inner needle 80. In this form of the invention, inner needle 80 is hollow, so that objects and/or fluids can be passed through the interior of inner needle 80.

FIGS. 55-68 show another preferred construction for the present invention. More particularly, the construction shown in FIGS. 55-68 is generally similar to the construction shown in FIGS. 16-38, except that (i) suture slot 30 comprises a proximal diagonal section 235 (FIG. 55) and a distal substantially vertical section 240, and (ii) suture seat 70 in distal jaw spring 55 is replaced by a suture capture block 245 (FIG. 56). In this form of the invention, suture 25 follows the diagonal/vertical configuration of suture slot 30, and suture capture block 245 acts to stabilize suture 25 for positive pickup by inner needle 80.

Figure 68B:
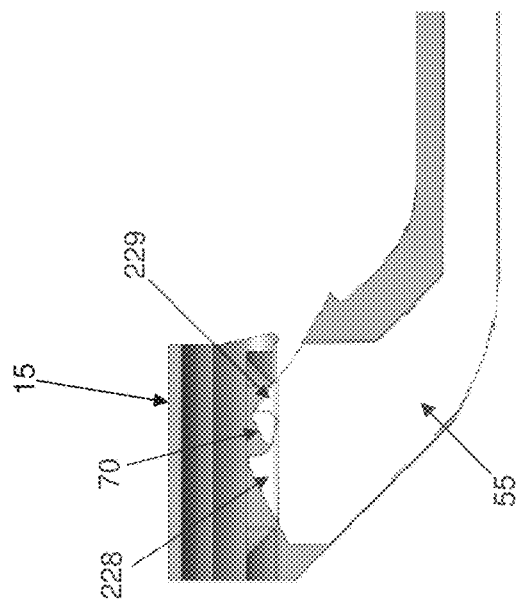
Figure 68D:
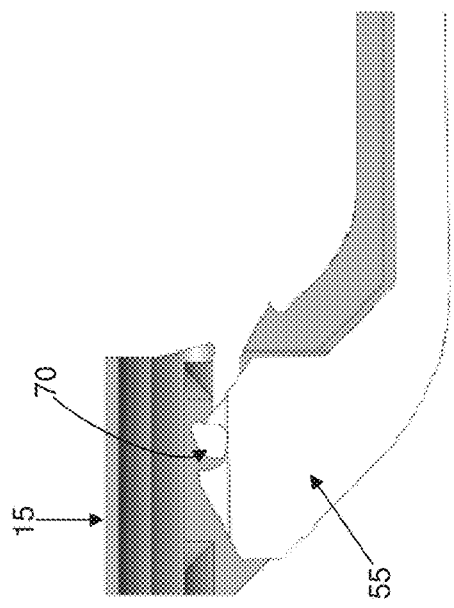
Figure 68A:
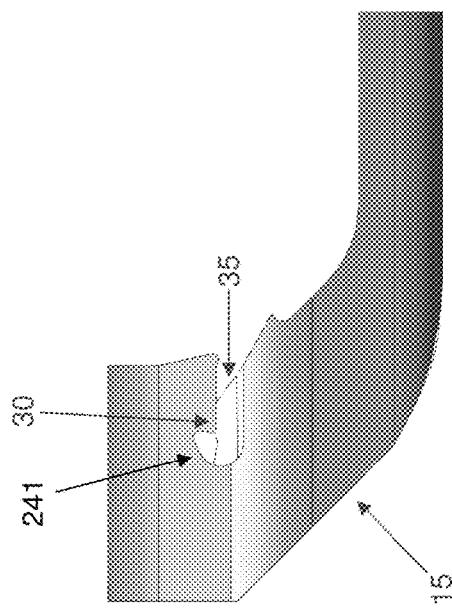
FIGS. 68A-68N are schematic views showing another form of the novel suture passer of the present invention.
Figure 68C:
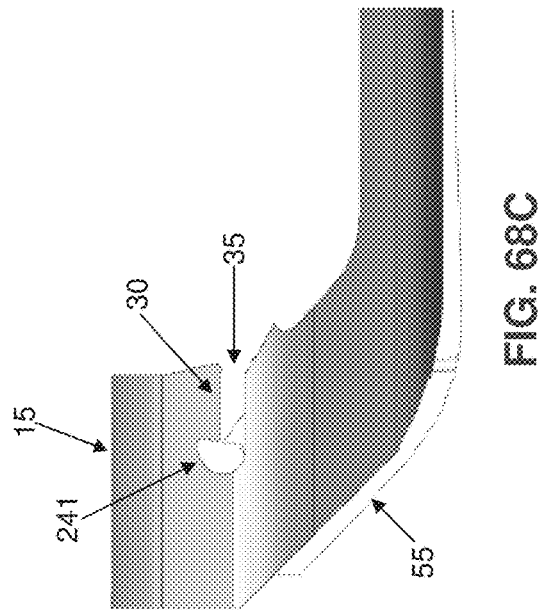
Figure 68E:
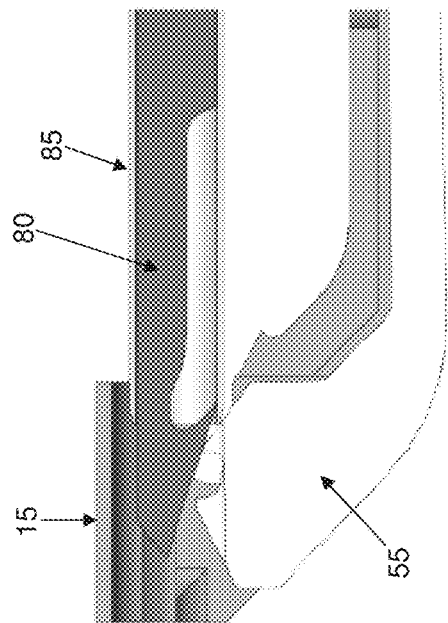
Figure 68F:
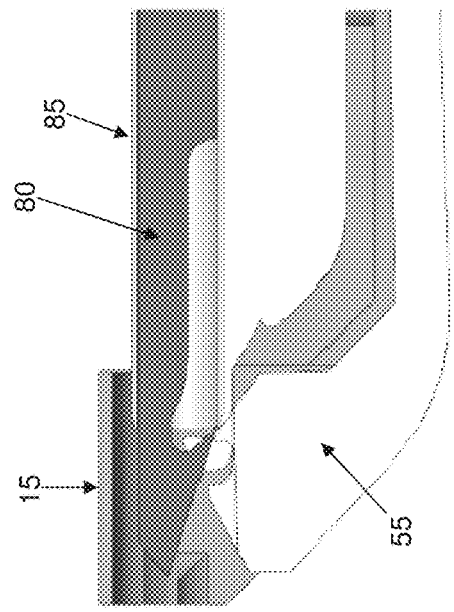
Figure 68G:
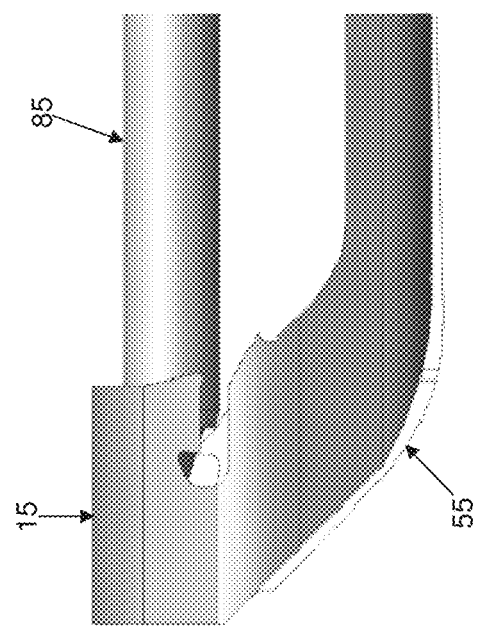
Figure 68H:
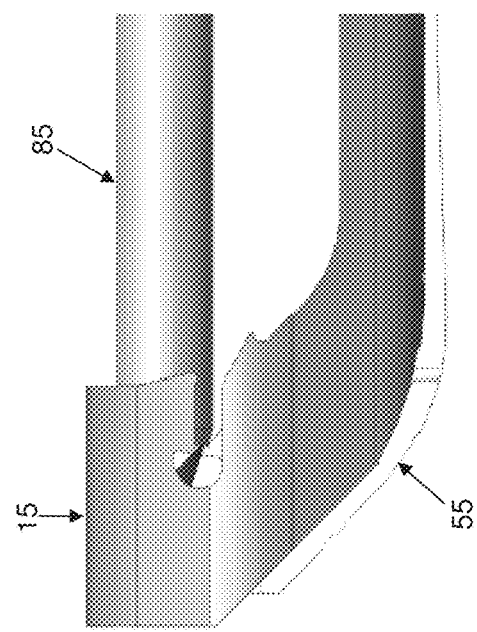
Figure 68I:
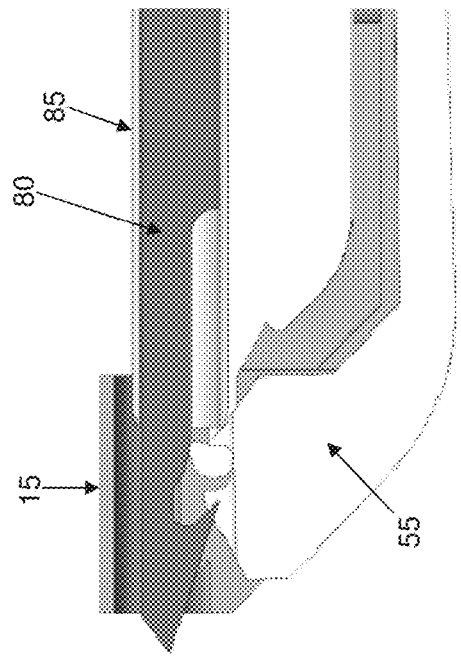
Figure 68J:
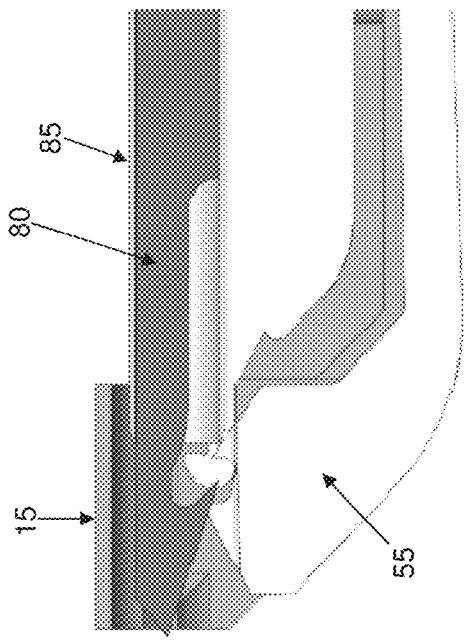
Figure 68K:
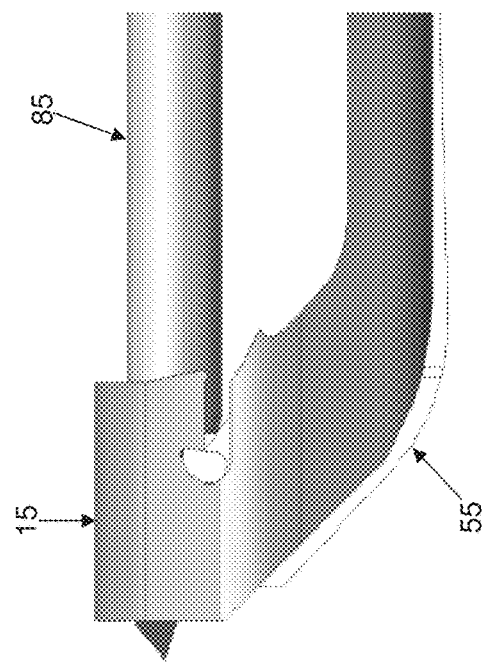
Figure 68L:
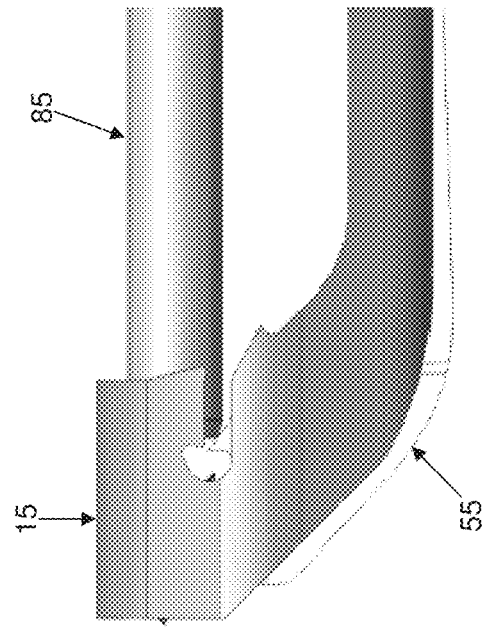
Figure 68N:
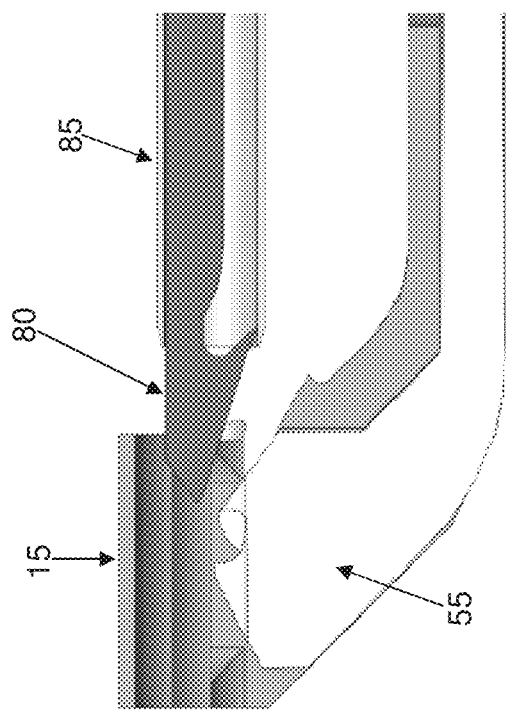

FIGS. 68A-68N show another preferred construction for the present invention. More particularly, the construction shown in FIGS. 68A-68N is generally similar to the construction shown in FIGS. 16-38, with the primary differences being that: (i) distal jaw spring 55 comprises the construction shown in FIGS. 50G and 50H and described above; and (ii) suture slot 30 in distal jaw 55 comprises a proximal longitudinal section 35 and a distal vertical section 241. Distal jaw spring 55 biases suture 25 up into distal vertical section 241 of suture slot 30; this limits migration of suture 25 (i.e., both distally and proximally) when, for example, device manipulation results in forces on the suture 25 which tend to dislodge the suture 25 from distal jaw 15. In other words, in this form of the invention, distal jaw 15 comprises an L-shaped slot 30 having a distal vertical section 241 and distal jaw spring 55 comprises a U-shaped suture seat 70 (i.e., the "trough" suture seat 70 formed between distal backstop feature 228 and proximal suture slot catch 229—the two geometries combine with one another so as to form a secure seat for the suture, thereby preventing distal and proximal movement of the suture. In other words, the two opposing slots (i.e., distal vertical section 241 of L-shaped slot 30 in distal jaw 15 and trough suture seat 70 in distal jaw spring 55) combine to capture suture 225 therebetween, whereby to prevent any longitudinal migration (i.e., either distally or proximally) of the suture.

Figure 68M:
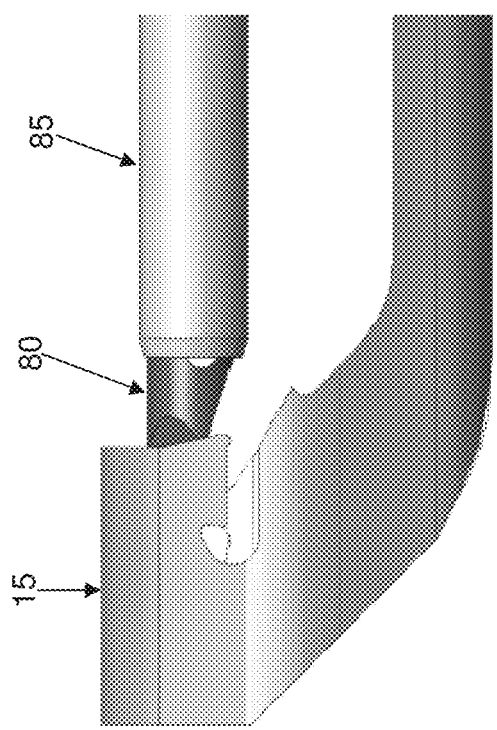
Figure 70:
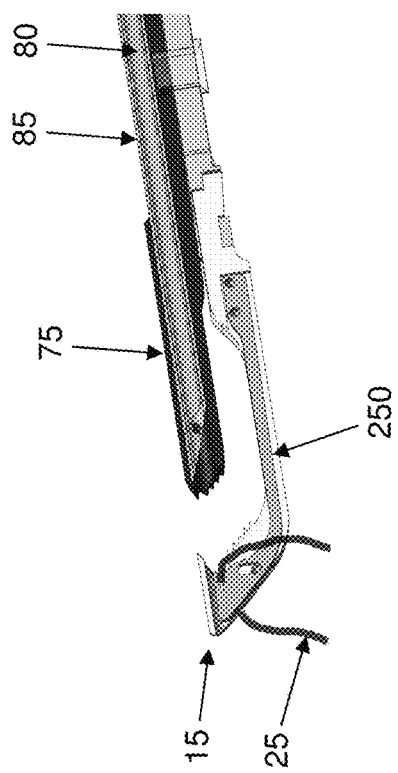
FIGS. 69-84 are schematic views showing various details of the construction and operation of the distal end of another alternative form of the novel suture passer of the present invention.
Figure 69:
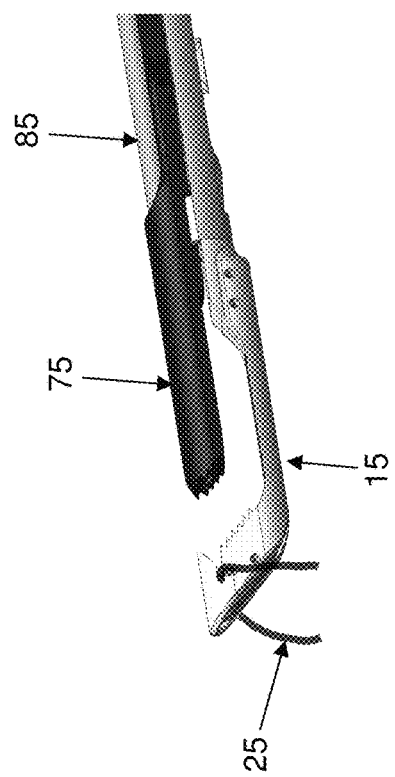
Figure 72:
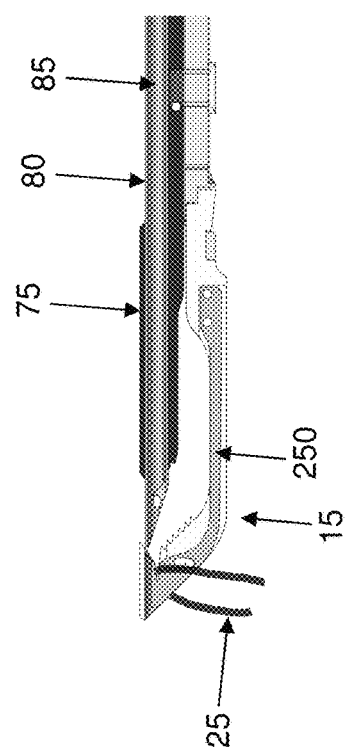
Figure 71:
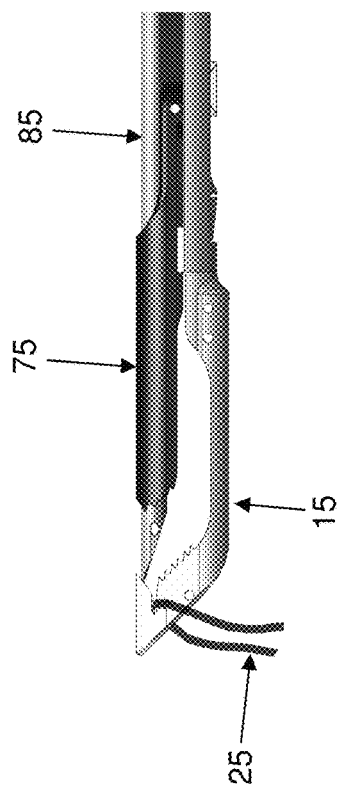
Figure 74:
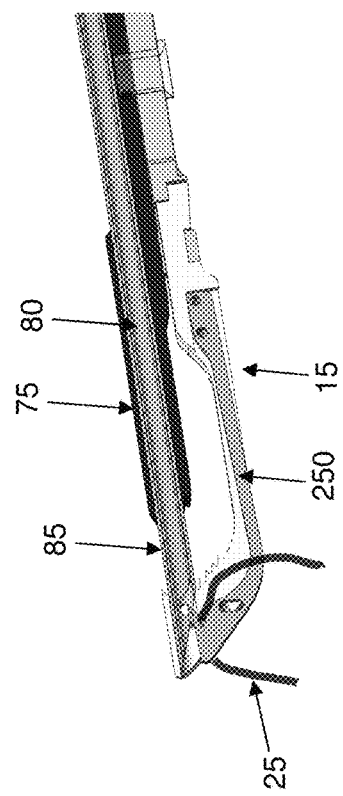
Figure 73:
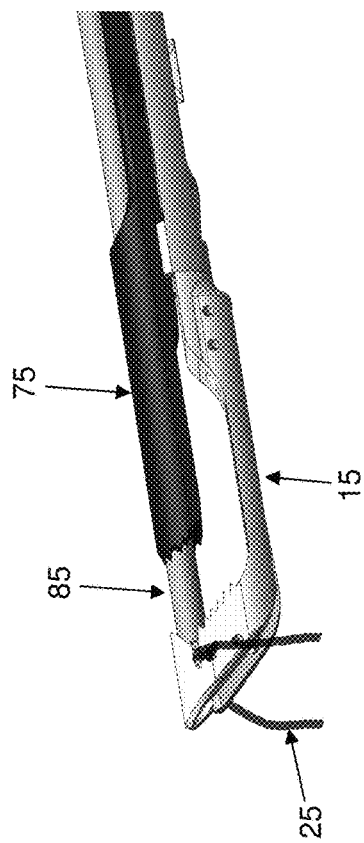
Figure 76:
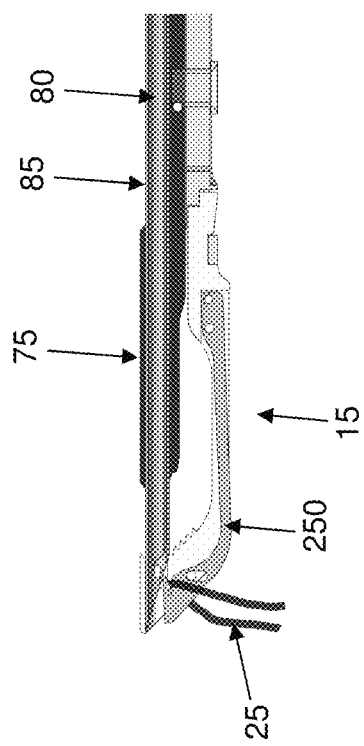
Figure 75:
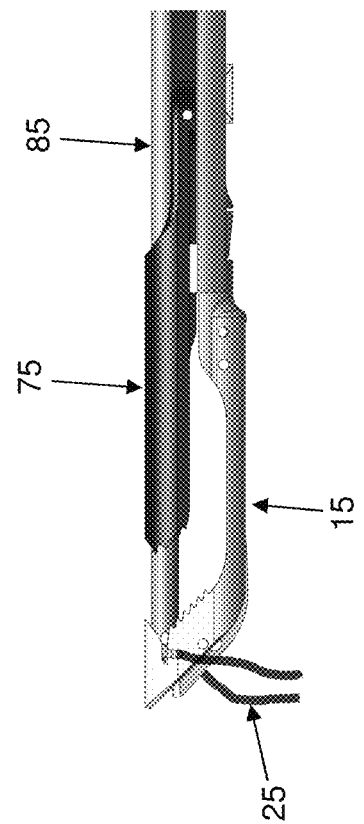
Figure 77:
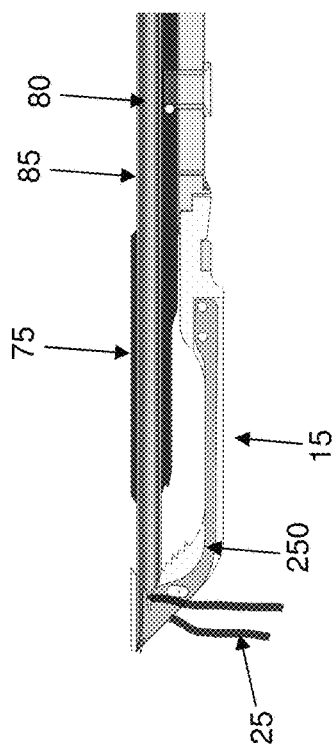
Figure 78:
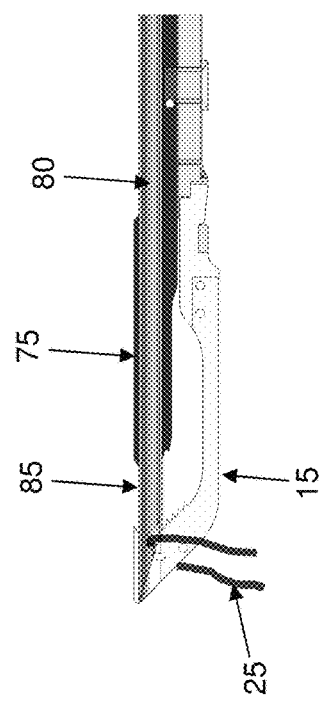
Figure 79:
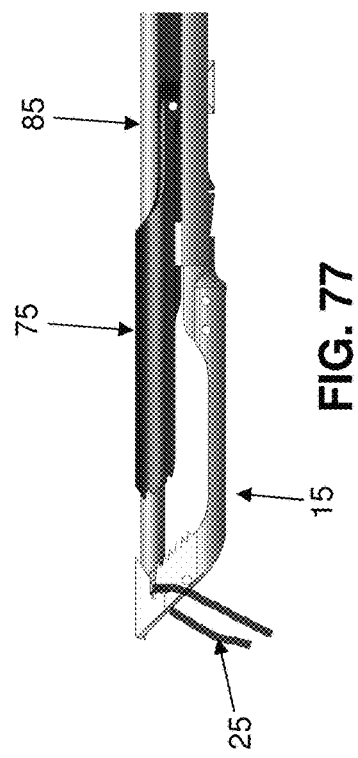
Figure 80:
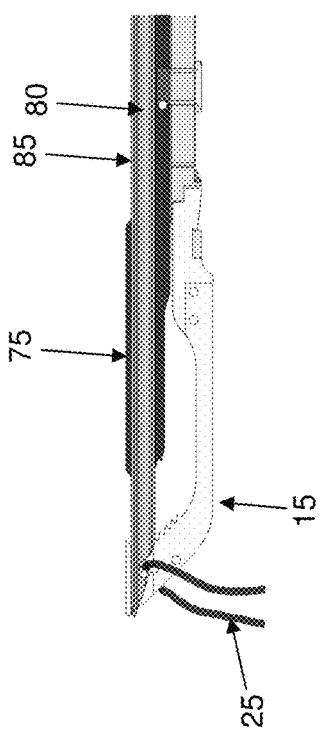
Figure 82:
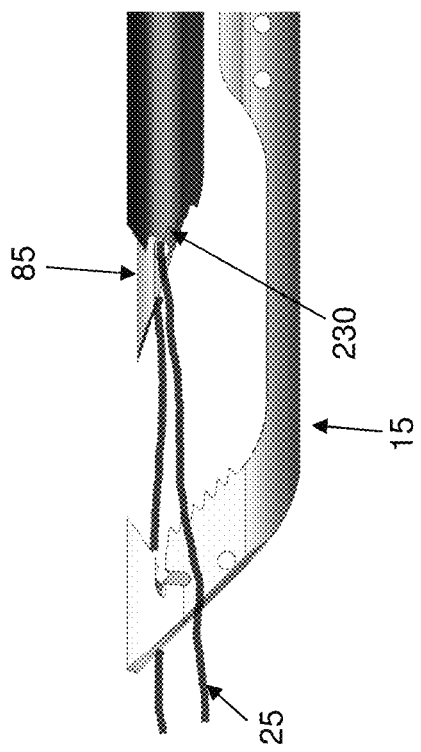
Figure 81:
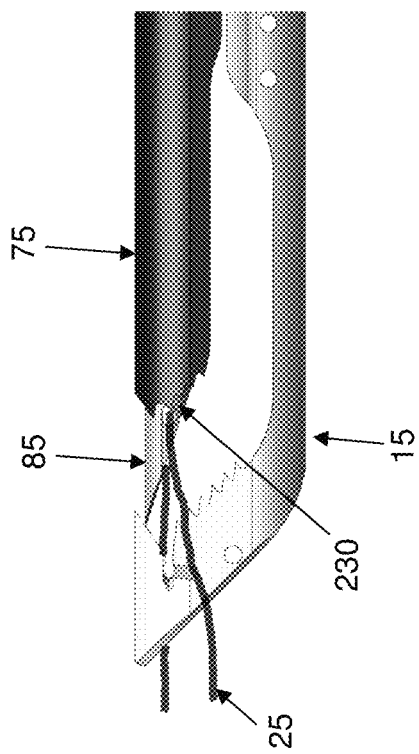
Figure 84:
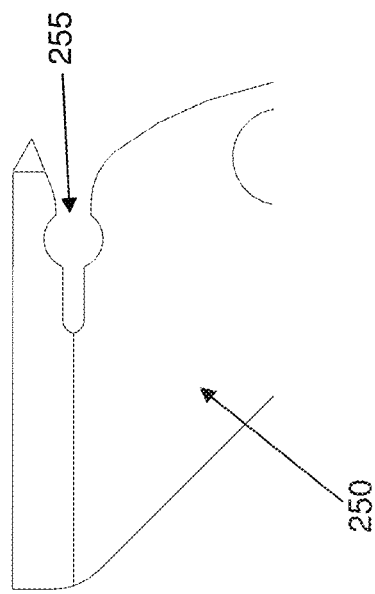

By way of further explanation, FIGS. 68A and 68B show the configuration of the suture passer prior to suture passer being loaded with suture. FIGS. 68C and 68D show the configuration of the suture passer after the suture passer has been loaded with suture (note that in FIGS. 68C-68N, the suture is omitted from the drawings for clarity of illustration). FIGS. 68E and 68F show initial engagement of inner needle 80 with distal jaw spring 55 during the forward stroke of inner needle 80 and outer needle 85. FIGS. 68G and 68H show inner needle 80 camming distal jaw spring 55 downward during a later stage in the forward stroke of inner needle 80 and outer needle 85. FIGS. 68I and 68J show the maximum distal extension of inner needle 80 during the forward stroke of inner needle 80 and outer needle 85. FIGS. 68K and 68L show inner needle 80 retracting proximally from the position shown in FIGS. 68I and 68J. FIGS. 68M and 68N show inner needle 80 and outer needle 85 having moved proximally of distal jaw spring 55, such that distal jaw spring 55 has returned to its original position of FIGS. 68A and 68B.

Figure 83:
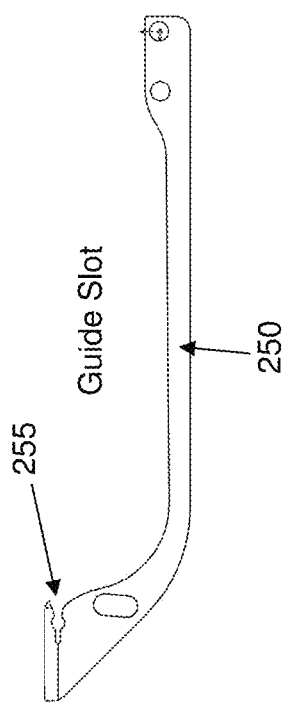
Figure 86:
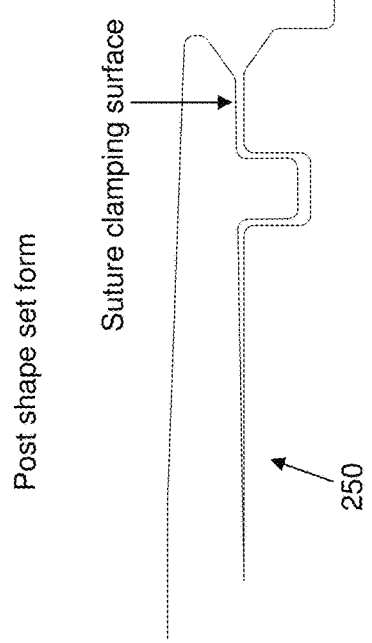
FIGS. 85-89 are schematic views showing an alternative form of the distal jaw spring of the novel suture passer of FIGS. 69-84.
Figure 85:
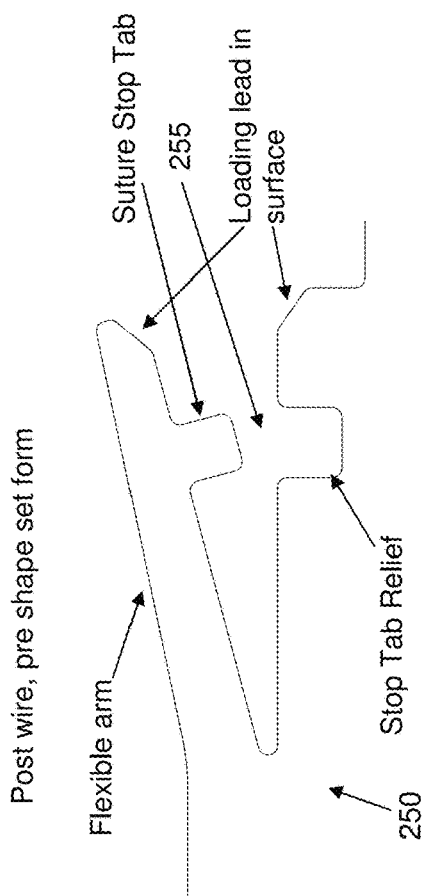
Figure 87:
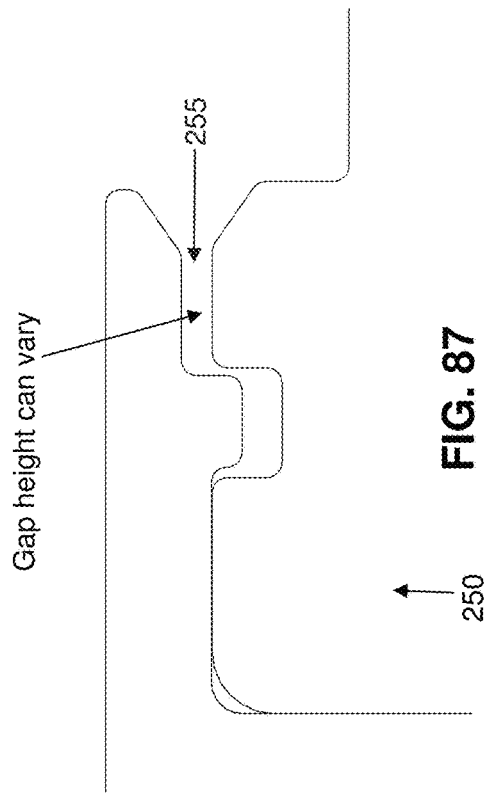
Figure 88:
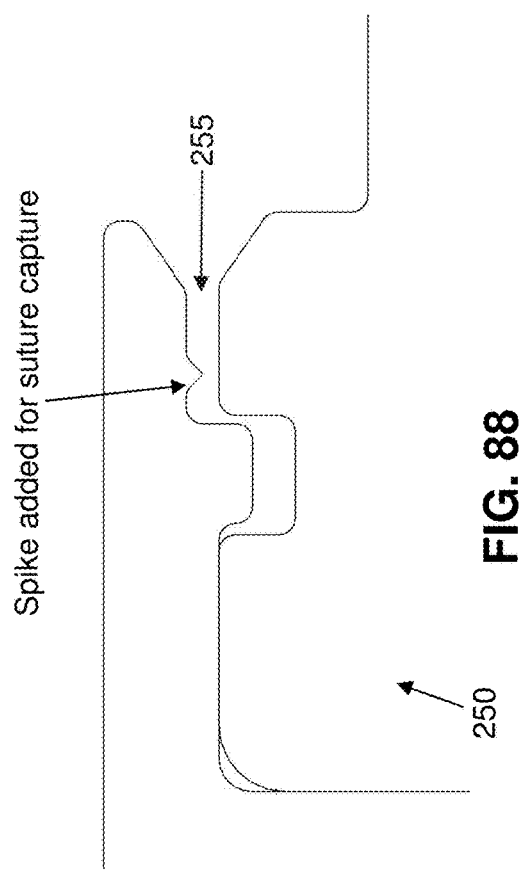
Figure 89:
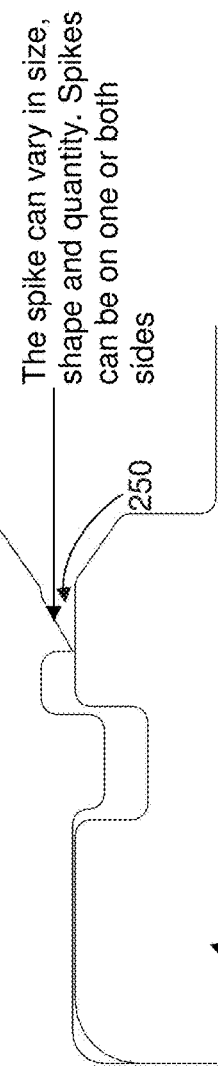

FIGS. 69-84 show another preferred construction of the present invention. More particularly, the construction shown in FIGS. 69-84 is generally similar to the construction shown in FIGS. 55-68, except that (i) distal jaw spring 55 and suture capture block 245 are replaced by a distal jaw spring 250 (FIG. 83) having a suture guide slot 255 formed therein, and (ii) outer needle 85 is replaced by the outer needle 85 with suture slot 230 shown in FIGS. 51 and 52. In this form of the invention, suture 25 is spring-held in suture guide slot 255, and follows the path of suture slot 30 as distal jaw spring 250 is displaced by inner needle 80.

FIGS. 85-89 show alternative constructions for releasably capturing suture 25 to distal jaw spring 250.

Figure 90:
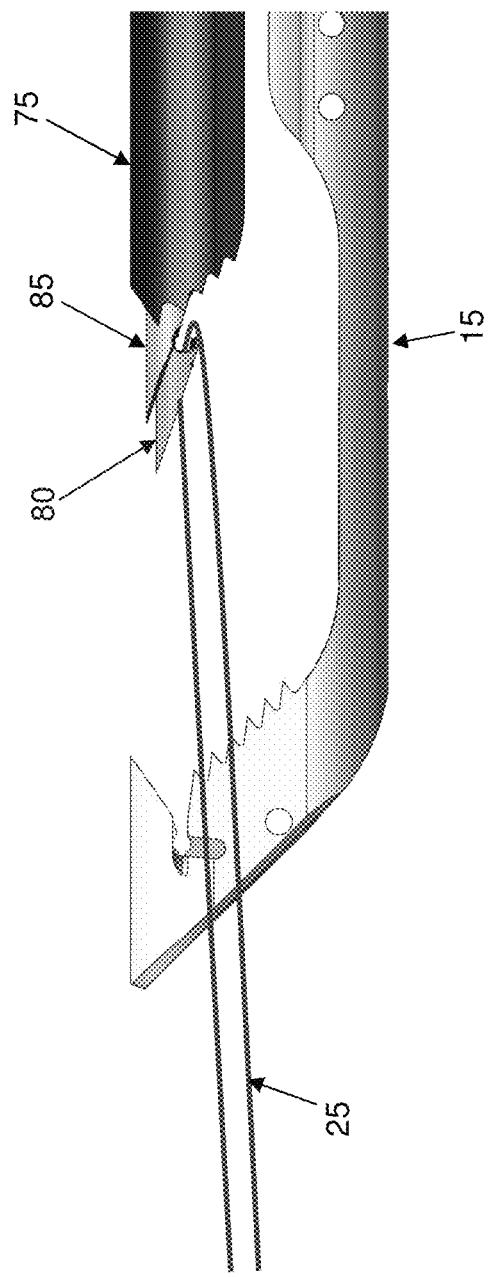
FIG. 90 is a schematic view showing another alternative construction for the novel suture passer of the present invention.
Figure 91:
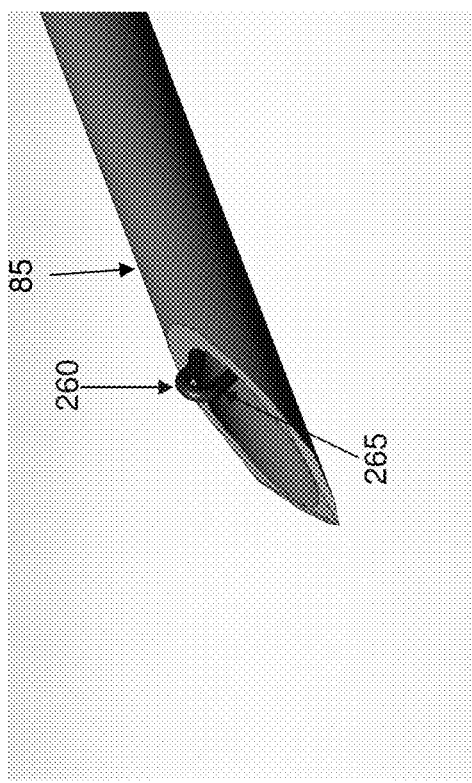
FIGS. 91-94 are schematic views showing still another alternative construction for the novel suture passer of the present invention.
Figure 92:
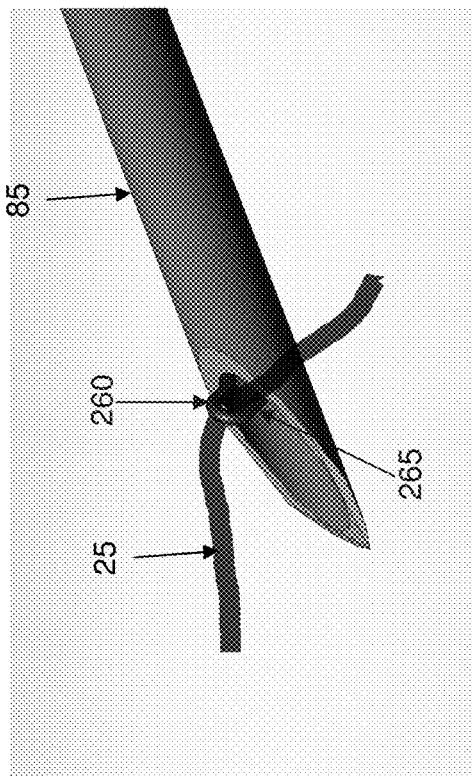
Figure 93:
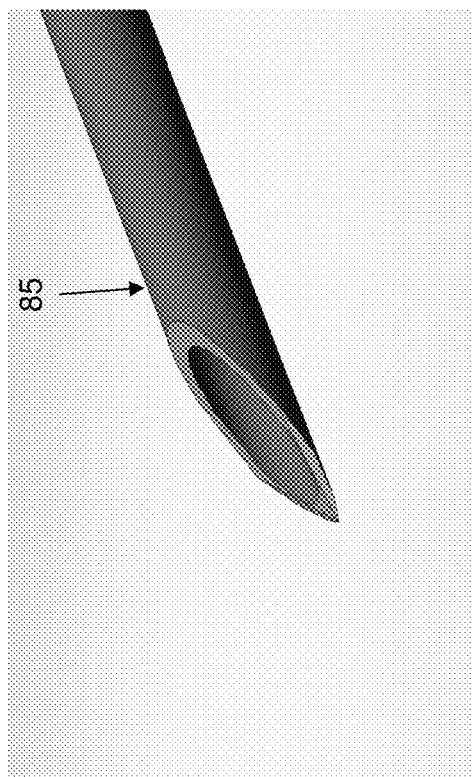
Figure 94:
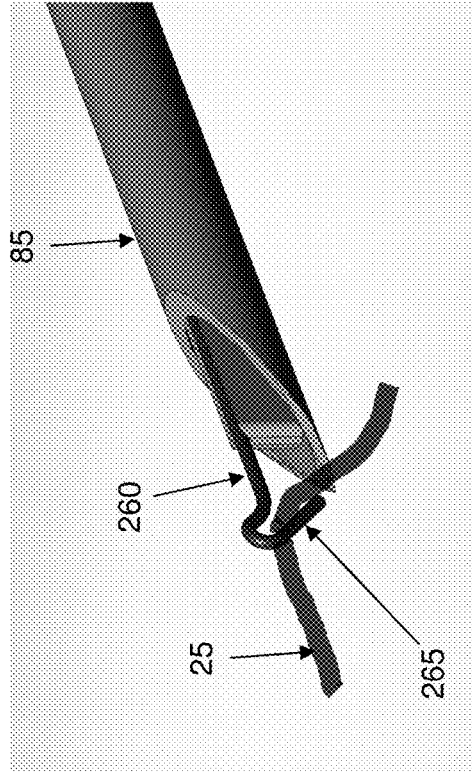

FIG. 90 shows another preferred construction of the present invention. More particularly, the construction shown in FIG. 90 is generally similar to the construction shown in FIGS. 69-84, except that outer needle 85 lacks suture slot 230 and may or may not directly engage suture 25 and may or may not assist in capturing suture 25 to inner needle 80.

FIGS. 90A, 90B and 90C show another preferred embodiment of the present invention. More particularly, in this form of the invention, outer needle 85 is formed with an inclined tip 256, however, this inclined tip is offset 180 degrees from the inclined surface 107 of inner needle 80, whereby to enhance suture gripping between suture slot 110 of inner needle 80 and inclined tip 256 of outer needle 85. Furthermore, in this form of the invention, distal jaw spring 55 is omitted and suture 25 is held in suture slot 30 of distal jaw 15 by friction.

FIGS. 90D, 90E, 90F, 90G and 90I show a suture passing operation using the suture passer of FIGS. 90A, 90B and 90C.

It should also be noted that inner needle 80 can be replaced by a wire with a loop on the end that can capture the suture (e.g., in the manner of a suture threader) and pull it into the outer needle. See, for example, FIGS. 91-94, where a wire 260, having a hook 265, grapples the suture and pulls it into outer needle 85.

It should also be noted that inner needle 80 (as shown in FIGS. 21-23) can function without an outer needle 85. In this embodiment, the inner needle 80 serves to pick up the suture and carry it proximally without the assistance of the outer needle 85.

Figure 95:
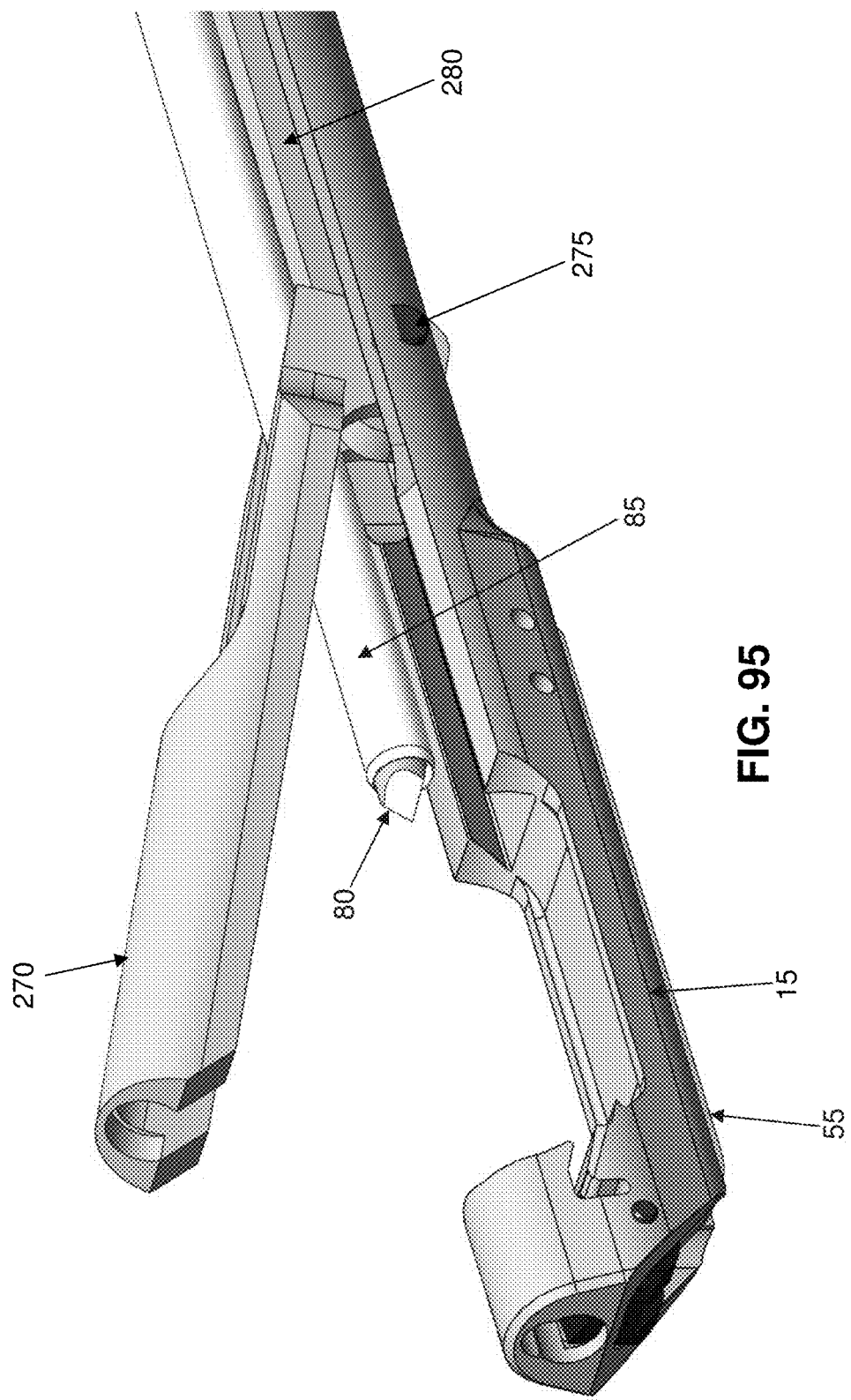
FIG. 95 is a schematic view showing another form of the novel suture passer of the present invention.

FIG. 95 shows another preferred embodiment of the present invention. More particularly, in this form of the invention, the longitudinally-reciprocating proximal jaw 75 of the suture passer shown in FIGS. 16 and 17 is replaced by a pivoting proximal jaw 270. More particularly, proximal jaw 270 is mounted to elongated shaft 10 via a pivot pin 275, such that longitudinal motion of a drive rod 280 (connected at its proximal end to proximal jaw carriage 205) causes proximal jaw 270 to pivot about pivot pin 275, whereby to open and close the jaw relative to distal jaw 15.

Figure 96:
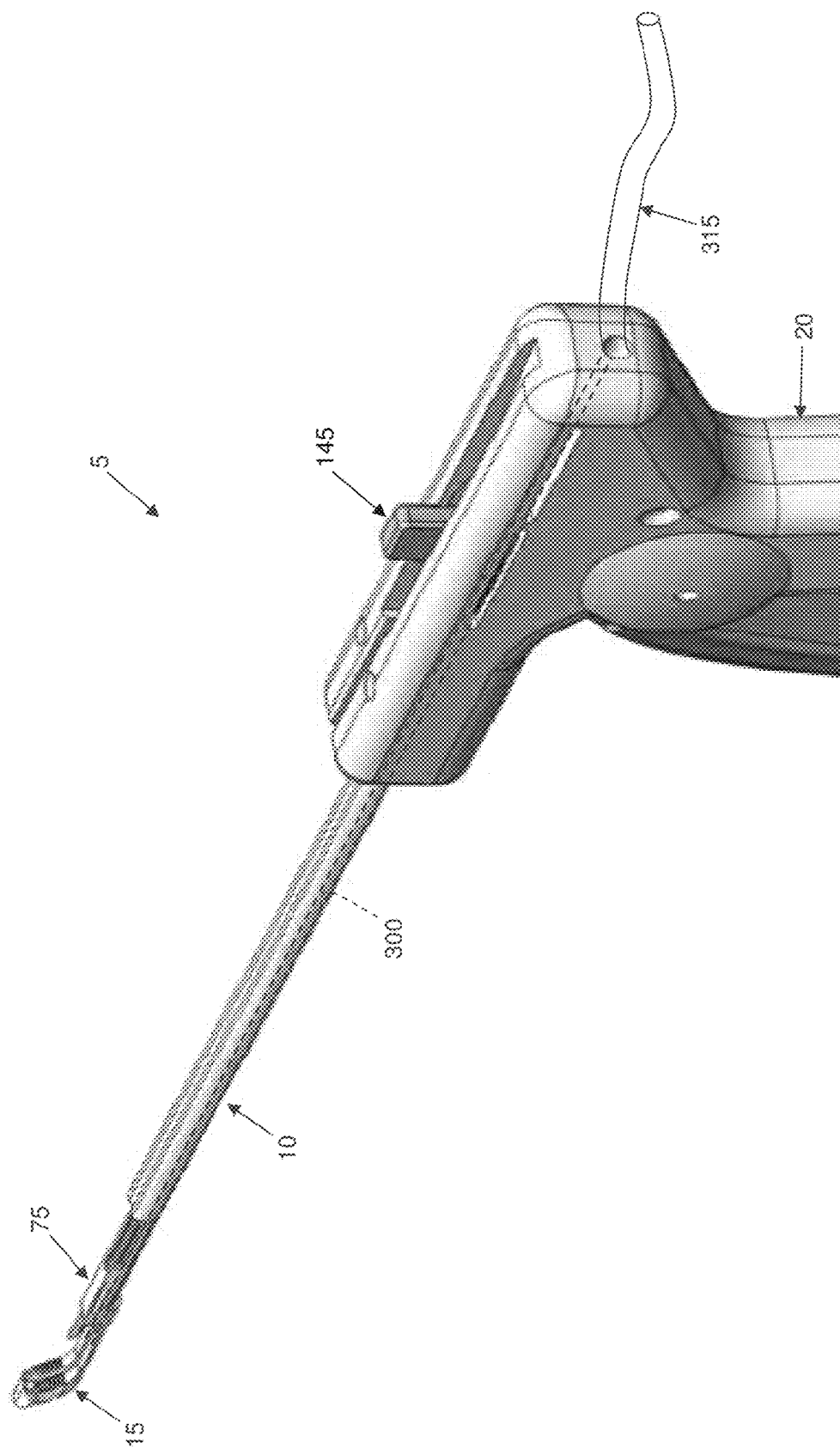
FIGS. 96 and 97 are schematic views showing another alternative construction for the novel suture passer of the present invention.
Figure 97:
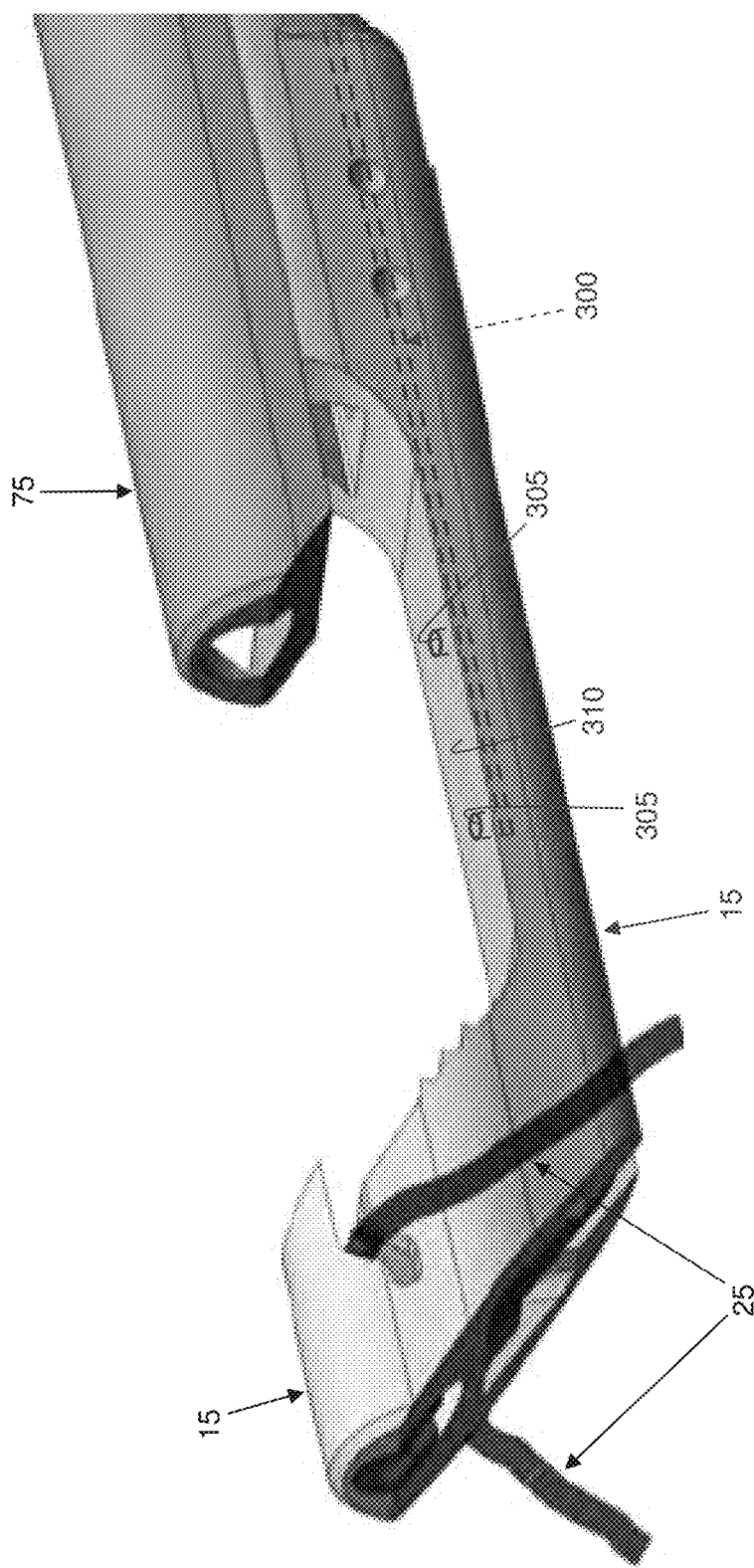

Looking next at FIGS. 96 and 97, there is shown another suture passer 5 formed in accordance with the present invention. For purposes of illustration but not limitation, the suture passer 5 shown in FIGS. 96 and 97 is shown to have the distal jaw construction of FIGS. 18 and 19, however, other distal jaw constructions may also be utilized. In this form of the invention, suture passer 5 is constructed so that its distal jaw 15 has an interior passageway 300 extending through the distal jaw. Passageway 300 terminates at its distal end in one or more apertures 305 which open on surface 310 of distal jaw 15. Passageway 300 terminates at its proximal end in a vacuum fitting 315 which is disposed on the handle 20 of suture passer 5. In this form of the invention, suction (e.g., from a conventional vacuum source) may be applied to vacuum fitting 315, whereby suction will be established at apertures 305 in surface 310 of distal jaw 315, whereby to draw tissue towards apertures 305 and/or to secure tissue to apertures 305 and thereby facilitate subsequent clamping of the tissue with proximal jaw 75.

Looking next at FIGS. 98-101, there is shown another suture passer 5 also formed in accordance with the present invention. In the suture passer 5 shown in FIGS. 98-101, distal jaw 15 comprises two suture slots 30A, 30B. Suture slot 30A preferably has a configuration similar to that shown in FIGS. 68A-68N. Suture slot 30B preferably has a somewhat different configuration, comprising a vertical slot 320 communicating with a horizontal slot 325. In this form of the invention, a loop 325 of suture 25 is passed across suture slot 30B and then back across suture slot 30A so that two strands of suture 325A, 325B are presented to inner needle 80 for sequential pickup. To this end, distal jaw spring 55 has a suture seat which is sized to interface with both suture strand 325A and suture strand 325B when they are disposed in suture slots 30A, 30B, respectively, whereby to releasably hold suture strands 325A, 325B to distal jaw 15. Alternatively, distal jaw spring 55 could be provided with two separate suture seats, one disposed adjacent suture slot 30A and one disposed adjacent suture slot 30B, whereby to releasably hold suture strands 325A, 325B to distal jaw spring 315. This form of the invention can be highly useful where suture is to be passed through tissue multiple times.

Figure 103:
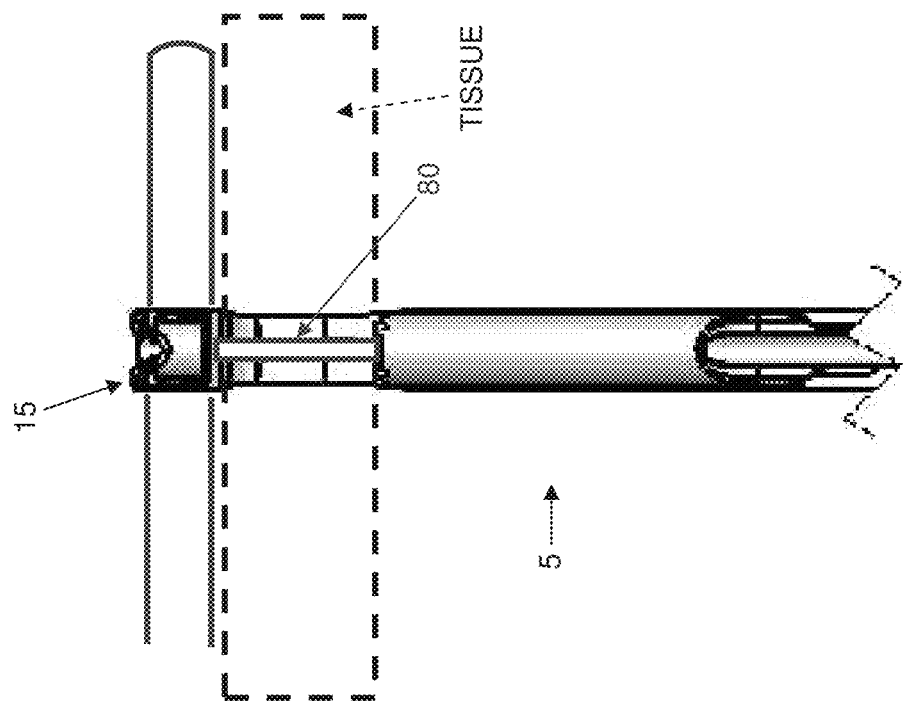
Figure 102:
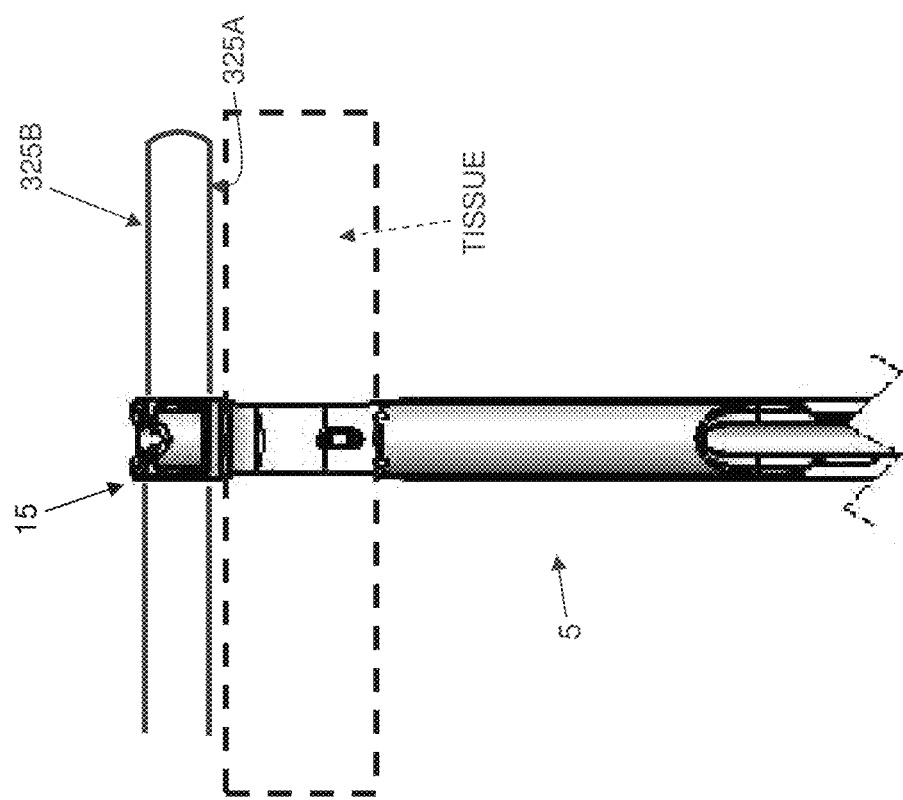
Figure 105:
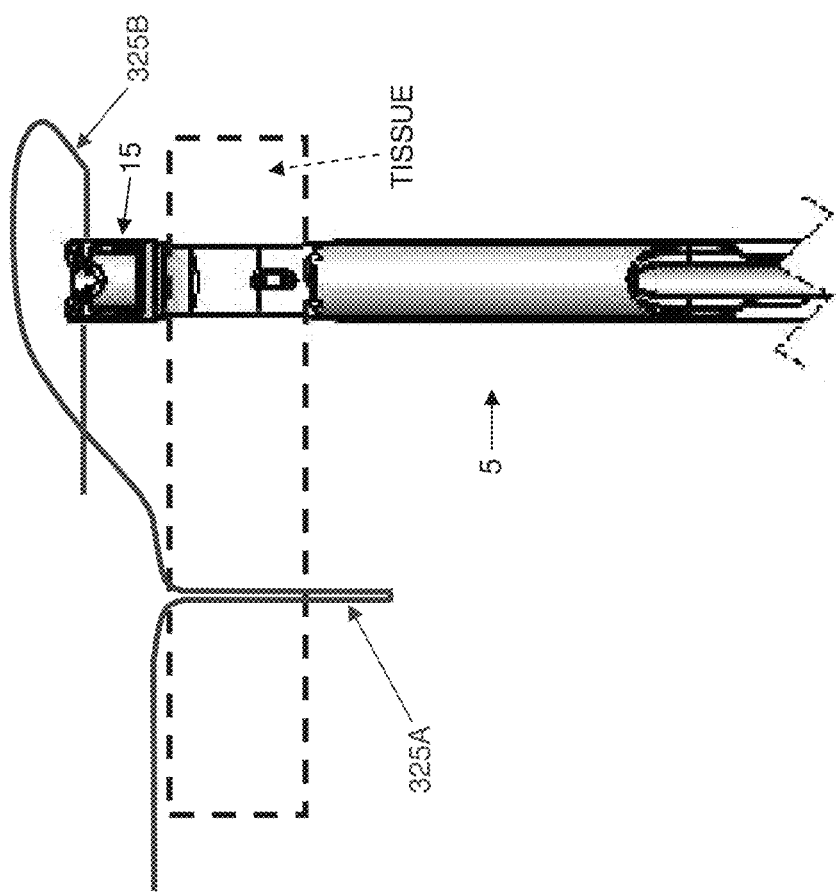
Figure 104:
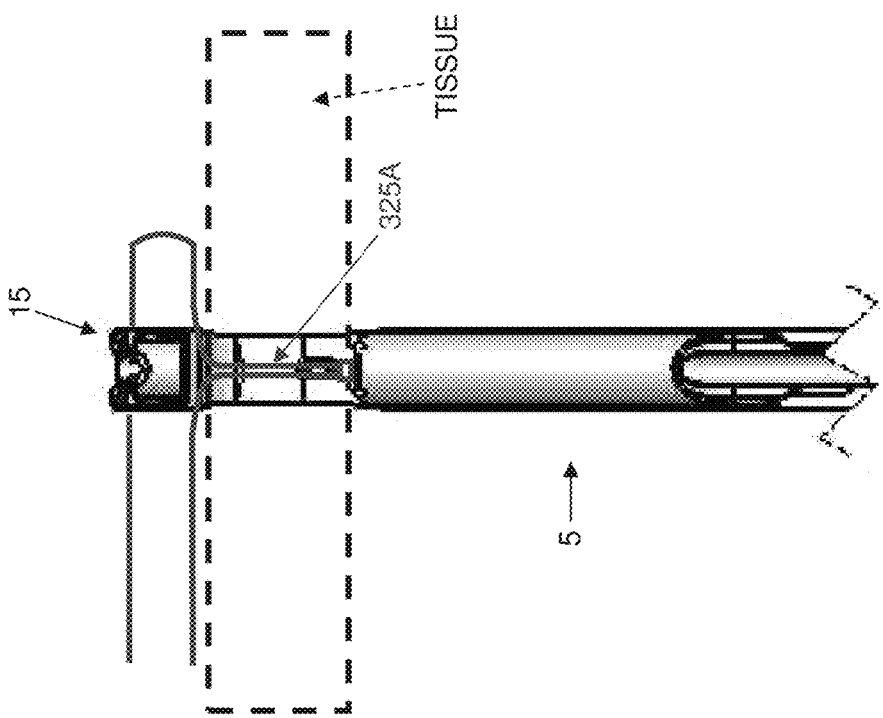
Figure 107:
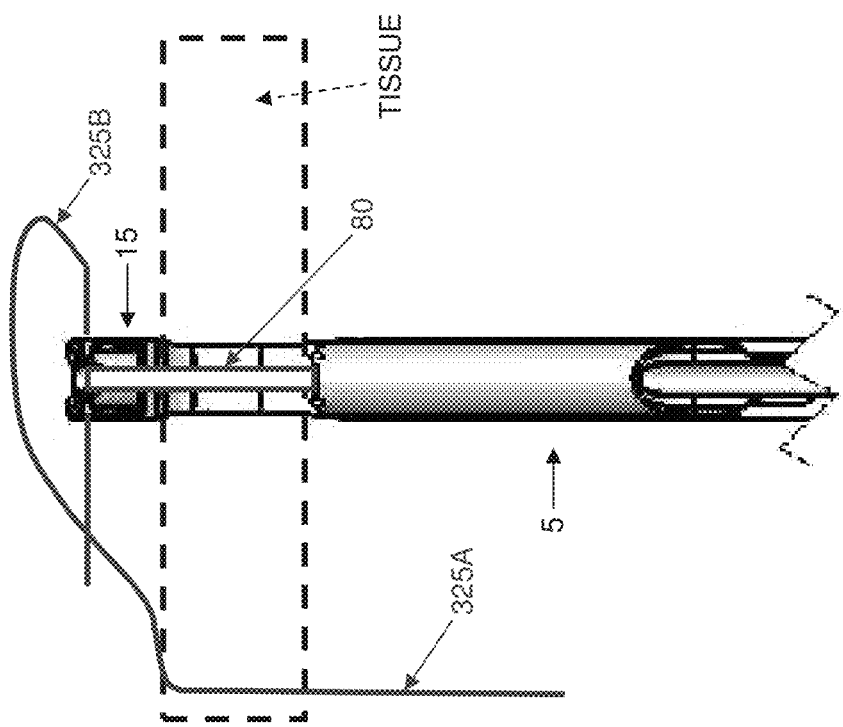
Figure 106:
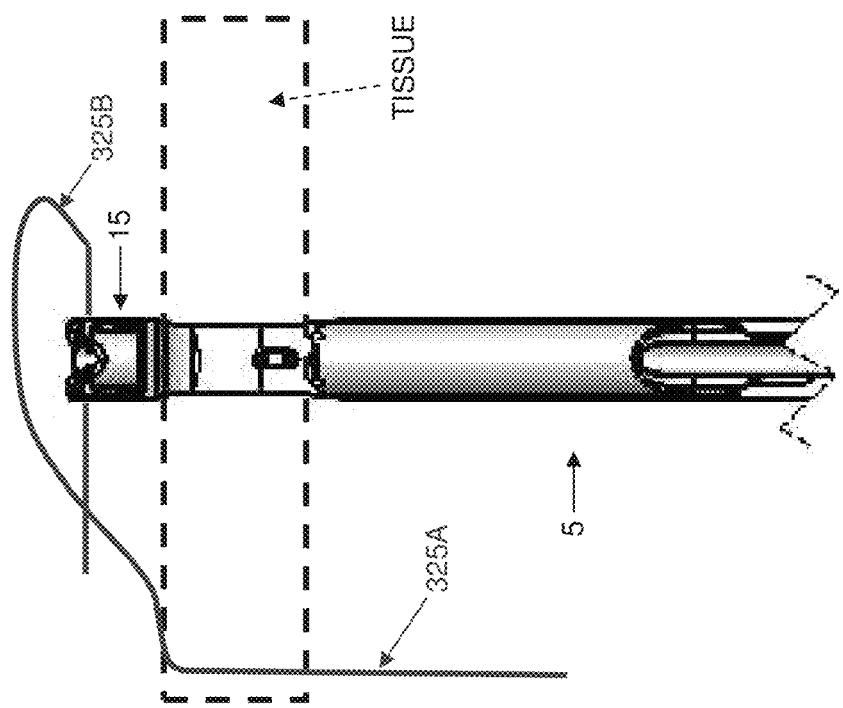
Figure 109:
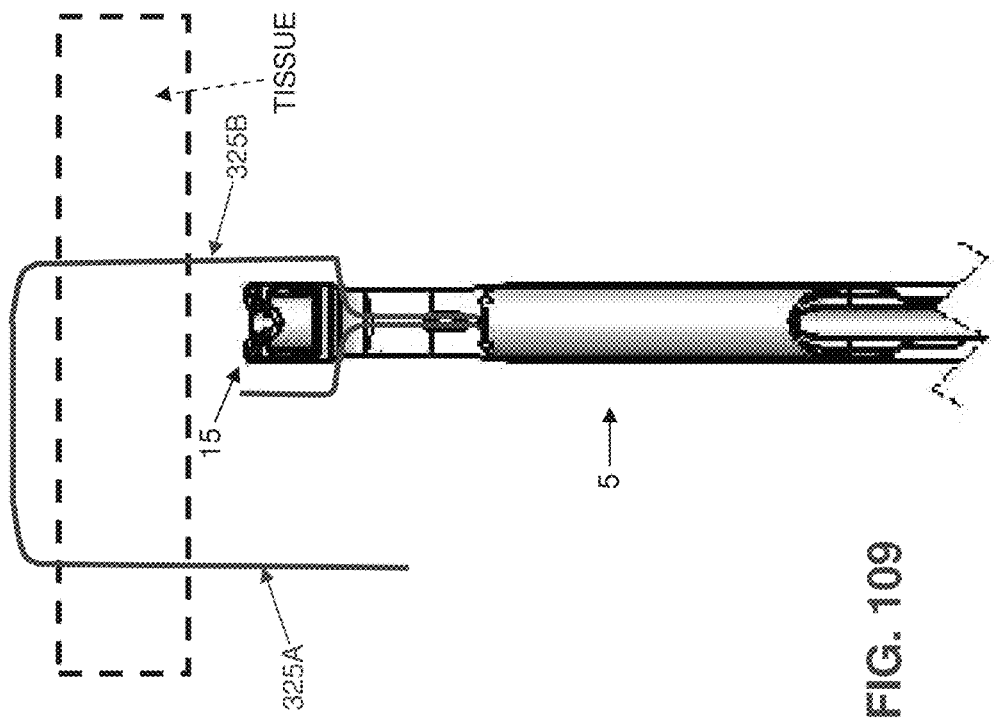
Figure 108:
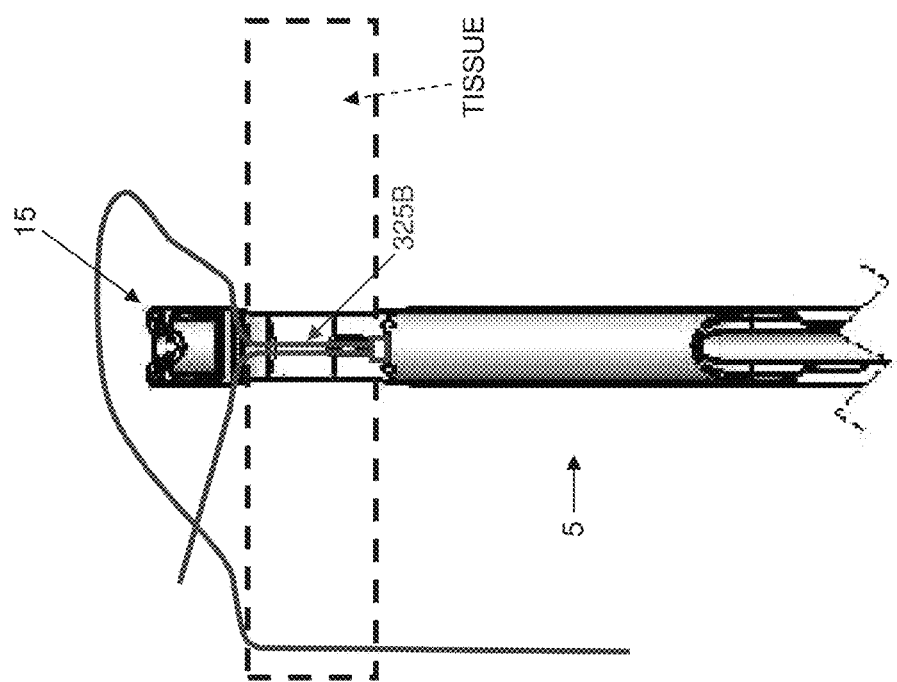

By way of example but not limitation, in one exemplary suture passing operation, a suture passer 5 carrying a loop 325 of suture 25 is positioned adjacent the tissue (FIG. 102). Next, inner needle 80 is passed through the tissue so as to pick up the strand 325A of suture passing through suture slot 30A (FIG. 103). Inner needle 80 is withdrawn back through the tissue, carrying the strand 325A with it (FIG. 104). The strand 325A of suture is released from the suture passer 5, and the suture passer 5 is shifted laterally so it is in a location where a second strand of suture is to be passed (FIG. 105). Preferably the first strand 325A of suture is pulled completely through the tissue, e.g., with a separate grasping tool (not shown) (FIG. 106). Then inner needle 80 is passed through the tissue so as to pick up the strand 325B of suture passing through suture slot 30B (FIG. 107). Inner needle 80 is withdrawn back through the tissue, carrying the strand 325B with it (FIG. 108). The suture passer 5 is withdrawn away from the tissue (FIG. 109), and then the strand 325B is released from the suture passer 5, thereby leaving the loop 325 of suture 25 extending through the tissue (FIG. 110).

Figure 111:
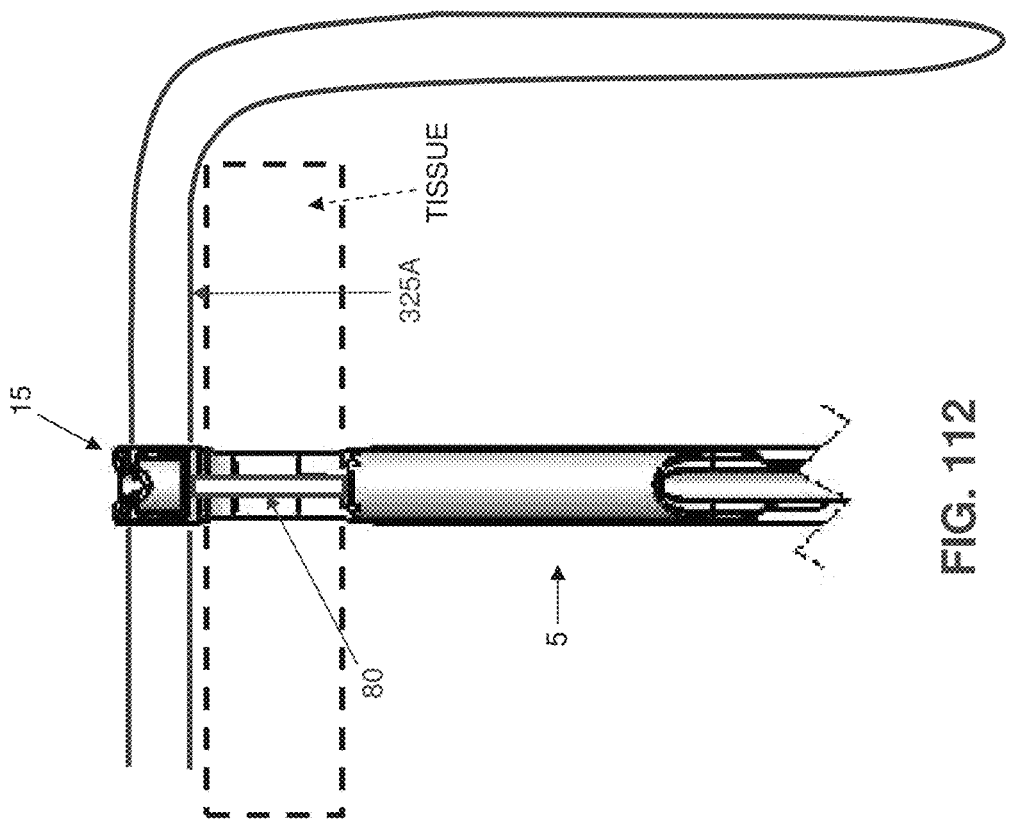
Figure 112:
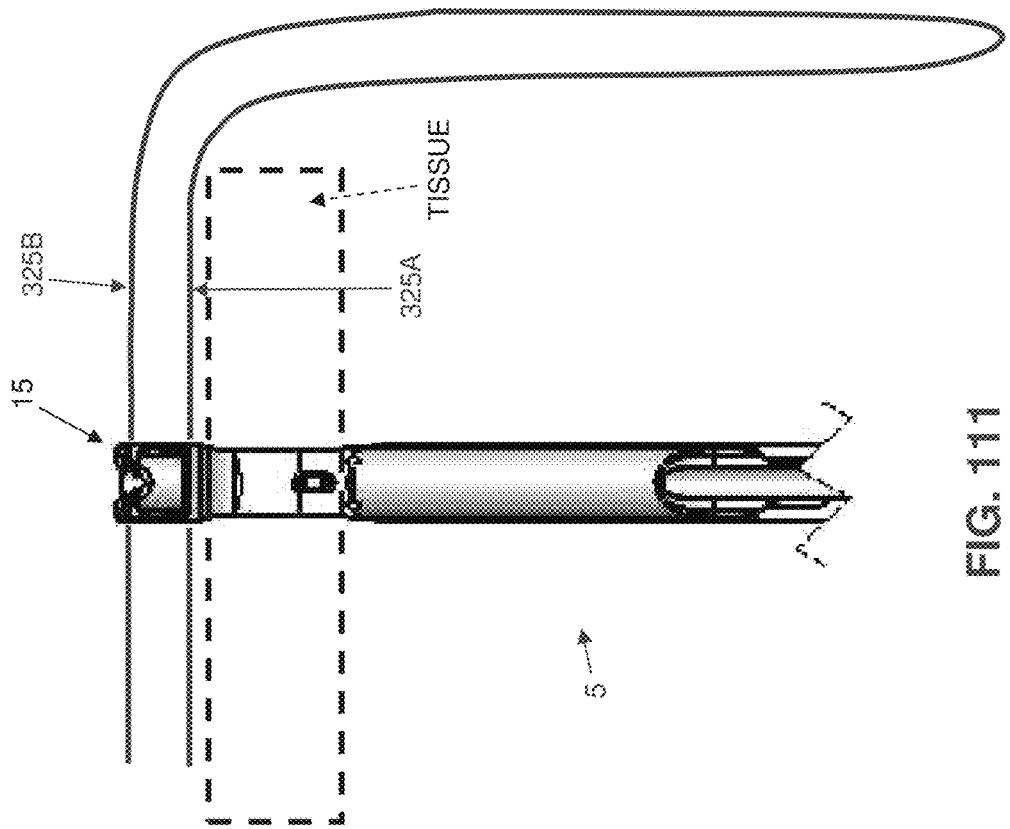
Figure 114:
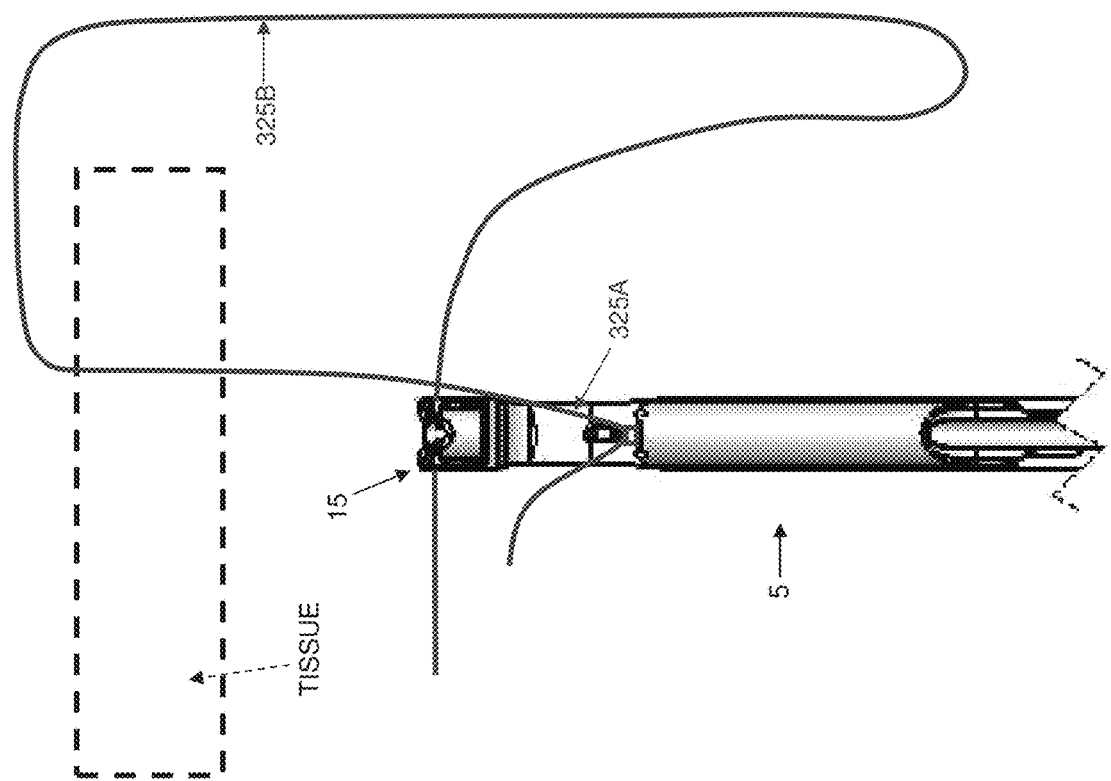
Figure 113:
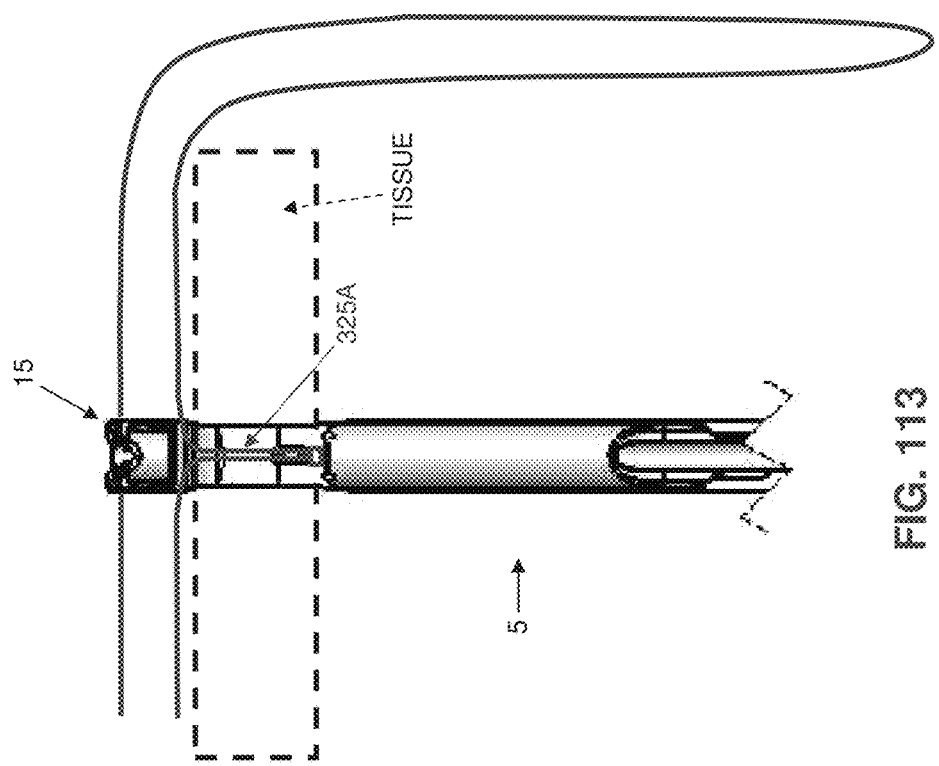
Figure 116:
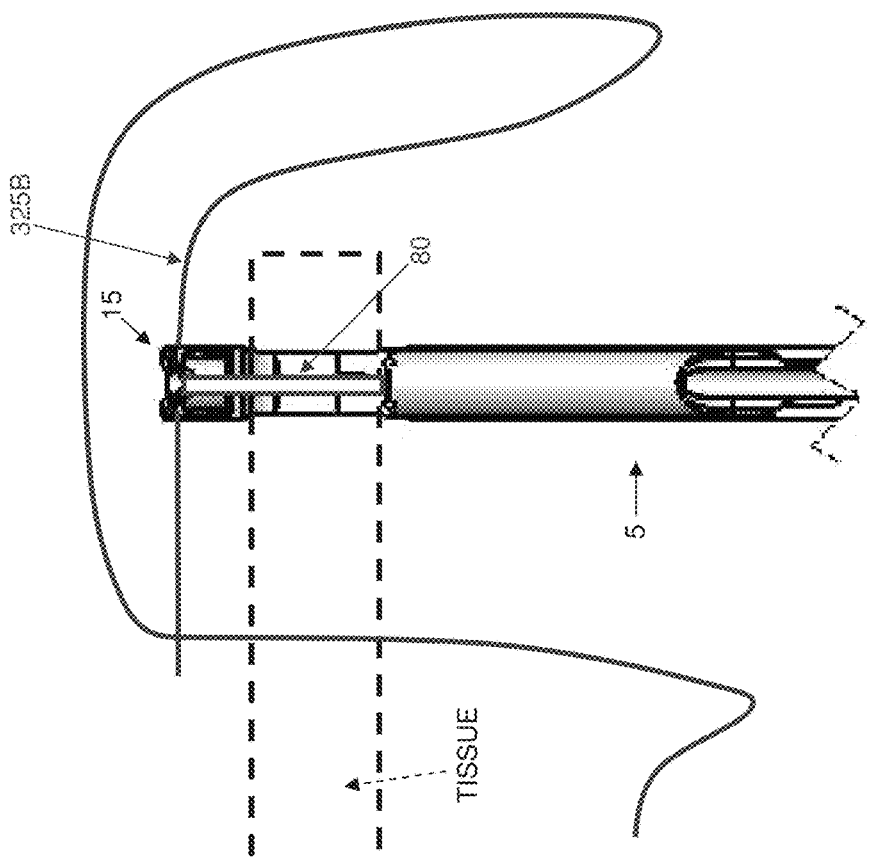
Figure 115:
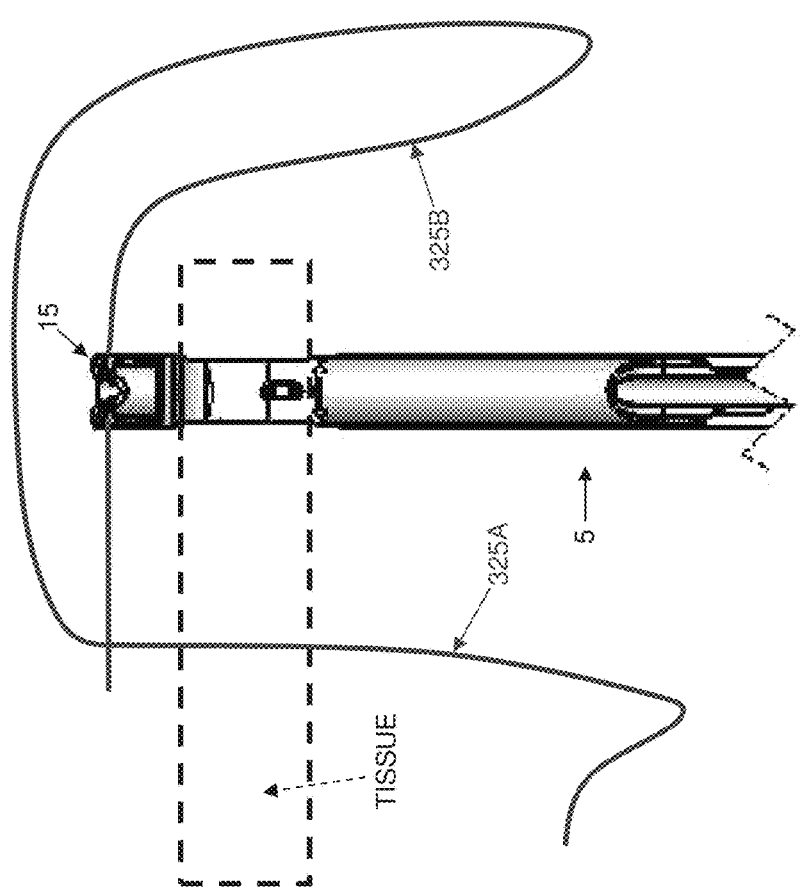
Figure 117:
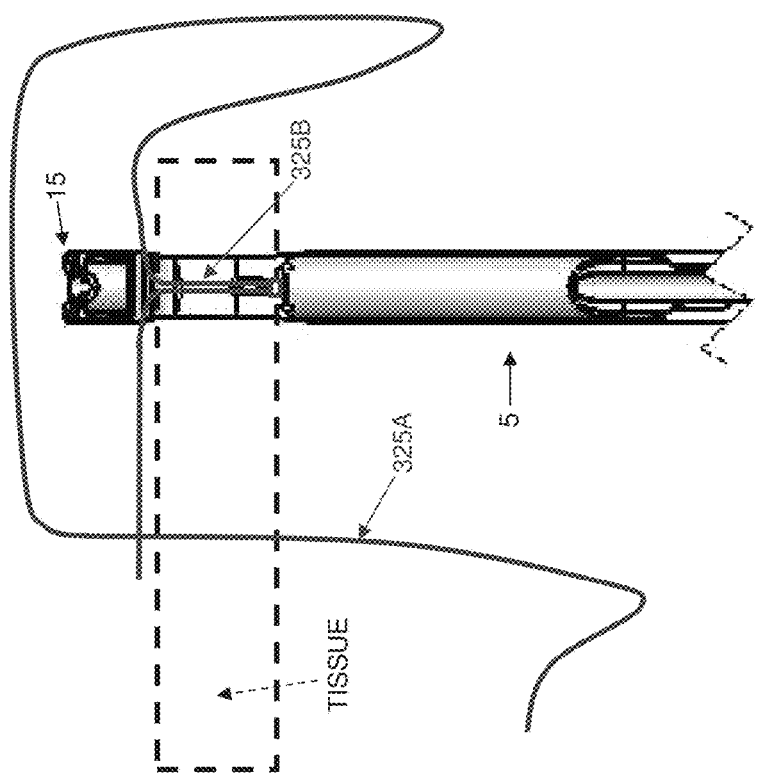
Figure 118:
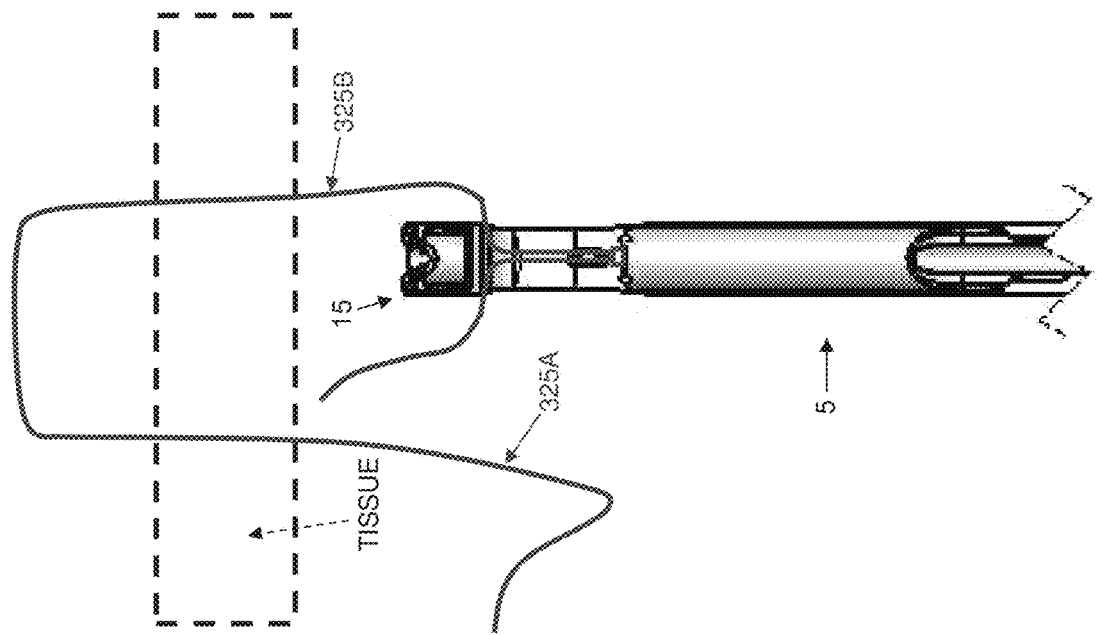

By way of further example but not limitation, in another exemplary suture passing operation, a suture passer 5 carrying a loop 325 of suture 25 is positioned adjacent the tissue (FIG. 111). Next, inner needle 80 is passed through the tissue so as to pick up the strand 325A of suture passing through suture slot 30A (FIG. 112). Inner needle 80 is withdrawn back through the tissue, carrying the strand 325A with it (FIG. 113). The suture passer 5 is moved away from the tissue (FIG. 114). Preferably the first strand of suture is pulled completely through the tissue, e.g., by withdrawing the suture passer 5 (FIG. 114). Then the strand 325A of suture is released from the suture passer 5, and the suture passer 5 is advanced back to the tissue and shifted laterally so it is in a location where a second strand of suture is to be passed (FIG. 115). Then inner needle 80 is passed through the tissue so as to pick up the strand 325B of suture passing through suture slot 30B (FIG. 116). Inner needle 80 is withdrawn back through the tissue, carrying the strand 325B with it (FIG. 117). The suture passer 5 is withdrawn away from the tissue (FIG. 118), and the suture is released from the suture passer 5, thereby leaving the loop of suture 325 extending through the tissue (FIG. 119).

USE OF THE PRESENT INVENTION FOR OTHER APPLICATIONS

It should be appreciated that the present invention may be used to arthoscopically suture the fibrous capsule of the hip joint, so as to facilitate arthroscopic procedures on the hip joint. The present invention can also be used to arthroscopically suture other tissue, both in the hip joint and in locations other than the hip joint.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method of passing a suture through a portion of tissue, the method comprising:
   retaining a portion of a suture in a slot of a first jaw located at a distal end of a shaft of a suture passer, the slot facing in a proximal direction and oriented so that the portion of the suture extends transversely to a longitudinal axis of the shaft;
   disposing the portion of tissue between the first jaw and a second jaw that is translatably mounted to the shaft;
   gripping the portion of tissue by translating the second jaw along the shaft toward the first jaw;
   advancing a distal portion of a needle movably mounted to the shaft through the portion of tissue and hooking the suture with a hook of the needle; and
   retracting the distal portion of the needle back through the portion of tissue to pull the suture out of the slot and free of the first jaw and pass the suture through the portion of tissue,
   wherein retaining the portion of the suture in the slot of the first jaw comprises biasing the portion of the suture in the slot in a first direction, and wherein the hook is open toward a second direction that is opposite the first direction.

2. The method of claim 1, comprising passing a loop of the suture through an opening in the tissue created by the needle.

3. The method of claim 1, wherein the tissue is a capsule of a joint.

4. The method of claim 3, wherein the joint is a hip joint.

5. The method of claim 1, wherein the shaft comprises an opening within which the portion of tissue is disposed and the opening is open toward the first direction.

6. The method of claim 1, wherein:
   gripping the portion of tissue by translating the second jaw along the shaft toward the first jaw comprises squeezing a first portion of a handle assembly and a second portion of the handle assembly together by a first amount, advancing the distal portion of the needle through the portion of tissue comprises squeezing the first portion and the second portion together by a second amount, and retracting the distal portion of the needle back through the portion of tissue comprises moving the first and second portions apart.

7. The method of claim 1, wherein the shaft comprises a channel that is proximal of the first jaw and at least a portion of the needle is received in the channel.

8. The method of claim 1, wherein the second jaw comprises a lumen and at least a portion of the needle is received in the lumen.

9. The method of claim 1, wherein the first jaw comprises an aperture, the slot is located proximally of at least a portion of the aperture, and a distal end of the needle is translatable through the aperture.

10. The method of claim 1, wherein the suture is hooked on a return stroke of the needle.

11. The method of claim 1, wherein the slot comprises a horizontally extending proximal section and a vertically extending distal section.

12. The method of claim 1, wherein the needle is removable from the shaft.

13. A method of passing a suture through a portion of tissue, the method comprising:

grasping a handle assembly of a suture passer, wherein a first portion of the handle assembly is configured to move relative to a second portion of the handle assembly when a user squeezes on the handle assembly;

squeezing the first portion and the second portion together by a first amount to translate a first jaw mounted to a shaft of the suture passer in a longitudinal direction of the shaft toward a second jaw of the suture passer for gripping a portion of tissue between the first and second jaws;

squeezing the first portion and the second portion together by a second amount to translate a needle of the suture passer through the portion of tissue gripped between the first and second jaws and hook a portion of suture on a hook of the needle; and moving the first and second portions apart to retract the needle through the portion of tissue and pass the portion of suture through the portion of tissue, wherein prior to hooking the portion of the suture on the needle, the portion of suture is retained in a slot of the first jaw via a spring that biases the portion of suture in a first direction, and wherein the hook is open toward a second direction that is opposite the first direction.

14. The method of claim 13, wherein the tissue is a capsule of a joint.

15. The method of claim 14, wherein the joint is a hip joint.

16. The method of claim 13, comprising passing a loop of the suture through an opening in the tissue created by the needle.

17. The method of claim 13, wherein the shaft comprises an opening within which the portion of tissue is disposed and the opening is open toward the first direction.

18. The method of claim 13, wherein the shaft comprises a channel that is proximal of the first jaw and at least a portion of the needle is received in the channel.

19. The method of claim 13, wherein the second jaw comprises a lumen and at least a portion of the needle is received in the lumen.

20. The method of claim 13, wherein the first jaw comprises an aperture, the slot is located proximally of at least a portion of the aperture, and a distal end of the needle is translatable through the aperture.

21. The method of claim 13, wherein the suture is hooked on a return stroke of the needle.

22. The method of claim 13, wherein the slot comprises a horizontally extending proximal section and a vertically extending distal section.

23. The method of claim 13, wherein the needle is removable from the shaft.

* * * * *